`US005939289A`

United States Patent [19]
Ertesvåg et al.

[11] Patent Number: 5,939,289
[45] Date of Patent: Aug. 17, 1999

[54] DNA COMPOUNDS COMPRISING SEQUENCES ENCODING MANNURONAN C-5-EPIMERASE

[75] Inventors: Helga Ertesvåg, Trondheim; Svein Valla, Vikhamar; Gudmund Skjåk-Braek, Trondheim; Bjørn Larsen, Sjetnemarka, all of Norway

[73] Assignees: Pronova Biopolymer a.s., Drammen, Norway; Nobipol, Trondheim, Norway

[21] Appl. No.: 08/387,942
[22] PCT Filed: Oct. 8, 1993
[86] PCT No.: PCT/NO93/00151
§ 371 Date: May 9, 1995
§ 102(e) Date: May 9, 1995
[87] PCT Pub. No.: WO94/09124
PCT Pub. Date: Apr. 28, 1994

[30] Foreign Application Priority Data

Oct. 8, 1992 [GB] United Kingdom .................. 9221163

[51] Int. Cl.⁶ ........................... C12P 19/00; C12P 21/04; C12N 1/00; C07H 21/04
[52] U.S. Cl. .................. 435/72; 435/69.7; 435/320.1; 435/831; 536/23.2; 536/23.4; 536/23.7
[58] Field of Search .............................. 536/23.2, 3, 23.4, 536/23.7; 435/72, 183, 69.7, 320.1, 831

[56] References Cited

FOREIGN PATENT DOCUMENTS

WO 86/03781   7/1986   WIPO .

OTHER PUBLICATIONS

Skjak–Braek et al. (1985) Carbohydrate Res. 139, 273–283.
Keil (1990) J. Gen. Microbiol. 136, 607–613.
Skjak–Braek, et al, Chem. Abstracts, vol. 102, No. 23, Abstract No. 200110x, p. 269 (Jun. 10, 1985).
Skjak–Braek, et al, Carbohydrate Research, vol. 103, pp. 133–136 (1982).
Haug, A. et al, Carbohydrate Research, vol. 17, pp. 297–308 (1971).
Patent Abstracts of Japan, vol. 13, No. 29, JP–A–63–233797 (Sep. 29, 1988).

*Primary Examiner*—Karen Cochrane Carlson
*Assistant Examiner*—Elizabeth Slobodyansky
*Attorney, Agent, or Firm*—Birch, Stewart, Kolasch & Birch, LLP

[57] ABSTRACT

DNA compounds encompassing sequences coding for enzymes having mannuronan C-5-epimerase activity are disclosed and a process for the preparation of such enzymes. The genetic sequences and enzymes prepared may be used in the production of alginates having a definite G/M ratio and block structure. Alginates having a definite G/M ratio may also be produced by selective inactivation of the genetic sequences.

16 Claims, 25 Drawing Sheets

Figure 1

Met-Asp-Tyr-Asn-Val-Lys-Asp-Phe-Gly-Ala-Leu-Gly-Asp-Gly-Val

5' ATG GAT TAT AAT GTN AAA GAT TTN GGN GCN TTA GGN GAT GGN GTN 3'

FIG.2
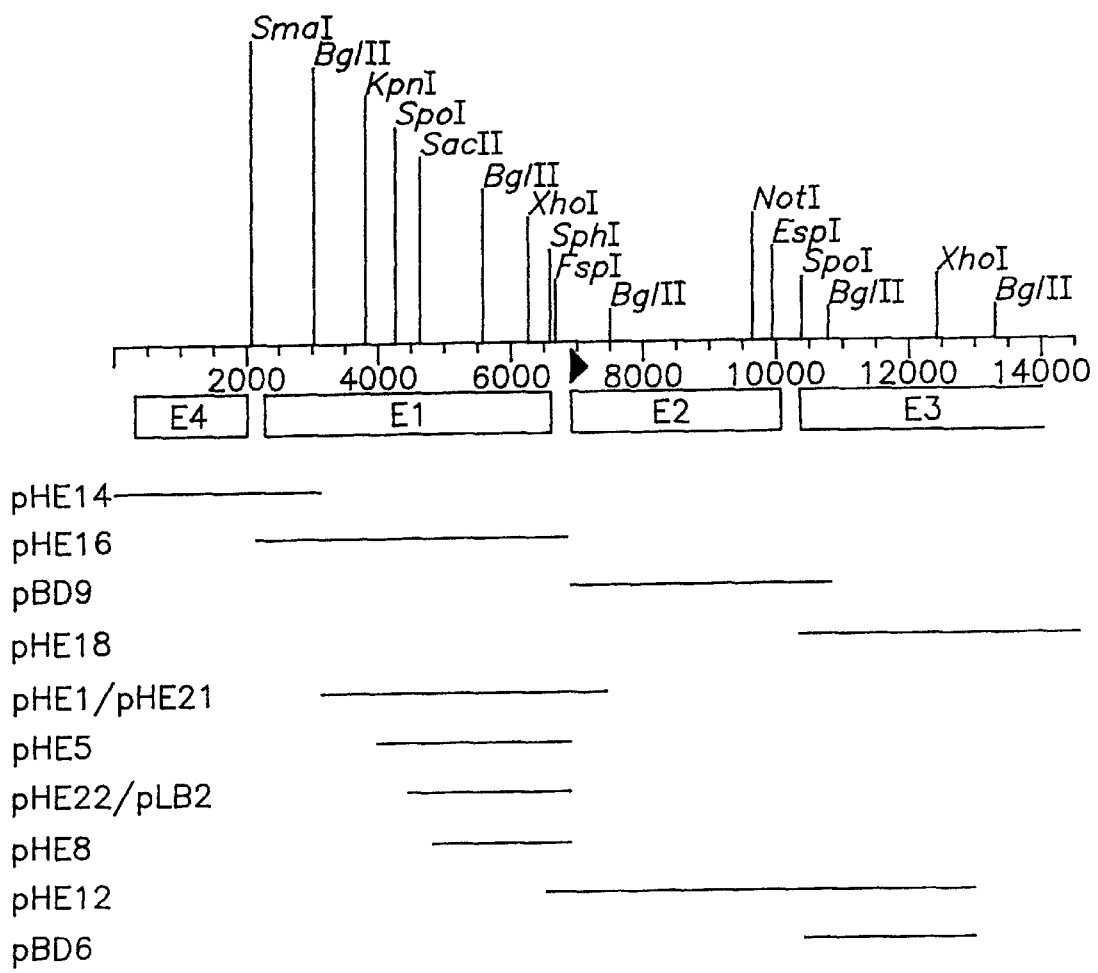
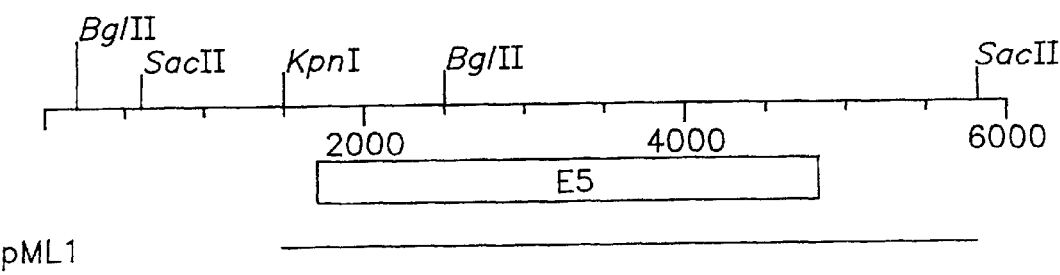

Figure 6A

```
E4A  ..............................T...T........C.      329
E1A1 .........................A...............         2266
E1A2 G..---.T...T.C......C.....C..G........C.          4798
E2A  ................A............G...........         6741
E3A1 .....C.T........A........................        10012
E3A2 G..---.T...T.C......C.....C..G........C.         12539
Con  ATGGATTACAACGTCAAGGATTTCGGGGCGCTGGGCGATG

E4A  ..............CG...CT....................          369
E1A1 .........................................         2266
E1A2 ...C.........CG.C........................         4838
E2A  .............T.....C.....................         6781
E3A1 ...C.....................................        10052
E3A2 ...C.........CG.C........................        12549
Con  GCGTCAGCGACGACACGGCGGCCATCCAGGCGGCGATCGA

E4A  ...............C.....T.....T.............          409
E1A1 C......C.......G.........................         2346
E1A2 C....................T...................         4878
E2A  .........................................         6821
E3A1 .......C.......G.........................        10092
E3A2 C........                                         12589
Con  TGCCGCCTACGCGGCCGGCGGCGGCACCGTCTACCTGCCG

E4A  ....................C..C..G..G......GGG..          449
E1A1 ........A..T.............................         2386
E1A2 ..............CC.AC..G.........GGG..              4918
E2A  ........A................................         6861
E3A1 ..T........T.............................        10132
Con  GCCGGCGAGTACCGGGTCAGCGGCGGCGAGGAGCCTTCCG

E4A  .............TGC.....GA.GG......CC.G.C...          489
E1A1 .T..T.GT.........................C.......         2426
E1A2 ............TGC      GA.GG......CC.G.C...         4958
E2A  .T..T............................C.......         6901
E3A1 .....GCG.................................        10172
Con  ACGGCTGCCTGACCATCAAGAGCAACGTCTATATCGTCGG

E4A  T.....C.............................A.....         529
E1A1 .....................................A....       2466
E1A2 ..A...C..A.....A.....C...............A.....       4998
E2A  ...G.................C.....................       6941
E3A1 .....................................A....      10212
Con  CGCCGGGATGGGCGAGACGGTGATCAAGCTGGTCGACGGC
```

Figure 6B

```
E4A  .CC..C.....GA.................C.............    569
E1A1 ...AC.......................................   2506
E1A2 .CC..C.....GA..........................T.     5038
E2A  .....T...G...............C..C...........      6981
E3A1 ...AC.................................T.     10252
Con  TGGGAGCAGAACGTCACCGGCATGGTGCGCTCGGCCTACG

E4A  .......A......................C.............   609
E1A1 .......A....................................  2546
E1A2 ....A.......................................  5078
E2A  ............................................  7021
E3A1 ............................................ 10292
Con  GCGAGGAGACCAGCAACTTCGGCATGAGCGACCTGACCCT

E4A  ............................................   649
E1A1 ....................CTGTC...C...............  2586
E1A2 ............................................  5118
E2A  ............................................  7001
E3A1 ....................CTGTC...C............... 10332
Con  CGACGGCAACCGCGACAACACCAGCGGCAAGGTCGACGGC

E4A  ................T.........GG................   689
E1A1 .........................................T.   2626
E1A2 ............................................  5158
E2A  ..................T......G..................  7101
E3A1 ..................T................T.....T. 10372
Con  TGGTTCAACGGCTACATCCCCGGCCAGGACGGCGCCGACC

E4A  ............A.C............GG...............   729
E1A1 ............................................  2606
E1A2 ..A........A.C..............................  5138
E2A  .....................................T..A...  7141
E3A1 .......................................A.... 10412
Con  GCGACGTGACCCTGGAGCGGGTGGAAATCCGCGAGATGTC

E4A  ..........C......C..C.......................   769
E1A1 ..................C..C......................  2706
E1A2 ......T..C..................................  5238
E2A  ...T........................................  7181
E3A1 ...T........................................ 10452
Con  CGGCTACGGTTTCGATCCGCACGAGCAGACCATCAACCTG
```

Figure 6C

```
E4A   ..............................        809
E1A1  .........................A......      2746
E1A2  ................................      5278
E2A   ................................      7221
E3A1  ................................     10492
Con   ACGATCCGCGACAGCGTGGCCCACGACAACGGCCTCGACG

E4A   ....................T.....A.A.C......    849
E1A1  ................................         2786
E1A2  ................T.....A.A.C.........     5318
E2A   .............T.T....A................    7261
E3A1  ................................        10532
Con   GCTTCGTCGCCGACTACCAGGTCGGCGGGGTGTTCGAGAA

E4A   .......G.C...GC...................      889
E1A1  ................................        2826
E1A2  .......G.C.......................       5358
E2A   ................................        7301
E3A1  ................................       10572
Con   CAACGTCTCGTACAACAACGACCGCCACGGCTTCAACATC

E4A   ...........C....T......A...C.......      929
E1A1  ................................        2866
E1A2  ............T....T......A...C......     5398
E2A   ................................        7341
E3A1  ................................       10612
Con   GTCACCAGCACCAACGACTTCGTCCTGAGCAACAACGTCG

E4A   ..............A..AG...............G..    969
E1A1  ................................        2906
E1A2  ........................AC.A.C.....G..   5438
E2A   ................................        7381
E3A1  ................................       10652
Con   CCTACGGCAACGGCGGCGCCGGCCTGGTGGTGCAGCGCGG

E4A   .TCT.G.G.....C..G.T....AG.A...........   1009
E1A1  .............C....T...................   2946
E1A2  .....G.G.............GAC...T..........   5478
E2A   ......C.....G...G..C..................   7421
E3A1  .............C....T...................  10692
Con   CTCGTACGACCTGGCCCAGCCCTACGACATCCTGATCGAC
```

Figure 6D

```
E4A  .....................GC..........T..     1049
E1A1 ......................T................   2986
E1A2 .......................T.T                5518
E2A  ...............G.............A            7461
E3A1 ..................T.....                 10732
Con  GGCGGCGCCTACTACGACAACGCCCTGGAAGGCGTGCAGC

E4A  ..........AG....A..................T..    1089
E1A1 ........G...............                  3026
E1A2 ..........A..A..........                  5558
E2A  ........G...............                  7441
E3A1 ........................                 10772
Con  TCAAGATGACCCACGACGTCACCCTGCAGAACGCCGAGAT

E4A  .C...........TC...C.....................  1129
E1A1 ..............G.........                  3066
E1A2 .............TC...C.....C.G......A.G      5598
E2A  ...............A........                  7541
E3A1 ...T.........G..........                 10812
Con  CTACGGCAACGGCCTCTACGGGGTGCGCGTCTACGGCGCC

E4A  ...................................CG     1169
E1A1 ........................                  3126
E1A2 G.......................                  5638
E2A  G....T....................T.C........    7581
E3A1 ...........AC.....T.....                 10852
Con  CAGGACGTGCAGATCCTCGACAACCAGATCCACGACAATT

E4A  .....GCG.C....GTGC....G................T  1209
E1A1 ........................                  3086
E1A2 ..........A.....C.G..............G...T    5675
E2A  ............TT....C..G...A....C.........  7621
E3A1 ........................                 10892
Con  CGCAGAACGGCGCCTATGCCGAAGTCCTGCTGCAGTCCTA

E4A  ......T..........C.........C...A....A.G... 1249
E1A1 ................................T....T.... 3186
E1A2 ........G.---CA...CA....TG.GC.G....AG...   5715
E2A  ......T......................T......A..... 7661
E3A1 .................................T....T... 10932
Con  CGACGACACCGCCGGGGTGTCCGGCAACTTCTACGCCACC
```

Figure 6E

```
E4A  CTGAA....C.......G.......C........            1269
E1A1 ............C...........G............         3206
E1A2 CTGAA....C.............TC.....GA..CT....      5735
E2A  ....................C....GT........           7681
E3A1 ............C...........G................    10952
Con  ACCGGCACCTGGATCGAAGGCAACATCATCAGCGGCTCGG

E4A  ..............................A..........     1329
E1A1 ....T.............................C........   3266
E1A2 A....G...A...T.CGG.G.GC................G      5795
E2A  .............T..........................      7681
E3A1 ....T.......T.....................C........  11012
Con  CCAACTCCACCTACGGCATCCAGGAGCGCGACGACGGCAC

E4A  ................GAT..A....G......C...G...     1369
E1A1 ............................G.....A.......    3306
E1A2 ........C..CG...GTG.A....G.....A....C.GC      5835
E2A  ............................G.G..A..AA....    7781
E3A1 ............T........T.C.....A...C...        11052
Con  CGACTACAGCAGCCTCTACGCCAACAACATCGGCGGTGTG

E4A  ..AC.G---C.CA.C.AA........AC.TC..........     1406
E1A1 ....C...GG..............T..................   3346
E1A2 ...GT..C......G.A...T.C........C.T....GTC    5875
E2A  ..............G..C...C.............CGTC.      7821
E3A1 ........GA.........T................C....   11092
Con  CAGAACGGGTCGGTACGGCTGTACGGCGCCAACTCGACGG

E4A  .A......G.A......G.GACA.C...ACA.C.GTC.AC      1446
E1A1 .....A.....T......GT................------    3380
E1A2 ........GGCA...T.GAA.TG.C....-----------      5904
E2A  .C....A..T..........................-----     7856
E3A1 ......AG......A...G.................-----   11127
Con  TTTCCGGCCAGCCCGGCACCGGCCAGCAGGCGACCXXCXX

E4A  GGGAAGCGACGGCGAGCCA                           1465
E1A1 -------------------
E1A2 -------------------
E2A  -------------------
E3A1 -------------------
Con  X
```

Figure 7A

```
E4A   ..Y..........V...R.S...............        449
E1A1  ..Y..........V.............H........       2386
E1A2  V-...A...........RP.................       4918
E2A   ..Y..........V......................       6861
E3A1  ...........................H........      10132
E3A2  V-...A...........RP..........              12589
Con   MDFNVKDFGALGDGASDDTAAIQAAIDAAYAAGGGTVYLP

E4A   .......AAG..G....ML.DG..LA...........I..    549
E1A1  ....................H.............M...    2546
E1A2  .......PTG..G....ML.DG..LA.D.I.......I..   5078
E2A   ....................H.................    7021
E3A1  ..............A...................M...   10292
Con   AGEYRVSGGEEPSDGCLTIKSNVYIVGAGMGETVIKLVDG

E4A   S..KI................R................     589
E1A1  .T..............................L.A....   2586
E1A2  S..KI..................................   5118
E2A   ...D...I...............................   7061
E3A1  .T..............................L.A....  10332
Con   WDQNVTGMVRSAYGEETSNFGMSDLTLDGNRDNTSGKVDG

E4A   ........G........I....V................    749
E1A1  .......................................   2746
E1A2  ..............N..I.....................   5278
E2A   ......E................................   7221
E3A1  .......................................  10492
Con   WFNGYIPGQDGADRDVTLERVEIREMSGYGFDPHEQTINL

E4A   ................L.DS......A.A.......V     909
E1A1  ........S..............................   2906
E1A2  ................L.DS......A............   5438
E2A   ..................F.I..................   7381
E3A1  .......................................  10652
Con   TIRDSVAHDNGLDGFVADYQVGGVFENNVSYNNDRHGFNI

E4A   ....H...MT........SS.......L....L.SN....    949
E1A1  .............................Y..P......   2946
E1A2  ....Y...MT............TI.........Q.T....   5478
E2A   .............................S.V.......   7421
E3A1  .............................Y..P......  10692
Con   VTSTNDFVLSNNVAYGNGGAGLVVQRGSEDLAHPYDILID
```

Figure 7B

```
E4A   ........R...L....S.I.....D.H...SS.......        1109
E1A1  ..............A........................        3106
E1A2  ............LF...NN............SS...L..T        5638
E2A   .......G.....I..A.......................       7581
E3A1  ........................................      10872
Con   GGAYYDNALEGVQLKMTHDVTLQNAEIYGNGLYGVRVYGA

E4A   .............A.AA.VP..... F.....A..TY...        1269
E1A1  .......................................V.       3266
E1A2 E................T.P.V...AF..SQ-.T.EL.E.        5795
E2A  E.......Y........S...I...................        7741
E3A1 ....L.................................V.       11012
Con   QDVQILDNQIHDNSQNGAYAEVLLQSYDDTAGVSGNFYTT

E4A   LN.R..................N.........ID...A..        1309
E1A1  ....L...V............................S....     3126
E1A2  LN.R....L.DA.D.AN.AVR..D...S..TT.VD...S.G      5658
E2A   ..........V............D............SVSN.     7601
E3A1  ....L...V.......F....................T....    10872
Con   TGTWIEGNTISGSANSTYGIQERADGTDYSSLYANDIDGV

E4A   .-QPIQ...PH.....E..ATP.QPSTGSDGEP              1465
E1A1  .T.A............S.S.......------               3381
E1A2  .VA..Q.S..H.SL..GTVEVP.----------              5904
E2A   ..............V..DL..T.....--------             7856
E3A1  ...T............E..S......--------            11127
Con   QNGSVRLYGANSTVSGQPGSGQQATxxxxxxxx
```

Figure 8A

```
E4R1 ..G.TC...GG....ACGG.....CA.--------------    1478
E1R1 ..........G..CG.........TG.....A....G....    3421
E1R2 GC.ACC..T.....G....G.....AC....T........    3874
E1R3 A....................T..CT...AG........    4351
E1R4 ------..G.GC............GT....GT.....G..    5938
E2R1 ..........G.C..................TG......G..   7896
E2R2 A....G..GGAT.C....G..A..G.C....T...T...T    8349
E2R3 .........G..C..............GC.T..AG.....G.   8814
E2R4 ..G.CG...GG....................TTC.....G.A   9217
E3R1 .............CG..........GT...CA....A..G.  11167
E3R2 G..ACC..T.....G............AC...TC....:..  11620
E3R3 A....G..A...............GCT...AA..G....    12091
Con  CTCGAAGGCACCGACGGCAACGACACGCTGCGCGGCACCG

E4R1 ----------------....AG...GGCT.....GC...T..   1518
E1R1 .....C.........G..................G......   3461
E1R2 .C....GG..A..C.....G...T.C.G..........AC    3914
E1R3 .....A.... CG..........T..A....CGG...AA    4391
E1R4 .T...A....CCA....TA....GGA......G......    5978
E2R1 .C....C...........G.....G.T..A............   7936
E2R2 C...  .C......AT.G........A.............AC   8389
E2R3 CC.. ......GT.-------------------------    8806
E2R4 GC.....C....GAA..GG......GG..T.........A.    9257
E3R1 GT...C......CT.A.T........T...........T...  11207
E3R2 .T....G.G.A..C..... G...T.C.G..........AC   11660
E3R3 G.........ACT..........T.T..G....CGG...A.   12131
Con  AGGCCGACGAGACGCTCCTCGGCCAGGCCGGCAACGACCG

E4R1 ....G.......G......................    1158
E1R1 ...........AT......A......................G   3501
E1R2 ...C........G....................G.T........   3954
E1R3 ..........................................A   4431
E1R4 ....G..............T......C.G.............A   6018
E2R1 .....................A....................    7976
E2R2 G..CG......G..................G.T........   8429
E2R3 ---------------------------A..C.........    8846
E2R4 ....G............A......................G    9297
E3R1 ....G....T....................C...........  11247
E3R2 ...C........G......A..........G..T......   11700
E3R3 ............................TG....G..T.....G  12171
Con  CCTGAACGGCGGCGCCGGCGACGACATCCTCGACGGCGGC
```

Figure 8B

```
E4R1 ............CGG....G.....................    1598
E1R1 ..A..........A............................    3541
E1R2 .............G..................C..G..G...G  3994
E1R3 ..G..............................A....G....  4471
E1R4 ..G.........GA...................A....T....  6058
E2R1 .............A..............................C 8016
E2R2 .............G...C..............C..A..G...G  8469
E2R3 .G...........G...G....A..G..C..G......G     8886
E2R4 ..G..................GT......AGC...AG.....   9337
E3R1 ..G.........T........................T.      11287
E3R2 .................................C..G..G...G 11740
E3R3 ..G.A............................A....G.....  12211
Con  GCCGGGCGCGACACCCTGACCGGCGGCGCGGGCGCCGACA

E4R1 .....GTG........C..CGAG.............T.....    1638
E1R1 ...................C........................    3581
E1R2 TG.........GA.....T.T........C.G....A.T.      4034
E1R3 ......TG......A....T.........................  4511
E1R4 .....GTG...G......T.....T....................  6098
E2R1 TG......G.........C..........................  8056
E2R2 TG.........GA.....T.T........C.G....A.T.      8509
E2R3 TG........TAG..AA.T.................A---..    8923
E2R4 T..........GG..GCGC.CT........T.....A.T.      9377
E3R1 ..............T..C..CGAG.....TC............    11327
E3R2 TG.........GAG....T.T........C.G....A.T.      11780
E3R3 ......TG..........T..........................  12251
Con  CCTTCCGCTTCTCCGCGCGGACCGACAGCTACCGCACCGA

E4R1 ..CG..G------GTG................CT.......    1672
E1R1 .......------...........................    3615
E1R2 ..C.A.........A.CAGGC.....GC..TCT.......    4074
E1R3 .......------............................    4545
E1R4 .GCG.GG------GTG................CT.......    6132
E2R1 .......------............................    8090
E2R2 .GA.AT........A.CAGGG.....GC...G........    8549
E2R3 ...T...------..C.ATGC...T........T......    8957
E2R4 .GC.AG...GACG.A.GG..C....AGC.............    9417
E3R1 .......------ ......C....................    11361
E3R2 ..C...........A.CAGGG...TTAC....T.......    11820
E3R3 .......------........C...................    12285
Con  CAGCGCCGGCGACAGCTTCAACGACCTGATCACCGACTTC
```

Figure 8C

```
E4R1 ..G...... ....T........................    1712
E1R1 ......GA. .....A.......................    3655
E1R2 ...C.G.C.CT....A.G......G....G.........    4114
E1R3 ..TC...C.C....................GC.......    4585
E1R4 ..............................C.....T..    6172
E2R1 .........C..............................    8130
E2R2 .CG.TGG....A...AAGC.....G.A..G..........    8589
E2R3 ..T..........T..T..............GC...C...    8997
E2R4 AC.C...G......T.TG........C....T...C....    9457
E3R1 .........C..............C..............   11401
E3R2 .C..TGG....A...A.G......G.A..G........T.   11860
E3R3 ..TC..GC.C....T...............GC........   12325
Con  GACGCCAGCGAGGACCGCATCGACCTGTCCGCGCTGGGCT

E4R1 .TT....C..............TGG............C..    1752
E1R1 .......C.................T..............    3695
E1R2 ............A.....CG............CGCCG..    4154
E1R3 ...G...TT.C...A........G................    4625
E1R4 ...G...CT.C...........................G.    6212
E2R1 .....................T..................    8170
E2R2 ..............................CGCC..      8629
E2R3 ...G...T......A........GG...T......GC...    9037
E2R4 A............................T......GC.A.   9497
E3R1 .......T......A....T..TG..........GC.G.   11441
E3R2 A...........A.....CG............CGCCG.   11900
E3R3 ...G...TT.C...A........G................   12365
Con  TCACCGGGCTGGGCGACGGCTACAACGGCACCCTGCTGCT

E4R1 .A..AC........AG.....G..............A...    1792
E1R1 .A..AC........AG..T..G..................    3735
E1R2 .GT.......AG.......GA.......G.T.........    4194
E1R3 ....G.........G........................T    4665
E1R4 ........G.AG......A.....T........C.....    6252
E2R1 ....G...G.....A.....G.........T.........    8210
E2R2 .GT.......AG.......GA.......G....A...    8669
E2R3 ....G.G...AG.....T......................    9077
E2R4 AGT...G....A.........AAG............A.A.    9537
E3R1 .ACCAC.GGTT...G..........................   11481
E3R2 .GT.......AG.......GA.......G...........   11940
E3R3 ....G.........G..........................   12405
Con  GGTGCTCAACGCCGCCGGCACCCGCACCTACCTGAAGAGC
```

Figure 8D

```
E4R1 .T.........T.........A.G...........G......      1832
E1R1 .....A..........C......G..................      3775
E1R2 .....CA.C......A.C...T.CA........C.TT...        4234
E1R3 .T......C..T...A.C......................        4705
E1R4 .......A....CT........G...........G......       6292
E2R1 CTG........T........G.G...T..............       8250
E2R2 .....AAC.G......C...T.C.........T.TT...         8709
E2R3 .T....A.CA......CC...G....T..............       9117
E2R4 CG....AGC........A...A.C.AG..............       9577
E3R1 .......T.....C......G...T.....A........        11521
E3R2 .....CA.T......A.C...T.TAA.......C.TT...       11980
E3R3 CT......C..T.....C......................       12445
Con  TACGAGGCGGACGCCGAGGGCCAGCGCTTCGAGATCGCCC

E4R1 ........G..C....G...G.T..TTC......C...TG.       1892
E1R1 ............T......T.T.T..AA..A.A.....C.        3835
E1R2 .C.CG.........CAG..G......A........GC.G..       4294
E1R3 ........G...T..G......AT.G.A.AG..G....G.        4765
E1R4 ........G..C....G...G.T..TTC......C...TG.       6352
E2R1 ............T.G......T.......T....G....C.       8310
E2R2 .C...........TCTG.AG.TA......AA...GG.T...       8769
E2R3 ........G..CTGT...CG.TCGG...G...A..CTGA.        9177
E2R4 ....G......C..G...A........AT..GAG.G....       9637
E3R1 ............T.GT.......T...AA..AT.G....C.      11581
E3R2 .C.CG.........CAG..G.T.............AC.G..      12040
E3R3 ........G...T..G.......T.G.A.AG..G....G.       12425
Con  TGGACGGCAACTACACCGGCCAGCTCGGCGCCGACAACTT

E4R1 .............A...G.                             1891
E1R1 .T.G....A...C..TC..                             3834
E1R2 C..T......GA..T.TCA.                            4293
E1R3 .A......AGC.C...---                             4761
E1R4 ...T.......AC.A..GC                             6351
E2R1 .C     AGCGCA....C                              8309
E2R2 CA........A...C..AGC                            8768
E2R3 CC..GA...GCGTA...TA                             9176
E2R4 CA........A....G..C                             9635
E3R1 .T.G....A...C..TC..                            11580
E3R2 C.........A...C..C..                           12039
E3R3 .A......AG..C.G.---                            12501
Con  GGTCTTCGCCGCGGCCGCG
```

Figure 9A

```
E4R1 .V.G.TD.Q---------.Q.GS.A...D............      1600
E1R1 ...SA...A....E........Q..D.....D..N......      3541
E1R2 AT..E.S.N.L....G.....YG...T..........V..       3994
E1R3 I.........Q..E.N.R....D.R.N.............      4471
E1R4 --.....V.V.S..NDQ.Y.G..D...D.....L....       6058
E2R1 ....A.....G.S.........D........N........      8016
E2R2 I..DA.DNA.L...S.A.....H....T.D........V..      8469
E2R3 ...SA...S.Q..A.D.V-----------------IH..      8886
E2R4 .A.G........SS.A.E...GV...S.D....N.....      9336
E3R1 ....A...V....G...LI.........D......T....     11287
E3R2 VT..E...N......G.....YG...T......N...V..     11740
E3R3 I.......S.Q..G.D.L....GGR.S........V....     12211
Con  LEGTDGNDTLSGTDAHETLLGLAGNDRLNGGAGDDILDGG

E4R1 ....R.S........V....E......T.--V.....L..      1694
E1R1 ....N.......................--.........      3695
E1R2 ....S........V...D.LS..Q.NYTT..NQA.R.L..      4154
E1R3 .........T.....L..T............--........     4625
E1R4 ....D....T.....V.A.........AG--V.....L..      6212
E2R1 ....N........L..V...............--........    8070
E2R2 ....S........V...D.LS..Q.NYDI..NQG.R.A..      8639
E2R3 G.....A......V....EL.....-...--.YA......      9037
E2R4 ......S..S.S.I...GGAL..F.NYAS.TNGT.S....      9496
E3R1 ..............E..H......--..T......     11441
E3R2 .............V...E.LS..Q.NYT...NQG.Y.I..     11900
E3R3 .E.......T.....L...........--..T......     12365
Con  AGRDTLTGGAGADTFRFSARTDSYRTDSAGDSFNDLITDF

E4R1 E...............S......G.....KT.AE........      1734
E1R1 ..D..S....................KT.AE........      3735
E1R2 .PTL....V.........N.R....AVV.....D..D...      4194
E1R3 .PTQ......G...S.F.N..D......V.A.........      4665
E1R4 ..............S.F.........V...S...........     6252
E2R1 ...Q........................VSAD.S......      8110
E2R2 AVG..KL.V................A.V.....D...V..      8669
E2R3 .........G...S...N..G....A..V...........     9077
E2R4 TPG..L....V..Y............AIV..D...K....N      9536
E3R1 ...Q.............N..D...AVTTG.G........     11481
E3R2 AVG......V....Y....N.R....AVV.....D...V..     11940
E3R3 .PAQ......G...S.F.N..D......V.A.........     12405
Con  DASEDRIDLSALGFTGLGDGYNGTLLLQLNSAGTRTYLKS
```

Figure 9B

```
E4R1 F..........V....DH..D.S.A.V...A.G           1891
E1R1 .....Q...............FNDN.LL.DAA.           3834
E1R2 .DT..N.YS..LS.A..YQ.Q.S..Q.....SQ            4293
E1R3 F....N.Q........D.S.Q.DSG.VI.EPA-            4761
E1R4 ..E.L......V....DH..D.S.A.V...DDG            6351
E2R1 L................A.....G.LL.ER.A             8309
E2R2 ..NG.D.Y...FS....YLE...N.D.I...PS            8768
E2R3 F.TN.A.E........DLSA.G..NLILD.R.V            9176
E2R4 R.S....NQ.....E..HADQ.D.SD.I...AA            9635
E3R1 ...V..Q...........V.QFNDG.LL.DAA.           11580
E3R2 .DT..N.TN..LS.A..TQ......Q.....P.           12039
E3R3 L....D.Q........D.S.Q.DSG.VI.EAG-           12502
Con  YEADAEGRRFEIALDGNFTGLLGAENFVFATTP
```

Figure 11A

```
  1  GCCAGTCTCA GGCACAGCAG CGCGCGAGCC GCTTCGCTTT

41  GTCCGCCCCC CGCTTTTCTC GCTGAACGCG ACGATCGCCG

81  GGCGCCGGGG AAGGGTTCGC GCATGCCGAG CCGGGGACGG

121  GAAAAGCCTG TTCGACCAGT CGACTCTTCC TCCCTTCACT

161  TTCCAGGCAG CCTGCGGGCT GCGCAGTAAC GGAACAGGAA
             *  *      *  *  *    *  *  *  *    *  *  *
               M  D   Y  N  V    K  D  F   A  L  G
201  GCAGCATGGA TTACAACGTC AAAGATTTCG GGCGCTGGG
     ‾‾
     *  *  *   *  *  *  *
       D  G  V   S  D  D  T    A  A  I    Q  A  A
241  CGATGGCGTC AGCGACGATA CGGCCGCCAT CCAGGCGGCG

I  D  A  A    Y  A  A    G  G  G    T  V  Y  L
281  ATCGATGCCG CCTACGCGGC CGGCGGCGGC ACCGTCTACC

P  A  G    E  Y  R    V  S  G  G    E  E  P
321  TGCCGGCCGG CGAATACCGG GTCAGCGGCG GCGAGGAGCC

S  D  G    C  L  T  I    K  S  N    V  H  I
361  TTCCGATGGT TGCCTGACCA TCAAGAGCAA CGTCCATATC

V  G  A  G    M  G  E    T  V  I    K  L  V  D
401  GTCGGCGCGG GGATGGGCGA GACGGTCATC AAGCTGGTCG

G  W  D    Q  D  V    T  G  I  V    R  S  A
441  ACGGCTGGGA TCAGGACGTC ACCGGCATCG TCCGCTCGGC

Y  G  E    E  T  S  N    F  G  M    S  D  L
481  CTACGGCGAG GAGACCAGCA ACTTCGGCAT GAGCGACCTG

T  L  D  G    N  R  D    N  T  S    G  K  V  D
521  ACCCTCGACG GCAACCGCGA CAACACCAGC GGCAAGGTCG

G  W  F    N  G  Y    I  P  G  E    D  G  A
561  ACGGCTGGTT CAACGGCTAC ATTCCCGGCG AGGACGGCGC

D  R  D    V  T  L  E    R  V  E    I  R  E
601  CGACCGCGAC GTGACCCTGG AGCGGGTGGA AATCCGTGAA

M  S  G  Y    G  F  D    P  H  E    Q  T  I  N
641  ATGTCCGGTT ACGGTTTCGA TCCGCACGAG CAGACCATCA
```

Figure 11B

```
          L   T   I       R   D   S   V       A   H   D       N   G   L
681     ACCTGACGAT      CCGCGACAGC      GTGGCCCACG      ACAACGGCCT

D   G   F       V   A   D   F       Q   I   G       G   V   F
721     CGACGGCTTC      GTCGCCGATT      TCCAGATCGG      CGGGGTGTTC

E   N   N   V       S   V   N       N   D   R       H   G   F   N
761     GAGAACAACG      TCTCGTACAA      CAACGACCGC      CACGGCTTCA

I   V   T       S   T   N       D   F   V       L   S   N   N
801     ACATCGTCAC      CAGCACCAAC      GACTTCGTCC      TGAGCAACAA

V   A   Y       G   N   G   G       A   G   L       V   V   Q
841     CGTCGCCTAC      GGCAACGGCG      GCGCCGGCCT      GGTGGTGCAG

R   G   S   S       D   V   A       H   P   Y       D   I   L   I
881     CGCGGCTCGT      CCGACGTGGC      GCACCCCTAC      GACATCCTGA

D   G   G       A   Y   Y       D   N   G   L       E   G   V
921     TCGACGGCGG      CGCCTACTAC      GACAACGGCC      TGGAAGGCGT

Q   I   K       M   A   H   D       V   T   L       Q   N   A
961     GCAGATCAAG      ATGGCCCACG      ACGTCACCCT      GCAGAACGCC

E   I   Y   G       N   G   L       Y   G   V       R   V   Y   G
1001    GAGATCTACG      GCAACGGCCT      ATACGGGGTG      CGCGTCTACG

A   E   D       V   Q   I       L   D   N   Y       I   H   D
1041    GCGCCGAGGA      TGTGCAGATC      CTCGACAACT      ACATCCACGA

N   S   Q       N   G   S   Y       A   E   I       L   L   Q
1081    CAATTCGCAG      AACGGTTCCT      ACGCGGAAAT      CCTCCTGCAG

S   Y   D   D       T   A   G       V   S   G       N   F   Y   T
1121    TCCTACGACG      ATACCGCCGG      GGTGTCCGGC      AATTTCTACA

T   T   G       T   W   I       E   G   N   T       I   V   G
1161    CCACCACCGG      CACCTGGATC      GAAGGCAACA      CCATCGTCGG

S   A   N       S   T   Y   G       I   Q   E       R   D   D
1201    CTCGGCCAAC      TCCACCTATG      GCATCCAGGA      GCGCGACGAC

G   T   D   Y       S   S   L       Y   A   N       S   V   S   N
1241    GGCACCGACT      ACAGCAGCCT      CTACGCCAAC      AGCGTCAGCA
```

Figure 11C

```
       V   Q   N    G   S   V    R   L   Y    G   A   N   S
1281 ATGTGCAGAA CGGCTCGGTG CGCCTCTACG GCGCCAACTC

V   V   S   D    L   P   G    T   G   Q    Q   A   T
1321 CGTCGTCTCC GACCTGCCCG GCACCGGCCA GCAGGCGACC
     REP1
       L   E   G   T    A   G   N    D   T    L   G   G   S   D
1361 CTCGAAGGCA CGGCCGGCAA CGACACGCTT GGCGGCAGCG

A   H   E   T    L   L    G   L   D    G   N   D   R
1401 ACGCCCACGA GACGCTGCTC GGGCTGGACG GCAACGACCG

L   N   G    G   A   G   N    D   I    L    D   G   G
1441 CCTGAACGGC GGCGCCGGCA ACGACATCCT CGACGGCGGC

A   G   R   D    N   L   T    G   G   A    G   A   D   L
1481 GCCGGGCGCG ACAACCTGAC CGGCGGCGCG GGCGCCGACC

F   R   V    S   A   R   T    D   S   Y    R   T   D
1521 TGTTCCGCGT CTCCGCGCGC ACCGACAGCT ACCGCACCGA

S   A   S    F   N   D   L    I   T   D    F   D   A
1561 CAGCGCCAGC TTCAACGACC TCATCACCGA CTTCGACGCC

S   Q   D   R    I   D   L    S   A   L    G   F   T   G
1601 AGCCAGGACC GCATCGACCT GTCCGCGCTG GGCTTCACCG

L   G   D    G   Y   N    G   T   L   L    L   Q   V
1641 GGCTGGGCGA CGGCTATAAC GGCACCCTGC TGCTGCAGGT

S   A   D    G   S   R   T    Y   L   K    S   L   E
1681 CAGCGCCGAC GGCAGCCGCA CCTATCTGAA GAGCCTGGAG

A   D   A   E    G   R   R    F   E   I    A   L   D   G
1721 GCGGATGCCG AGGGGCGGCG TTTCGAGATC GCCCTGGACG

N   F   A    G   L   L    G   A   G   N    L   L   F
1761 GCAACTTCGC CGGCCTGCTC GGTGCCGGCA ACCTGCTCTT
                                REP2
       E   R   T    A   I   E   G    D   A   G    D   N   A
1801 CGAGCGCACC GCCATCGAGG GGGATGCCGG CGACAACGCC

L   L   G   T    S   A   A   E    T   L    L   G   H   A
1841 CTGCTCGGTA CCTCGGCCGC CGAGACATTG CTCGGCCACG
```

Figure 11D

```
          G   N   D   T   L   D   G   G   A   G   D   D   I
1881 CCGGCAACGA CACGCTCGAC GGCGGGGCCG GCGACGACAT

L   V   G   G   A   G   R   D   S   L   T   G   G
1921 CCTGGTCGGC GGCGCCGGGC GCGACAGCCT CACCGGCGGC

A   G   A   D   V   F   R   F   D   A   L   S   D   S
1961 GCCGGAGCGG ACGTGTTCCG CTTCGACGCG CTGTCCGACA

Q   R   N   Y   D   I   G   D   N   Q   G   D   R
2001 GCCAGCGCAA CTACGACATC GGCGACAACC AGGGCGACCG

I   A   D   F   A   V   G   E   D   K   L   D   V
2041 CATCGCCGAC TTCGCGGTGG GCGAAGACAA GCTCGACGTA

S   A   L   G   F   T   G   L   G   D   G   V   N   G
2081 TCGGCGCTGG GCTTCACCGG GCTGGGCGAC GGCTACAACG

T   L   A   L   V   L   N   S   A   G   D   R   T
2121 GCACCCTCGC CCTGGTGCTC AACAGCGCCG GCGACCGCAC

Y   V   K   S   Y   E   N   G   A   D   G   Y   R
2161 CTACGTGAAA AGCTACGAGA ACGGCGCCGA CGGCTACCGC

F   E   F   S   L   D   G   N   Y   L   E   L   L   G
2201 TTCGAGTTTT CCCTCGACGG CAACTATCTG GAGCTACTCG

N   E   D   F   I   F   A   T   P   S   G   Q   Q
2241 GCAACGAGGA TTTCATCTTC GCCACGCCCA GCGGCCAGCA
          REP3
          L   L   E   G   C   A   G   M   D   S   L   Q   G
2281 ACTCCTCGAA GGCAGCGCCG GCAACGACAG CCTGCAGGGC

T   A   A   D   E   V   I   H   G   G   G   G   R   D
2321 ACGGCCGCCG ACGAGGTGAT CCACGGCGGC GGCGGGCGCG

T   L   A   G   G   A   G   A   D   V   F   R   F
2361 ACACGCTGGC CGGAGGGCC GGGGCCGACG TGTTCCGCTT

S   E   L   T   D   S   Y   R   D   S   A   S   Y
2401 TAGCGAACTG ACCGACAGCT ACCGAGACAG TGCCAGCTAT

A   D   L   I   T   D   F   D   A   S   E   D   R   I
2441 GCCGATCTGA TCACTGACTT CGATGCCAGC GAGGATCGTA
```

Figure 11E

```
        D  L  S     G  L  G     F  S  G  L     G  N  G
2481 TCGACCTGTC CGGCCTCGGC TTCAGCGGTC TGGGCAACGG

Y  G  G     T  L  A  L     Q  V  N     S  A  G
2521 CTACGGCGGT ACCCTGGCGC TGCAGGTGAA CAGCGCCGGT

T  R  T  Y     L  K  S     F  E  T     N  A  A  G
2561 ACCCGCACCT ACCTGAAGAG CTTCGAGACC AACGCCGCCG

E  R  F     E  I  A     L  D  G  D     L  S  A
2601 GCGAGCGTTT CGAGATCGCC CTGGACGGCG ACCTGTCCGC

L  G  G     A  N  L  I     L  D  A     R  T  V
2641 GCTCGGCGGG GCCAACCTGA TCCTCGACGC GCGTACCGTA
     REP4
     L  A  G  G     D  G  N     D  T  L     S  G  S  S
2681 CTGGCGGGCG GCGACGGCAA CGACACGCTT TCCGGCAGCA

A  A  E     E  L  L     G  G  V  G     N  D  S
2721 GCGCGGCCGA GGAACTGCTC GGCGGGGTCG GCAACGACAG

L  D  G     G  A  G  N     D  I  L     D  G  G
2761 CCTGGACGGC GGCGCCGGCA ACGACATCCT CGACGGCGGG

A  G  R  D     T  L  S     G  G  S     G  S  D  I
2801 GCGGGGCGCG ACACCCTGAG TGGCGGCAGC GGCAGCGACA

F  R  F     G  G  A     L  D  S  F     R  N  Y
2841 TCTTCCGCTT CGGCGGCGCG CTCGACAGCT TCCGCAACTA

A  S  G     T  N  G  T     D  S  I     T  D  F
2881 CGCCAGCGGG ACGAACGGCA CCGACAGCAT CACCGACTTC

T  P  G  E     D  L  I     D  L  S     V  L  G  Y
2921 ACCCCCGGCG AGGATCTGAT CGACCTCTCC GTGCTCGGCT

T  G  L     G  D  G     Y  N  G  T     L  A  I
2961 ACACCGGGCT GGGCGACGGC TACAACGGTA CCCTGGCGAT

V  L  N     D  A  G  T     K  T  Y     L  K  N
3001 AGTGCTGAAC GACGCCGGCA CCAAGACCTA CCTGAAAAAC

R  E  S  D     A  E  G     N  Q  F     E  I  A  L
3041 CGCGAGAGCG ACGCCGAAGG CAACCAGTTC GAGATCGCCC
```

Figure 11F

```
          E   G   N      H   A   D      Q   L   D      A   S   D   F
3081 TGGAGGGCAA CCACGCCGAC CAGCTCGATG CGAGCGACTT

I   F   A      T   A   A   A      T   T   G      I   E   V
3121 CATCTTCGCC ACGGCGGCCG CGACCACCGG AATCGAGGTG

V   G   G   S      G   T   Q      T   D   Q      L   A   <
3161 GTCGGCGGCA GCGGCACCCA GACCGATCAG CTCGCCTGAT

3201 CCGACCCCGC CCGCACCCGC CCGGCCATTC CGGCCGGGCG

3241 AACCAATGGC CTTTTGATCA
```

DNA COMPOUNDS COMPRISING SEQUENCES ENCODING MANNURONAN C-5-EPIMERASE

The present invention concerns DNA compounds encompassing sequences coding for enzymes having mannuronan C-5-epimerase activity, a process for the preparation of such enzymes, the use of said genetic sequences in production of alginates having a definite G/M ratio and block structure, and the production of alginates having a definite G/M ratio by inactivating said genetic sequences.

Throughout this application, reference is made to publications from the scientific and patent literature. Publications so cited are hereby incorporated in their entirety by reference.

In this application the term gene is used to indicate a genetic sequence which encodes a protein, independent of whether the protein encoded by this genetic sequence is expressed or not in the natural host organism under those conditions.

Alginates are a family of polysaccharides, which are synthesized in brown algae as well as in bacteria, such as *Azotobacter vinelandii* and *Azotobacter chroococcum*. Alginates are also synthesized by some strains of Pseudomonas sp.

Chemically, alginates are unbranched binary copolymers of 1–4 linked β-D-mannuronic acid, termed M, and its C-5 epimer α-L-guluronic acid, termed G.

Alginates derived from seaweeds and Azotobacter are generally true block copolymers where the monomers are arranged in homopolymeric stretches of M, termed M blocks, and homopolymeric stretches of G, termed G blocks, interspaced with regions containing both monomers, normally termed alternating blocks or MG blocks. The composition and sequential structure of alginates vary widely depending on the source. Alginates produced by Pseudomonas, however, do not have any G blocks.

Several functional properties such as the capacity to form gels and the binding of water depend on the M/G ratio and on the length of the various blocks. A relatively high content of G blocks, for instance gives good gelling properties, due to ionic cross linking of chains which takes place when $Ca^{2+}$-ions are added to an alginate solution. The composition and block structure also influence on the immunological properties of alginates. [Otterlei et al, J. of Immunotherapy 10, 286–291, (1991)] have shown that alginates with a high content of mannuronic acid blocks are very potent nontoxic immunostimulants.

At present industrial production of alginates rely exclusively on algal sources. The range in composition is however limited as the highest content of guluronic acid to be found is 75% and the lowest 25%. Furthermore there are no suitable sources for alginate with a G content in the range of 42–54%. In the field of biotechnology or biomedicine, polymers with extreme compositions, such as a high G for immobilization of cells, [Martinsen A., Skjåk-Bræk G. and Smidsrød O., Biotechnol. Bioeng. 33, 79–86, (1989)] and a high M (90–100%) as immunostimulants [Otterlei et al, J. of Immunotherapy 10, 286–291, (1991)] are of major interest.

The key enzyme responsible for generation of the G blocks is called mannuronan C-5-epimerase. It was previously thought that only one enzyme having a certain amino acid sequence would exhibit this activity. It has now surprisingly been found that there exist at least five genes encoding enzymes having this activity. Some of these enzymes differ in molecular weight and amino acid sequence. The genes were found adjacent to each other in the bacterium *Azotobacter vinelandii*. It has also been found that the amino acid sequence of the enzyme affects the activity of the enzyme, not only in terms of potency but also in the type of alginate formed, for example, altering the content of guluronic acid and the single/block G content of the alginate.

In [Larsen, B. and Haug, A., Carbohydr. Res. 17, (1971), 287–296 and 297–308] the isolation of mannuronan C-5-epimerase from liquid cultures of *Azotobacter vinelandii* is reported. In the following, this epimerase will be termed mannuronan C-5-epimerase (2), and the DNA sequence encoding for it will correspondingly be denominated E2.

In [Skjåk-Bræk, G and Larsen, B, Carbohydr. Res. 103:133–136, (1982)], the purification of mannuronan C-5-epimerase (2) by affinity chromatography on alginate sepharose is disclosed. In a separate paper [Skjåk-Bræk, G and Larsen, B., Carbohydrate Research, 139, (1985) 273–283] the characterization of this enzyme is disclosed. Further, the activity of the enzyme is described as an ability to epimerize both bacterial and algal alginate having a wide range in monomer composition and sequence of units.

From PCT/WO 86/03781 and Japanese Patent Application J63233797 it is known to produce alginic acid and/or alginate having a high content of guluronic acid by action of the enzyme (E2) on an alginic acid or alginate, whereby the G content increases.

In [Chitnis, C. E. and Ohman, D. E., J. Bacteriol., 172, p2894–2900, (1990)] the gene sequences involved in the introduction of guluronic acid into exopolysaccharides from *Pseudomonas aeruginosa* have been reported. However, the nature of the enzyme responsible for this process has not been identified. Since this genus of bacteria is unable to produce alginate containing G blocks [Skjåk-Bræk, G., Larsen, B. and Grasdalen, H. Carbohydr. Res. 54 (1986) 169–174] it is believed that the epimerization system in alginate producing Pseudomonas is fundamentally different from the epimerase in brown algae and in *Azotobacter vinelandii*. It seems likely that the Pseudomonas enzyme is a monomer epimerase acting at the sugar nucleotide level, and as such is unable to introduce G-blocks into already polymerized alginates.

Production of mannuronan C-5-epimerase from *Azotobacter vinelandii* culture is difficult due to a very low yield. It is also a major obstacle that the enzyme is secreted together with copious amounts of highly viscous alginate which hampers the purification of the enzyme. Although alginates are secreted by some bacteria, an industrial production based on these microorganisms has not been successful. The main reasons are due to the difficulties in controlling the composition and molecular size of the exopolysaccharides. The content of guluronic acid blocks in the alginate from *Azotobacter vinelandii* tends to be too low for making a polymer with good gelling properties.

Alginates with a high M content having immunogenic properties as reported above, are produced by *Pseudomonas aeruginosa*, but this organism is unattractive from a production point of view, as it is unstable in the production of the polymer. Further, the organism is known to be a secondary pathogen in patients suffering from cystic fibrosis.

Thus, in order to produce medical grade alginates with a defined monomer composition and sequential structure there is a need for improved methods for controlling the biosynthesis of alginate, through controlling the key enzyme, the mannuronan C-5-epimerase.

The present invention is directed to cloned DNA fragments encoding mannuronan C-5-epimerase. The invention is encompassed by vectors which contain DNA fragments encoding mannuronan C-5-epimerase linked to DNA elements which direct the expression of mannuronan C-5-epimerase from the cloned DNA encoding the protein. The invention also provides for microorganisms which express the mannuronan C-5-epimerase protein from the cloned DNA as a source of the purified protein and also as a source of alginates of altered composition. Strains in which the expression level of the mannuronan C-5-epimerase gene is altered or in which one, several or all of the mannuronan C-5-epimerase genes have been inactivated are also within the scope of the present invention. The invention further encompasses methods for producing alginates either very efficiently, or having altered composition, or both, by culturing microorganisms having altered levels of expression of a mannuronan C-5-epimerase gene.

The invention further features selection of epimerase to achieve a desired level of guluronic acid, and alter the single/block G characteristics of the enzyme. In a further embodiment, the invention features the production of synthetic proteins and DNA encoding such proteins which have mannuronan C-5-epimerase activity.

BRIEF DESCRIPTION OF FIGURES

FIG. 1 shows the amino acid sequence SEQ ID NO:6 of the N-terminal end of the 122 kd protein, and the nucleotide sequence of the corresponding oligonucleotide SEQ ID NO:16. The DNA probe was synthesized as a mixture (in equal ratios) of the 64 possible combinations that could be deduced from the first seven amino acids in the sequence of the 122 kd protein. N indicates that all four bases were used at this position.

FIG. 2 is a restriction endonuclease map of the combined inserts in plasmids pHE14, pHE16, pBD1, pHE18 and PML1.

The numbers at the bottom line indicate the molecular sizes in bp. The arrow indicates the localization and orientation of the sequence homologous to the synthetic oligonucleotide used for screening the library. The five genes (open reading frames) found by sequencing are marked by boxes and denoted E4, E1, E2, E3 and E5. E1 corresponds to Epimerase I.

Figure 3:
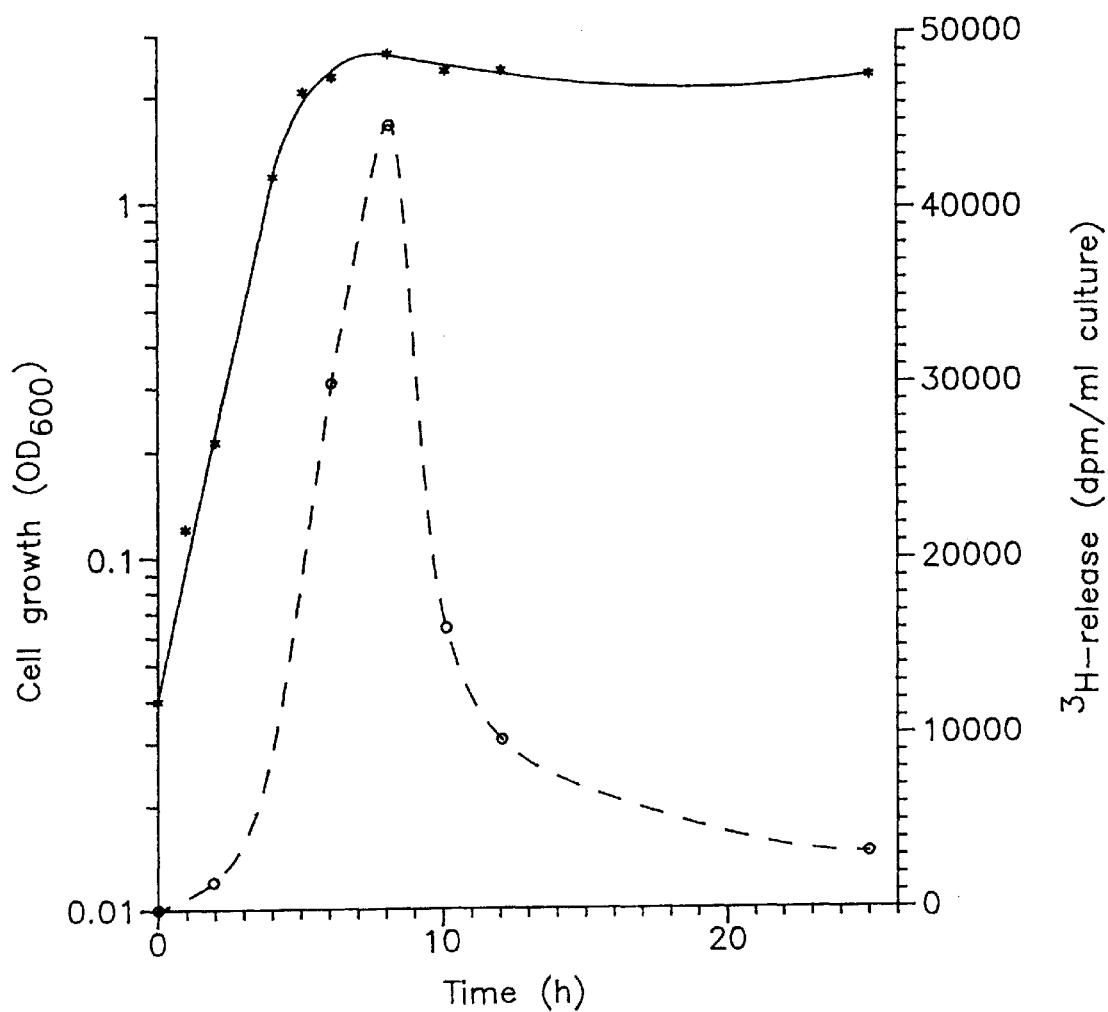

FIG. 3 shows Mannuronan C-5-epimerase (1) activity of a portion of the E1 encoded protein as a function of cell growth. *: $OD_{600}$ of cell culture. o: Epimerase activity given as dpm/ml of cell culture. The strain used in this experiment was DH5α(pHE5), and the extracts were incubated with the substrate for 23 hours.

Figure 4:
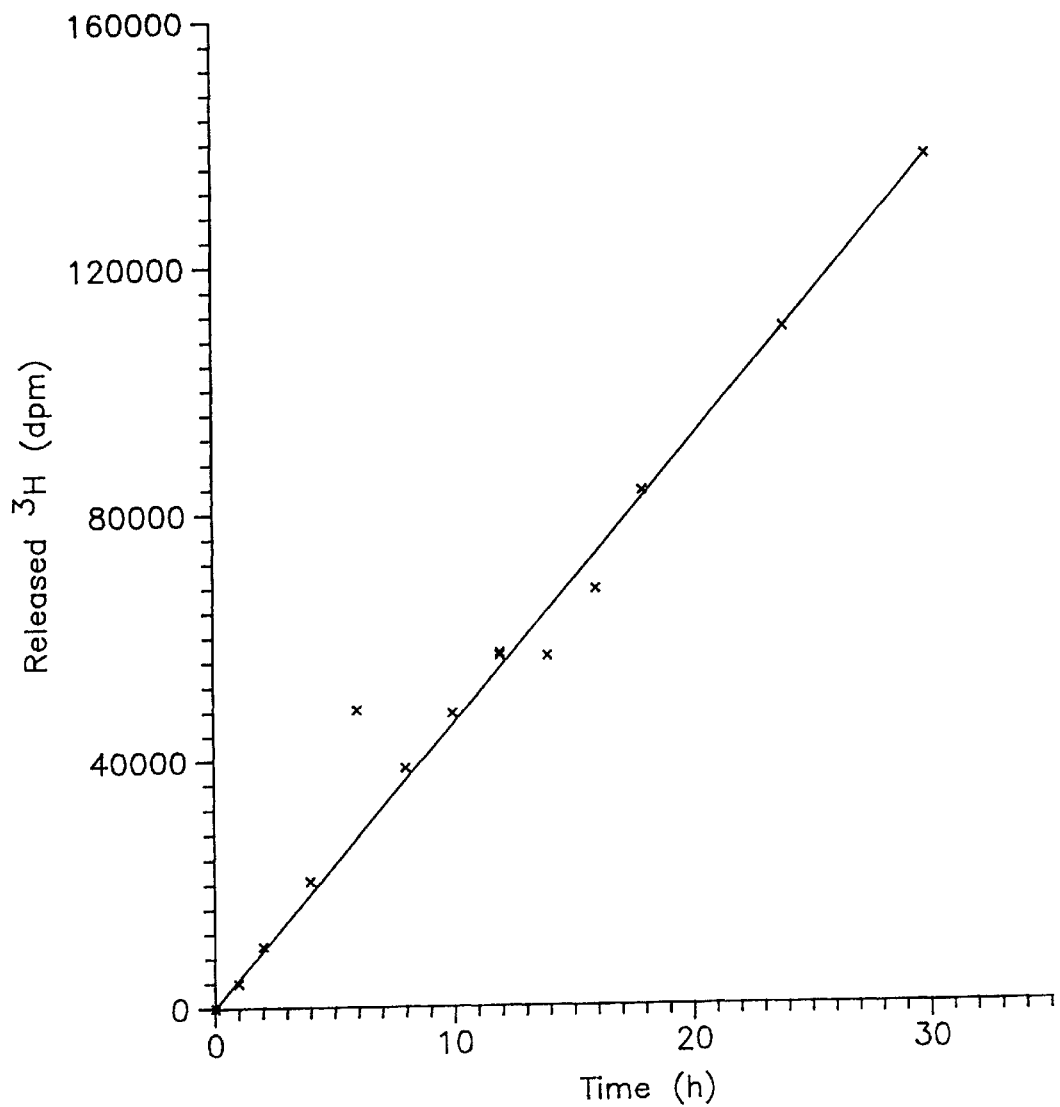

FIG. 4 shows the kinetics of $^3H$ release. The enzyme activity was assayed by using an extract prepared from IPTG-induced JM105 cells containing pHE5 (see legend to Table 3).

Figure 5:
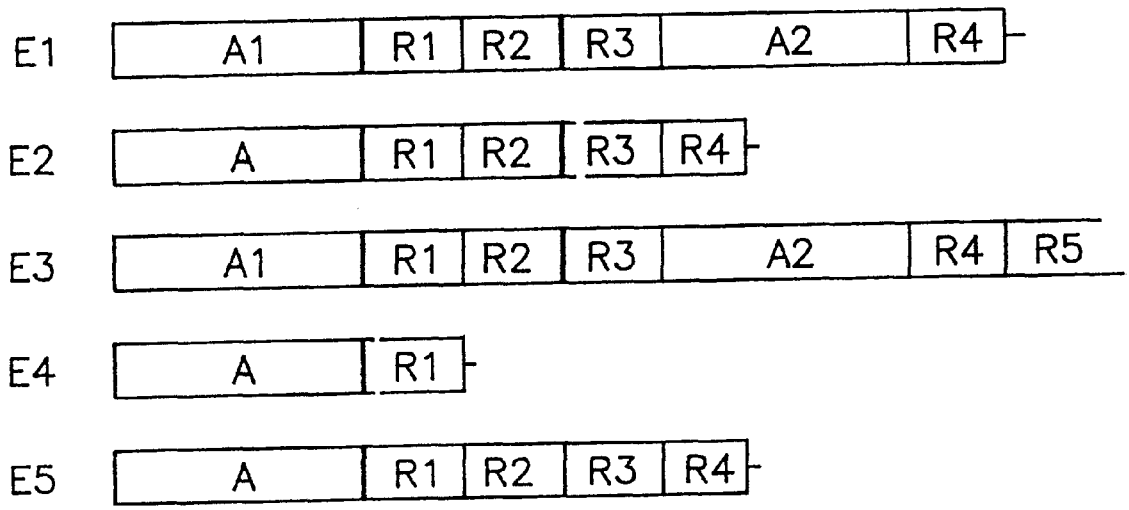

FIG. 5 shows the homologies between and within the different genes. Boxes with the same letter are homologous to each other. Gaps are introduced to optimize the alignment. E1–E4 are defined as appears from FIGS. 2 and 6.

FIGS. 6A–6E (SEQ ID NO:7) shows the alignment of the DNA sequences of the A blocks from E4, E1, E2 and E3 SEQ ID NO:7=Con, SEQ ID NO:17=E4A, SEQ ID NO:18=E1A1, SEQ ID NO:19=E1A2, SEQ ID NO:20=E2A, SEQ ID NO:21=E3A1, SEQ ID NO:22=E3A2.

FIG. 7A–7B (SEQ ID NO:8) shows the alignment of the deduced amino acid sequences of the A blocks from E4, E1, E2 and E3 SEQ ID NO:8=Con, SEQ ID NO:23=E4A, SEQ ID NO:24=E1A1, SEQ ID NO:25=E1A2, SEQ ID NO:26=E2A, SEQ ID NO:27=E3A1, SEQ ID NO:28=E3A2.

FIGS. 8A–8D (SEQ ID NO:9) shows the alignment of the DNA sequences of the R blocks from E4, E1, E2 and E3 SEQ ID NO:9=Con, SEQ ID NO:29=E4R1, SEQ ID NO:30=E1R1, SEQ ID NO:31=E1R2, SEQ ID NO:32=E1R3, SEQ ID NO:33=E1R4, SEQ ID NO:34=E2R1, SEQ ID NO:35=E2R2, SEQ ID NO:36=E2R3, SEQ ID NO:37=E2R4, SEQ ID NO:38=E3R1, SEQ ID NO:39=E3R2, SEQ ID NO:40=E3R3.

FIG. 9A–9B (SEQ ID NO:10) shows the alignment of the deduced amino acid sequences from the R blocks of E4, E1, E2 and E3 SEQ ID NO:10=Con, SEQ ID NO:41=E4R1, SEQ ID NO:42=E1R1, SEQ ID NO:43=E1R2, SEQ ID NO:44=E1R3, SEQ ID NO:45=E1R4, SEQ ID NO:46=E2R1, SEQ ID NO:47=E2R2, SEQ ID NO:48=E2R3, SEQ ID NO:49=E2R4, SEQ ID NO:50=E3R1, SEQ ID NO:51=E3R2, SEQ ID NO:52=E3R3.

Figure 10A:
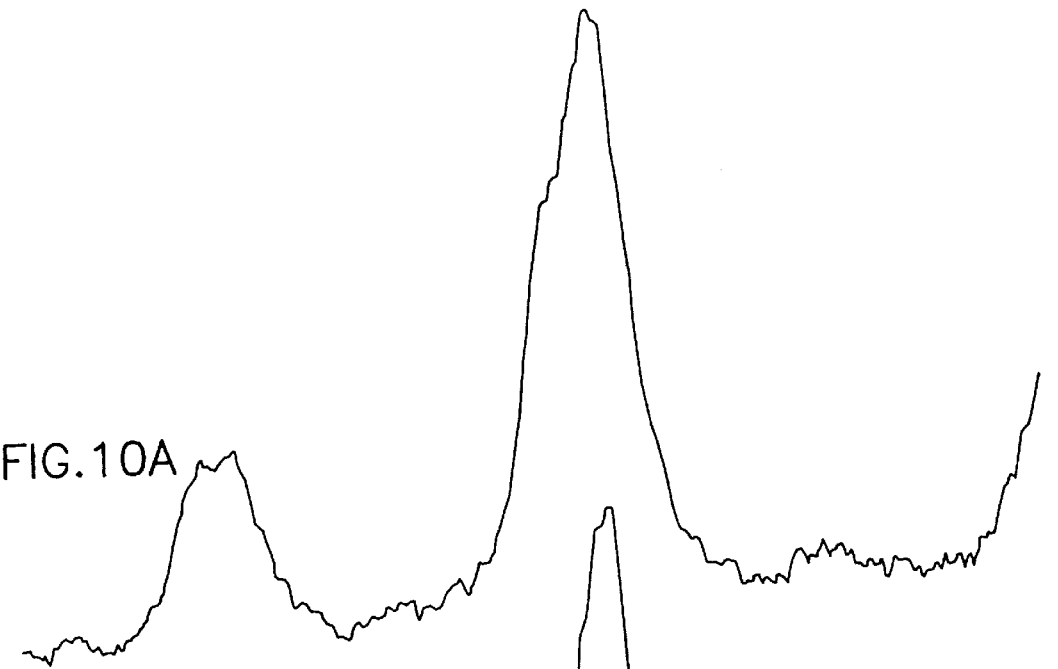
Figure 10B:
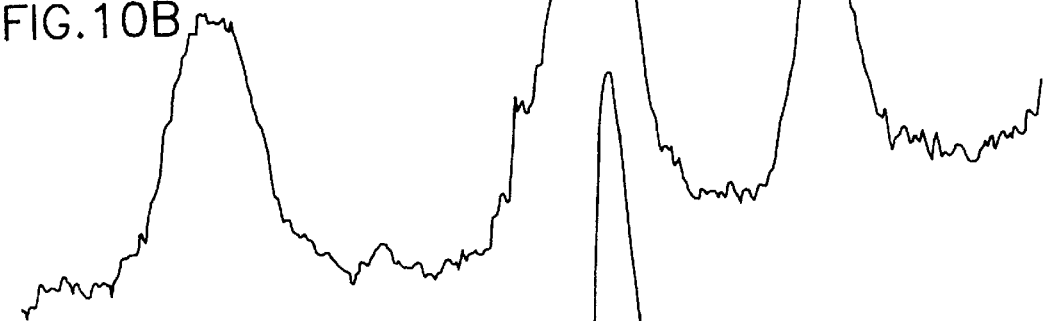
Figure 10C:

FIG. 10A–10C shows $^1H$-NMR spectra of alginate epimerized by extracts from A: DH5α(pHE8) (truncated epimerase 1); B: JM109(pBD9); C: no extract. The peak to the left gives the signal from G-1; the peak in the centre gives the combined signal from GM-5 and M-1 and the peak to the right gives the signal from GG-5.

FIGS. 11A–11F (SEQ ID NO:1) shows the nucleotide sequence and corresponding amino acid sequence of E2.

Now according to the present invention genetic sequences have been found which encode enzymes having mannuronan C-5-epimerase activity (MG copolymers), and thus the first aspect of the invention is pure isolated DNA comprising nucleotide sequences encoding mannuronan C-5-epimerase activity (GGhorropolymers).

The sequence of amino acids proximal to the amino terminus of purified mannuronan C-5-epimerase protein was determined [G. Skjåk Bræk et al., Carbohydr. Res. 103:133–136 (1982)]. This data was used to derive a sequence for an oligonucleotide probe which was used to screen a gene library of Azotobacter vinelandii DNA. One result of this screening experiment was the surprising discovery of a second gene and thereafter three further genes including at least one genetic block A were found. Thus, altogether there appear to be at least five different genes encoding proteins having mannuronan C-5-epimerase activity. Accordingly, it is a second object of the present invention to provide for alternative DNA sequences encoding mannuronan C-5-epimerase.

Three different blocks of genetic sequences, designated A, R and S, are found in the genes. These genetic blocks are most commonly found in combinations wherein the A appears one time or two times, the R block appears from 0 to at least 5 times and the S block appears from 0–1 time.

There is a high degree of consensus in the nucleotide sequences of each block for the different genes (1–5). Accordingly, it is a third object of the present invention to provide for DNA sequences encoding mannuronan C-5-epimerase and comprising the DNA blocks A and/or S and/or R, wherein A may appear more than once and R if present may appear singly or in repeats of up to at least 5 or 6 times.

The consecutive order of the three blocks if all three blocks are present, is preferably A, R and S. However, it has been shown that a reversed consecutive order, wherein for instance R appears before A also gives a gene encoding a mannuronan C-5-epimerase. Thus, the invention further encompasses genetic sequences having any order and any number of the blocks A, R and S.

Another aspect of the present invention concerns the use of said genetic sequences for the preparation of the mannuronan C-5-epimerase in recombinant host cells. It is especially preferred to insert the gene into hosts such as bacteria, for instance *Escherichia coli* or *Bacillus subtilis* or in yeast. The cloning and expression of the genetic sequence as described above in *E. coli* is described in the Examples.

The present invention also encompasses recombinant expression plasmids that can be used to produce the mannuronan C-5-epimerase proteins in a host microorganism. Such expression plasmids are made by inserting a DNA fragment encoding mannuronan C-5-epimerase into a vector which contains appropriate expression elements, such as (but not limited to) a promoter, ribosome binding site, translational initiation site and transcription terminator. The expression plasmids can be adapted for transformation into many different commonly used host organisms in which it might be desired to produce the mannuronan C-5-epimerase.

The techniques for insertion of foreign genes into commonly employed hosts are known in the art, as described for instance in [METHODS IN ENZYMOLOGY, Vol. 185, Gene Expression Technology, Ed. D. V. Goeddel, Academic Press, Inc. (1990)]. Further by choice of a broad host range vector and a suitable promoter as known in the art, and described for instance in [J. L. Ramos et al, FEBS Letters, Vol. 226, 2, 241–246] it will be possible to insert and express the mannuronan C-5-epimerase genetic sequences in many different hosts.

This will make possible the production of large quantities of one or all of the pure enzymes having this activity, while avoiding the problems of separating the enzymes from the alginate.

By inserting a high copy-number vector comprising the genetic sequences encoding the epimerase into a natural alginate producing bacterium such as *Azotobacter vinelandii* an enhanced production of the enzymes would be possible.

Over expression of the epimerases in a natural host could also be achieved by using a promoter which drives high-level expression of the enzymes. By blocking other genetic sequences coding for the alginate production, the production of pure enzymes may be achieved.

Yet another aspect of the invention is the selective inactivation of the mannuronan C-5-epimerase genes in the natural host organism so as to provide for bacterial production of alginates having a low content of G blocks or even a pure poly-M alginate. This is accomplished by inserting nucleotides into one, several or all of the mannuronan C-5-epimerase genes in the natural host organism Azotobacter. It is especially preferred to insert a DNA fragment encoding a selectable marker gene, preferably a gene conferring antibiotic resistance. Insertion of a selectable marker allows selection of those bacteria in which the insertion has been successfully accomplished. By choosing different selectable markers, for example providing resistance to different antibiotics, it is possible to select recombinants that have incorporated inserted sequences into some or all of the mannuronan C-5-epimerase genes. Thus, selective production of bacterial strains in which one of the mannuronan C-5-epimerase genes, several or all of them have been inactivated is possible.

A second method of inactivating all of the epimerase genes is to transform a cell of the natural host strain, Azotobacter with a vector which expresses an antisense RNA which specifically binds to mRNA transcribed from these genes. Use of promoters of varying strength to drive expression of the antisense RNA in the creation of the vectors used to transform the cells allows production of strains having varying ratios of G-blocks to M-blocks in the alginate produced. Use of inducible promoters to drive expression of the antisense RNA allows the creation of strains which can produce alginates of variable composition, depending on culture conditions. Clearly, if the recombinant host organism is the natural host, Azotobacter, it is possible to enhance production of one epimerase gene while leaving expression of the others at their normal level, thus producing a strain which makes an alginate having an altered ratio of G blocks to M blocks. A strain which makes alginate having 0–25% M blocks is preferred.

Alternatively, all but one of the epimerase genes can be inactivated, as described above, and the expression of the remaining epimerase gene can be controlled by a regulated promoter. A strain carrying such a complement of epimerase genes would thus produce alginates having a high content of G-blocks, especially from 75–98%. Another means for making a strain for producing alginates having a high G-block content is to inactivate all but one of the mannuronan C-5-epimerase genes by insertion and control the remaining gene by antisense RNA, using an inducible promoter to regulate transcription of the antisense RNA gene. A still further means for making a strain for producing alginates having a high G-block content is by inactivating all naturally occurring genes and introducing a regulated gene through a vector.

Thus the present invention also includes a process for the construction of a recombinant host cell capable of expressing mannuronan C-5-epimerase activity by transforming said host cell with a recombinant DNA expression vector that comprises: (a) a promoter and translational activating sequence that function in said host cell; and (b) a DNA sequence encoding mannuronan C-5-epimerase comprising at least a DNA block A and/or a DNA block S and/or a DNA block R, positioned for expression from said promoter and translational activity sequence.

Also the present invention encompasses a process for the bacterial production of pure poly-M alginate or tailored alginates having a lower G block content, preferably in the range from 0–25%, by blocking the DNA sequences encoding the enzymes in a natural host by insertion of a foreign genetic sequence into one, several or all genetic sequences encoding mannuronan C-5-epimerase.

Other methods for achieving the same end will be known for persons skilled in the art and are hereby included into the scope of the present invention.

A further aspect of the invention are the novel enzymes having mannuronan C-5-epimerase activity. The amino acid sequences and their degree of homology will appear from FIGS. 6–9 (SEQ ID NOS:7–10 and SEQ ID NO:1).

Also as known by a person skilled in the art, variations in the nucleotide sequence which nevertheless encode proteins having the same activity as the wild-type mannuronan C-5-epimerase are encompassed within this invention.

Variations within the amino acid sequence may also encompass deletions, substitutions and additions which do not substantially change the biological activity.

Also, it is possible to make a synthetic DNA sequence encoding a mannuronan C-5-epimerase by techniques well known in the art. See for instance, [Itakura et al., Science 198:1056 (1977)] and [Crea et al. (Proc. Natl. Acad. Sci. USA 75:5765 (1978)] and also U.S. Pat. Nos. 4,800,159 and 4,683,202 and also published European patent application EP-A-0258017. Synthetic enzymes may be made by incorporating different combinations of the A, R and S elements, to maintain epimerase activity. The resultant alginate composition can be varied by enzyme selection.

Materials and General Methods

Bacterial strains, plasmids, and phage. Strains, plasmids, and phages are listed in Table 1.

The bacterial strain of A. vinelandii used in these experiments, is freely available from Bjørn Larsen, Inst. of Biotechnology, Lab. for Marine Biochemistry, 7034 Trondheim—NTH, Norway or Svein Valla, Unigen, Center for Molecular Biology, University of Trondheim, 7005 Trondheim, Norway and has been deposited Oct. 4, 1993 at the Belgian Coordinated Collections of Microorganisms (BCCM) at the Laboratorium voor Microbiologie (LMG) at Universiteit Gent (RUG) under the accession number LMG P-14235, K. L. Ledeganckstraat 35, B-9000 Gent. Other strains of A.vinelandii mentioned in Example 9 have the following ATCC numbers: ATCC 478, ATCC 12837 and ATCC 12518. Plasmids/strains DH5α(pHE14), JM109(pHE16), JM109 (pBD1), JM109(pHE18) and SURE™(pML1) have been deposited Oct. 5, 1993 at BCCM at the Laboratorium voor Moleculaire Biologie (LMBP) (same address as LMG) and have the following accession numbers LMBP 2932, 2933, 2934, 2935 and LMBP 2936.

Growth of bacteria and phages. A. vinelandii was grown at 30° C. with shaking in a nitrogen-free medium (9.8 mM $K_2HPO_4/KH_2PO_4$, 0.8 mM $MgSO_4 7H_2O$, 3.4 mM NaCl, 0.34 mM $CaCl_2$, 8.7 μM $Na_2MoO_4 2H_2O$, 54 μM $FeSO_4 7H_2O$, 1% sorbitol, pH 7.4). E. coli was grown in LB-medium [Sambrook J, Fritsch, E. F. and Maniatis T., Molecular cloning, A laboratory manual, 2nd ed., Cold Spring Harbour Laboratory Press, New York, (1989)] with shaking at 37° C. When the cells were to be used for growth of phages the LB-medium was supplemented with 2.5 mM $CaCl_2$, 10 mM $MgCl_2$, and 0.4% maltose. Phages were plated on strain Q359 on L-agar (LB-medium supplemented with 2% agar). Phage LB-medium supplemented with either 0.8% agar (titrations and gene library amplification) or 0.8% agarose (screening of gene library and preparation of phage lysates) was used for overlaying agar.

Standard recombinant DNA technology. Restriction endonuclease digestions, removal of cohesive DNA ends by using the 3' exonuclease activity of T4 DNA polymerase, ligations, agarose gel electrophoresis, and end-labelling with $^{32}P$ were performed according to standard protocols [Sambrook J, Fritsch, E. F. and Maniatis T., Molecular cloning, A laboratory manual, 2nd ed., Cold Spring Harbour Laboratory Press, New York, (1989)]. Transformations were performed as described by [Chung, C. T., Niemela S. L. and Miller R. H., Proc. Natl. Acad. Sci USA, 86, 2172–2175, (1989)], and DNA sequencing was performed according to [Sanger F., Nicklen S., and Coulsom, A. R., Proc. Natl. Acad. Sci USA, 74, 4563 (1977)].

Viscosimetric measurement. The alginate used in this experiment was obtained from Ascophyllum nodosum and had an intrinsic viscosity in 0.1 M NaCl of 17.6 dl/g at 25° C. The viscosity was determined by an Ubbelhode viscosimeter.

NMR spectroscopy. The substrate used in these analyses was a low guluronic acid-containing alginate obtained from the brown algae Ascophyllum nodosum, and was prepared as described previously [Larsen, B., Proceedings of the Tenth International Seaweed Symposium, Ed: Levring, T.Gothenburg, p7–33, (1980)]. For the NMR analyses epimerase was obtained from IPTG-induced E. coli JM105 cells containing pHE5. 250 ml cell culture were harvested by centrifugation and resuspended in 20 ml of 10 mM Tris, 0.34 mM $CaCl_2$, pH 7.0. After ultrasonication, the solution was centrifuged at 31.000×g for 1 hour. The supernatant was stored frozen at 70° C. After thawing the supernatant was filtered through a membrane with pore size 0.22 μm, and the enzyme was further purified on a Mono Q HR515 (Pharmacia) ion exchange column. The enzyme was eluted with a 0–1 M NaCl salt gradient (in the same buffer as the applied solution), and was collected in 2 ml at approximately 0.6 M NaCl. To each of two tubes was added 0.28 ml of this enzyme solution (0.9 mg/ml total protein), 1 ml alginate (7.5 mg/ml in $H_2O$), and 4.62 ml 2,3,6-trimethylpyridine buffer (see above). $CaCl_2$ was then added to a total reaction volume of 6 ml such that one tube contained 0.85 μM, and one contained 3.4 mM $CaCl_2$. After incubation at 30° C. for 20 hours $Na_2EDTA$ (10 mM) was added to chelate the $Ca^{2+}$-ions, and the solutions were then dialyzed extensively against distilled water. The dialyzed alginate solutions were freeze-dried and then dissolved in $D_2O$. NMR spectroscopy of these solutions were finally performed according to [Grasdalen H., Larsen B., and Smidsrød O., Carbohydr. Res., 68, 23–31 (1979)] (Table 4). Further analysis was carried out in a similar fashion for DH5α(pHE8), JM109 (pHE16) and JM109(pBD9). The results in Table 4 conclusively demonstrate that the enzymatic activity is mannuronan C-5-epimerase activity. This activity is expressed from a number of the plasmids showing that an entire epimerase gene/protein is not required in order to maintain epimerase activity. The epimerase activity is $Ca^{2+}$ dependent.

EXAMPLE 1

Purification of mannuronan C-5-epimerase (1), partial amino acid sequencing and synthesis of a mixed DNA probe. The enzyme was isolated from liquid cultures of A. vinelandii essentially as described in [Skjåk-Bræk, G. and Larsen, B. Carbohydrate Research, 103, (1982) 137–140]. The cells were removed by centrifugation and the enzyme was isolated by precipitation with 30% ammoniumsulphate and followed by centrifugation for 20 min. at 10000 rpm. The supernatant was then precipitated with 50% ammonium sulphate (final concentration), and the precipitate after centrifugation was dissolved in 0.05 M imidazole/HCl (pH 6.8) containing 0.34 mM $CaCl_2$ and 0.5 mM dithiothreitol. This crude extract was then desalted on a prepacked column (PD-10) of Sephadex G-25 (Pharmacia) equilibrated with the same buffer. The extract was then applied on an alginate-Sepharose column. Proteins bound by non-specific interactions were eluted with 0.1 M NaCl. The epimerase was eluted as a sharp peak with 0.5 M NaCl. To make the enzyme pure enough for protein sequencing, it was dialyzed against TE-buffer overnight, freezedried, and further purified by SDS-PAGE gel electrophoresis (7.5% polyacrylamide in 25 mM Tris, 192 mM glycine, 0.1% sodium dodecyl sulphate, pH 8.3.) followed by electroblotting (in electrophoresis buffer without sodium dodecyl sulphate) onto a polyvinylidene difluoride membrane, poresize 0.45 μm (Millipore). The membrane was stained with Coomassie brilliant blue and air dried, and the protein with Mw 122 kd was cut out for N-terminal sequencing on a model 477A protein sequencing apparatus from Applied Biosystems. A DNA oligonucleotide was synthesized on the basis of the amino acid sequence information, and this oligonucleotide was used as a probe for screening of the gene library after end-labelling with $^{32}P$ by polynucleotide kinase.

EXAMPLE 2

Isolation of DNA from A. vinelandii and construction of a gene library. A. vinelandii cells were harvested and washed once in 0.9% Nacl. They were then lysed according to [Hansen, J. B. and Olsen, R. H., J. Bacteriol., 135, 227–238, (1978)], and the lysate was extracted twice with phenol and twice with chloroform. Nucleic acids were precipitated with ethanol, and the DNA was collected on a glass rod and dissolved in TE-buffer (10 mM Tris, 1 mM Na$_2$EDTA, pH 7.9). Further purification was obtained by CsCl/ethidium bromide density gradient centrifugation. After removal of the ethidium bromide by isopropanol extraction, the DNA solution was dialyzed against TE buffer.

The DNA (molecular size greater than 60 kb) was subjected to partial Sau3AI digestion under conditions maximizing the generation of 15–20 kb fragments. After ethanol precipitation the DNA was dissolved in 40 µl TE buffer to give a concentration of 0.5 µg/µl. The DNA was then dephosphorylated with calf intestine phosphatase, followed by inactivation of the enzyme by incubation at 75° C. for 10 minutes in the presence of 10 nM nitrilotriacetic acid. The dephosphorylated DNA was precipitated with ethanol and dissolved in 40 µl 0.1×TE buffer.

EMBL3 vector DNA was digested with BanHI+EcoRI, followed by an isopropanol precipitation step under conditions leaving the short BamHI/EcoRI oligonucleotides in solution [Frischauf A., Lehrach H., Poustka A. and Murray N., J. Mol. Biol., 170, 827–842, (1983)]. The Sau3AI-digested and dephosphorylated A. vinelandii DNA (1.75 µg) was then ligated with the BamHI/EcoRI-digested vector DNA (4.75 µg), using T4 DNA ligase in a total reaction volume of 20 µl. After ligations over night at 10° C., 10 µl of the ligation mixture was subjected to in vitro packaging in a Promega Biotech packaging system. The in vitro constructed phage particles were titrated on the E. coli strain Q359, and the library was finally amplified on Q359 in one cycle by plating on solid medium. Screening of the library was performed according to standard protocols [Sambrook, J., Fritsch, E. F. and Maniatis, T., Molecular Cloning, Laboratory Manual, 2nd Ed., Cold Spring Harbour Laboratory Press, (1989)], except that the highest stringency wash was 3.2 M tetramethylammonium chloride at 50° C. A total of 1.4×10$^5$ primary recombinant phages were constructed, a library complexity far above what is required for obtaining representativity of A. vinelandii genes.

EXAMPLE 3

Measurements of epimerase activity from mannuronan C-5-epimerase (1). (5-$^3$H) alginate was prepared as described in [Skjåk-Bræk, G. and Larsen, B., Carbohydrate Res., 103, 133–136, (1982)]. The (5-$^3$H)alginate was produced by growing Azotobacter vinelandii in a medium consisting of D-Glucose (20 g), K$_2$HPO$_4$ (1 g), MgSO$_4$.7 H$_2$O (200 mg), FeSO$_4$. 7 H$_2$O (50 mg), NaMoO$_4$. 2 H$_2$O (5 mg), NH$_4$OAc (2.3 g) and CaCl$_2$. 2 H$_2$O (50 mg) diluted to one liter with water. The cells were grown at 30° C. with vigorous shaking. After 30 hours, D-[5-$^3$H]glucose was added to a concentration of 0.6 mg/ml (Specific activity, 0.7 µCi/mg) and the cells were allowed to grow for another 72 hours. The culture was cooled in an ice-bath, and the cells were removed by centrifugation. The supernatant solution was dialysed against 0.05 M sodium EDTA (3×5 liters) for 24 hours followed by exhaustive dialysis against distilled water. The sodium alginate was then precipitated with ethanol in the presence of 0.2% of sodium chloride. The specific activity of the label was 29 000 dpm/mg alginate. The composition of this alginate was also analyzed by NMR spectroscopy, and it was found to contain 59% mannuronic acid. Phage lysates were prepared by plating 105 phages per plate. Two ml 2,3,6-trimethylpyridine buffer (50 mM, pH 6.9) were added to each plate, and the softagarose/buffer mixture was scraped off, vortexed and centrifuged at 10,000 rpm for 10 min. The supernatant was used for incubations with (5-$^3$H)alginate by mixing 0.25 ml (5-$^3$H)alginate (2.5 mg/ml), 6,3 µl 0.1 M CaCl$_2$, and 1.45 ml phage lysate. The mixture was incubated at 30° C. overnight, and the alginate was precipitated by addition of 15 µl 5 M NaCl and 2 ml ethanol. After incubation at −20° C. for 30 min. the solution was centrifuged at 10.000 rpm for 30 min., and 1 ml of the supernatant was used for determination of released $^3$H [Skjåk-Bræk, G. and Larsen, B., Carbohydrate Res., 103, 133–136, (1982)]. in a liquid scintillation counter.

For measurements of epimerase activity as release of $^3$H in cells containing recombinant plasmids, the cell cultures were harvested by centrifugation and resuspended in 2,3,6 trimethylpyridine buffer. When IPTG (3 mM) was used for induction of the lac-promoter, the inducer was added to exponentially growing cells and incubations were continued for 3 hours. Cells were disrupted by ultra-sonication, and varying amounts of the lysates were incubated with shaking together with 100 µl (5-$^3$H) alginate (2.5 mg/ml) and 400 µl 2,3,6-trimethylpyridine buffer (total volume 0.6 ml) in the presence of 3.3 mM CaCl$_2$. The quantities of enzyme-containing cell extracts used were adjusted such that the measurements were performed under conditions where the enzyme represented the limiting factor. After incubation at 30° C. at the times indicated in each case, the mixtures were precipitated with ethanol under the conditions described above for phage lysates and 1.0 ml of the supernatant was used for scintillation counting. Controls (using the appropriate host with the pUC18 vector) gave low backgrounds and these numbers were subtracted in the values presented in Table 3.

EXAMPLE 4

Molecular cloning of a DNA fragment expressing a mannuronan C-5-epimerase activity in E. coli. The A. vinelandii gene library was constructed by cloning partially Sau3AI-digested A. vinelandii DNA into the bacteriophage λ vector EMBL3. In order to identify the epimerase gene in this library, we constructed a DNA probe based on the assumption that the previously purified 122 kd protein represented the epimerase [Skjåk-Bræk, G. and Larsen, B., Carbohydr. Res., 103, 137–149 (1982)]. Initially we tried to use the corresponding protein solution for determination of the N-terminal amino acid sequence of the 122 kd protein, but the results showed that the preparation was not sufficiently pure for this purpose. We therefore purified the protein further by SDS-polyacrylamide gel-electrophoresis, followed by electroblotting onto a membrane. The band containing the 122 kd protein was cut out from this membrane and subjected to N-terminal amino acid sequence analysis. Based on parts of this sequence, we synthesized the mixed DNA probe shown in FIG. 1 (SEQ ID NO:6).

The DNA probe synthesized as in Example 1 was labelled with $^{32}$P and then used for screening of the A. vinelandii gene library. Clones which hybridized reproducibly against the labelled probe were identified at a frequency of approximately 10$^{-3}$, and six such clones were selected for further studies. Phage lysates were prepared from each of the six clones, and each lysate was assayed for epimerase activity (Table 2). As can be seen, the lysates prepared from all six clones appeared to contain a weak enzyme activity that could represent the epimerase. This conclusion was further supported by the observation that control lysates prepared from randomly picked recombinant phages in the library, gave reproducibly lower activity, representing the background activity.

EXAMPLE 5

Subcloning of a DNA fragments encoding the epimerase. DNA from phage EP2 was partially digested with Sau3AI, and fragments ranging from 4 to 9 kb in size were subcloned in the BamHI site of plasmid pUC18. Cell extracts from DH5α transformants containing recombinant plasmids were assayed for epimerase activity, and the corresponding plasmids were also hybridized against the synthetic oligonucleotide used for screening of the gene library. The analysis of the cell extracts showed that one of them contained an enzymatic activity consistent with the assumption that a polypeptide having epimerase activity was expressed from the plasmid (pHE1) in this clone (see Table 3). We have also tried to centrifuge the extract at 30000 g for 3.5 hours, and found that the activity was not significantly reduced in the supernatant. Since we were unable to detect any significant activity in the culture medium, we conclude that the epimerase is localized intracellularly in E.coli. The insert in pHE1 also hybridized against the synthetic oligonucleotide used for screening, and pHE1 was therefore selected for further analysis.

EXAMPLE 6

Characterisation of the cloned DNA required for expression of the epimerase, and stability of the enzyme in vivo and in vitro. The insert in pHE1 is approximately 4 kb in size, and FIG. 2 shows the restriction map of this insert. Hybridization analysis of pHE1 with the original synthetic oligonucleotide showed that the sequence hybridizing to the oligonucleotide was localized downstream of the SphI site. The hybridizing sequence was further characterized by DNA sequencing, and this analysis showed that one of the potential reading frames of the sequence was in 100% agreement with the original N-terminal amino acid sequence of the 122 kd protein. Surprisingly, however, the orientation of the sequence was such that it would be transcribed out of the cloned fragment (see FIG. 2). This result thus indicated that the observed epimerase activity was not correlated with the sequence encoding the 122 kd protein, a conclusion that was further confirmed by the observation that the terminal 0.5 kb SphI fragment could be deleted (generating plasmid pHE7) without loss of the epimerase activity from the corresponding cell extract. In addition to the SphI deletion, we deleted (from pHE7) the 0.7 kb KpnI fragment at the opposite terminus of the insert, generating plasmid pHE5. As shown in Table 3, pHE5 (in DH5α) expressed the epimerase at a level approximately 27 times higher than the level of expression from pHE1.

During the expression studies described above we found that the measurements were quantitatively difficult to reproduce unless the time of harvesting the cells were kept as constant as possible. We have analyzed this problem more carefully by measuring the enzyme activity at different stages of growth of the E. coli cells. The results of such an analysis are shown in FIG. 3, and indicate that the enzymatic activities in the cell extracts are drastically reduced shortly after the cells have entered the stationary phase. To obtain optimal enzyme yields it is therefore important to harvest the cells at the end of the exponential phase or at the beginning of the stationary phase. The reason for the reduction of epimerase activity might potentially be due to proteolysis of the epimerase in stationary phase cells. To study the stability of the enzyme in vitro we have also analyzed the kinetics of $^3$H release in the DH5α(pHE5) extracts. As can be seen from FIG. 4, the enzyme activity is linear over at least 30 hours, demonstrating that the enzyme is very stable in vitro. A critical parameter for obtaining reproducible results is thus the time of harvesting of the cells.

EXAMPLE 7

Stimulation of the epimerase activity by induction of the lac promoter. The results described above showed that the levels of expression of the epimerase from pHE5 was significantly higher than in pHE1. The reasons for this could potentially be that the lac promoter was important for the expression, and we have therefore analysed this problem more closely. The analyses were performed in the E. coli strain JM105, a strain which expresses high levels of lac repressor, thus allowing a more repressed state of the promoter under uninduced conditions. When cell extracts prepared from uninduced and induced (with IPTG) cells of JM105(pHE1), a significant stimulation of enzyme activity was observed in the induced cells (Table 3). A similar experiment using JM105(pHE5) showed even greater stimulation of the expression of the epimerase upon addition of IPTG in this case. These experiments thus showed that the lac promoter probably is a key element, although not necessarily the only element, involved in the expression of the epimerase from pHE5. The experiments in addition showed that the direction of transcription is from the KpnI towards the SphI site in the insert. The epimerase gene is therefore transcribed in the same direction as the gene encoding the 122 kd protein, whose N-terminal amino acid sequence was used for the isolation of the cloned DNA.

Preliminary experiments on deleting more DNA from the SphI side of the insert indicated that very little could be deleted without loss of the epimerase activity. At the KpnI side, on the other hand, we found that significant deletions were tolerated. Table 3 shows the results of analysis of expression of the epimerase from a plasmid (pHE8) constructed by deleting the 0.8 kb KpnI/SacII fragment from pHE5. As can be seen, this deletion resulted in a very strong stimulation of the epimerase activity both in uninduced and induced cells. The expression from pHE8 is presumably based on initiation of translation from the Shine-Dalgarno sequence in the vector (localized between the lac promoter and the polylinker). Similarly, high levels of expression were obtained from pHE22 also due to the coding sequences being in frame with the Shine-Dalgano sequence. So far we have not obtained expression of the epimerase in constructs where deletions have extended beyond the SacII site.

EXAMPLE 8

Use of a different promotor than the lac promotor. The insert in pHE5 (EcoRI-HindIII) was sub-cloned into plasmid pT7-3 (a derivative of pT7-1 described by [Tabor, S., and C. C. Richardson (1985). Proc. Natl. Acad. Sci. 82, 1074–1078]), and the new plasmid was designated pLB1. The insert in pLB1 is localized downstream of the φ10 promoter in the vector. This promoter is only recognized by the bacteriophage T7 RNA polymerase, and expression of genes downstream of this promoter thereby becomes dependent on expression of this polymerase activity in the cells. The 442 bp (see FIG. 2) SacI- SpoI fragment was finally deleted from the insert in pLB1, generating plasmid pLB2. pLB2 was transformed into E. coli K38 (pGP1–2). Plasmid pGP1–2 encodes the gene for T7 RNA polymerase, and the expression of the gene is controlled by a temperature inducible repressor. K38(pLB1, pGP1–2) was grown in exponential phase at 30° C. for 4½ hours. One of two parallel cell cultures was then transferred to 42° C. for 30 minutes to induce the T7-polymerase. The other parallel cell culture was grown at 30° C. for 5 hours. The epimerase activities in the cells were measured as described in example 3, and the results of the measurements are shown in Table 3.

EXAMPLE 9

Cloning of mannuronan C-5-epimerase (2). Plasmid pHE12 was constructed by inserting a 6.2 kb XhoI fragment from the recombinant bacteriophage lambda derivative EP2 into pUC128. As can be seen from FIG. 2 the insert in pHE12 is partly overlapping with the insert in pHE1. Analysis of extracts prepared from cells containing pHE12 (as described for pHE1), showed that they expressed mannuronan C-5-epimerase activity (Table 3). Further analysis showed that the 2.5 kb SpoI-XhoI fragment could be deleted from the insert in pHE12 without affecting the expression of mannuronan C-5-epimerase. Further plasmids were constructed (see FIG. 2) and the activity analysed (see Table 3). This demonstrated that both the genes and gene fragments were able to express epimerase activity. The nucleotide sequences of the inserts were determined by the method of Sanger [Sanger, F., S. Nicklen, and A. R. Coulson. 1977. Proc. Natl. Acad. Sci. 74, 5436]. The nucleotide sequences are shown in FIG. 6.

EXAMPLE 10

Sequence Comparison. Five genes have been identified as shown in FIG. 2. The insert containing E5 is located about 5–10 kilobases away from the other genes. SEQ ID NO:1 shows the nucleotide sequence for the complete genes of E4, E1, E2 and a large portion of E3. SEQ ID NO:2-SEQ. ID NO:5 sequentially show the amino acid sequences for E4, E1, E2 and a large portion of E3. Detailed analysis of the nucleotide and amino acid sequences revealed highly homologous regions within each gene and between the various genes. FIG. 5 characterises each of the genes by reference to the homologous blocks. Each of the genes has at least one A-element and at least one R-element.

E1, E2 and E4 all end with a reasonably homologous sequence termed the S-element (not shown in FIG. 5). The last 14 amino acids of the S-element of E1 and E2 are identical with one exception. FIGS. 6–9 show detailed analysis of the A- and R-elements within each gene by reference to the consensus sequence (con) (SEQ ID NO:7–SEQ ID NO:10). Each A-element is approximately 1,150 base pairs long and each R-element is approximately 450 base pairs long. Short oligonucleotides are present in E1, E2 and E3 between the second and third R-elements. Gaps have been introduced where necessary to maximise alignment (see in particular the third R-element of E2).

Hybridization with a probe made from the first part of the A-element to a Southern blot of *A. vinelandii* digested with restriction endonuclease BglII gave 5 distinct bands. One of these bands contained two A blocks, and another of these bands contained two different fragments with the same size. The number of bands were the same when other strains (ATCC 478, ATCC 12837 and ATCC 12518) of the same species were used. This implies that the bacterium contains at least 5 copies of the A-element, and that this is common to several independently isolated strains of *A. vinelandii*.

The first part of each R-element contains six perfect and imperfect repeats of a nonapeptide with the consensus sequence LXGGAGXDX (SEQ ID NO:11), except for the third R-element of E2 which lacks two of these repeats. FIG. 11 shows the complete nucleotide (SEQ ID NO:1) and corresponding amino acid sequence of E2. The nonapeptides have been marked with double lines for a good match with the consensus sequence and single lines for less good matches. This nonapeptide motif is characteristic of the haemolysin family of secreted proteins (Suh, Y. and Benedik, M. J., J. Bacteriol 174, (1992) 2361–2366). These proteins are all calcium dependent and are secreted by a pathway which does not involve cleavage of an N terminal signal peptide. For haemolysin secreted from *E. coli* it has been proposed that the nonamers are responsible for the binding of calcium ions (Ludwig, A. et al, Mol. Gen. Genet. 214, (1988) 553–561, Boehm, D. F. et al, Infect. Immun. 58 (1990) 1959–1964). It appears that the R-elements are involved in calcium ion binding, calcium being necessary for both enzyme activity and gel formation.

EXAMPLE 11

Making an altered epimerase.

As can be seen from Table 3, various elements may be deleted from the gene, while maintaining the expression of a protein having epimerase activity. Clearly, the latter portion of E1 having the sequence ARS has epimerase activity (see plasmid pHE8), although deletions in A2 of E1 are not tolerated (see Example 7). Additionally, E2 having the sequence ARRRRS (SEQ ID NO:12) also demonstrates epimerase activity. Additionally, fragments of E3 lacking a carboxy terminal and having the sequences ARRR (SEQ ID NO:15) and ARRRARR (SEQ ID NO:13) have expressed epimerase activity. (See plasmids pH18 and pBD6). Accordingly, it appears that an S-element is not essential for epimerase activity, although the presence of this element may affect activity. We therefore postulated that an epimerase may need at least one A-element and at least one R-element, and that it should be possible to make altered epimerases by combining these elements in different ways. To show this, we constructed a plasmid encoding an epimerase with the sequence RARS (SEQ ID NO:14):

The insert in pHE1 (EcoRI-HindIII) was subcloned into plasmid pTrc99A (Pharmacia), generating plasmid pHE21. This plasmid contains a trc-promoter in front of the epimerase I gene, a strong transcription termination signal downstream of the gene, and the lacI$^q$-gene allowing induction with IPTG. pHE21 was digested with KpnI and SpoI, made blunt-ended with S1 nuclease and religated. The resulting plasmid, pHE22, expresses a protein having the carboxy terminal of epimerase 1, RARS. The epimerase activity was measured as in Example 3, see Table 3.

Given that epimerase activity is expressed from a number of the constructs, it seems likely that a number of synthetic enzymes may be produced having epimerase activity including differing numbers of A, R and S blocks. The presence of activity in pHE22 implies that it is not essential to have an amino-terminal A block, and so block order may also be altered.

EXAMPLE 12

The $^1$H-NMR spectra of alginate epimerased by extracts from plasmids pHE8 and pBD9 show that the proteins encoded by these plasmids have different enzyme activity, pHE8 producing epimerase with single G activity while pBD9 producing epimerase with G block activity. pHE8 encodes the carboxy terminal ARS of E1 whereas pBD9 encodes ARRRRS (SEQ ID NO:12) of E2. The naturally encoded epimerases may therefore have differing activity particularly in the distribution patterns of Gs. The different activity of the various epimerases encoded within the 5 genes could be used to create alginates having a desired structure, by selectively expressing a desired gene or genes. Alternatively, it may be possible to construct synthetic enzymes varying the A, R and S block content of each epimerase to provide enzymes having altered activity providing a further level of control in the production of desired alginates.

TABLE 1

Bacterial strains, phages, and plasmids

| Strain/phage/plasmid | Remarks | References |
|---|---|---|
| Bacterial strains | | |
| A. vinelandii | Strain E | Larsen and Haug (1971) |
| E. coli | | |
| Q359 | supE hsdR φ80^r P2 | Karn et al. (1980) |
| DH5α | supE44ΔlacU169 (φ80 lacZΔM15) hsdR17 recA1 endA1 gyrA96 thi-1 relA1 | Bethesda Research Laboratories (1986) |
| JM105 | supE endA sbcB15 hsdR4 rpsL thiΔ(lac—proAB) | Yanisch-Perron et al (1985) |
| JM109 | recA1 supE44 endA1 hsdR17 gyrA96 relA1 thiΔ(lac—proAB) F'[traD36 proAB +lacI^q lacZΔM15] | Yanisch-Perron et al (1985) |
| SURE™ | e14⁻(mcrA), Δ(mcrCB—hsdSMR—mrr) 171, endA1, supE44, thi-1, gyrA96, relA1, lac, recB, recJ, sbcC, umuC:Tn5(kan^r), uvrC, [F' proAB, lacI^q ZΔM15, Tn10, (tet^r)]. | Greener (1990) |
| Phages | | |
| EMBL3 | Bacteriophage λ vector used for construction of A. vinelandii gene library | Frischauf et al. (1983) |
| EPx | Randomly picked phage from A. vinelandii gene library | See examples |
| EP2, -3, -6, -7, -8 and -9 | Phages isolated from A. vinelandii gene library Identified by hybridization and expresses mannuronan C-5-epimerase | See examples |
| Plasmids | | |
| pUC18 | Ampicillin resistance, ColE1 replicon | Norrander et al. |
| pUC128 | Ampicillin resistance, ColE1 replicon | Keen et al. (1988) |
| pTrc99A | Ampicillin resistance, ColE1 replicon | Pharmacia |
| pT7-3 | Ampicillin resistance, ColE1 replicon | Tabor & Richardson (1985) |
| pGP1-2 | Kanamycin resistance, P15A replicon | Tabor & Richardson (1985) |
| pBluescript II SK(+) | Ampicillin resistance, ColE1 replicon | |
| pHE1 | Derivative of pUC18 where a 4 kb Sau3A1 DNA fragment from phage EP2 was subcloned into the BamH1 polylinker | See examples |
| pHE7 | Derivative of pHE1 where a 0.5 kb Sph1 DNA fragment was deleted | See examples |
| pHE5 | Derivative of pHE7 where a 0.7 kb Kpn1 DNA fragment was deleted | See examples |
| pHE8 | Derivative of pHE5 where a 0.8 kb Kpn1/SacII DNA fragment was deleted. Cohesive ends were removed prior to ligation by using the 3' exonuclease activity of T4 DNA polymerase | See examples |
| pLB1 | Derivative of pT7-3, where the 2,7 kb insert from pHE5 was cloned into the EcoRI/HindIII polylinker | See examples |
| pLB2 | Derivative of pLB1, where a 0.4 kb SacI/SpoI fragment was deleted | See examples |
| pHE12 | Derivative of pUC128, where a 6.2 kb XhoI fragment from phage EP2 was subcloned into the XhoI polylinker | See examples |
| pBD1 | Derivative of pHE12, where a 2.0 kb SpoI/NsiI fragment was deleted | See examples |
| pHE21 | Derivative of pTrc99A, where the 4.0 kb insert of pHE1 was cloned into the EcoRI/HindIII polylinker | See examples |
| pHE22 | Derivative of pHE21, where a 1.2 kb KpnI/SpoI fragment was deleted | See examples |
| pHE2 | Derivative of pUC18 where a 6.0 kb SphI DNA fragment from phage EP6 was cloned into the SphI site in the polylinker of the vector | See examples |
| pHE16 | Derivative of pHE2 where a 1.5 kb EcoRI—SmaI DNA fragment was deleted | See examples |
| pBD9 | Derivative of pBD1 where a 0.4 kb XhoI—FspI DNA fragment was deleted | See examples |
| pBD6 | Derivative of pHE12 where a 3.4 kb XhoI—FspI DNA fragment was deleted | See examples |
| pHE18 | Derivative of pUC128 where an 5.1 kb NotI—PvuII DNA fragment from EP6 was cloned into the NotI—EcoRV sites in the polylinker of the vector | See examples |
| pHE14 | Derivative of pUC128 where a 3.0 kb BglII DNA fragment from EP6 was cloned into the BamHI site of the polylinker | See examples |
| pML1 | Derivative of pBluescript II SK(+) where a 4.3 kb KpnI—SacII DNA fragment was cloned into the corresponding sites in the polylinker | See examples |

References to Table 1

Larsen, B., and A. Haug. 1971. Biosynthesis of alginate. Carbohydr. Res. 17:287–296.

Karn, J., S. Brenner., L. Barnett, and G. Cesareni. 1980. Proc. Natl. Acad. Sci. U.S.A. 77:5172.

Bethesda Research Laboratories. 1986. Bethesda Res. Lab. Focus 8(2):9.

Yanisch-Perron, C., J. Vieira, and J. Messing. 1985. Gene 33:103–119.

Frischauf, A., H. Lehrach, A. Poustka, and N. Murray. 1983. J. Mol. Biol. 170:827–842.

Norrander, J., T. Kempe, J. Messing. 1983. Gene 26:101–106.

Keen N. T, S. Tamaki, D. Kobayashi and D. Trollinger (1988). Gene 79:191–197.

Tabor S. and C. C. Richardson (1985). Proc Natl Acad Sci USA 82:10741078.

Greener, A. (1990) Strategies 3:5–6.

TABLE 2

Putative mannuronan C-5-epimerase activity in recombinant phage lysates.

| Recombinant phage | ³H release (dpm) |
|---|---|
| EPx | 39 |
| EP2 | 91 |
| EP3 | 107 |
| EP6 | 74 |
| EP7 | 75 |

TABLE 2-continued

Putative mannuronan C-5-epimerase activity
in recombinant phage lysates.

| Recombinant phage | $^3$H release (dpm) |
|---|---|
| EP8 | 245 |
| EP9 | 75 |

EPx originated from the *A. vinelandii* gene library as a randomly picked plaque, while the other six phages were selected on the basis of the hybridization between their DNA and the labelled oligonucleotide used for screening of the library.

TABLE 3

Activity of the mannuronan C-5-epimerase
expressed from the plasmids.

| | | Released $^3$H/0D$_{600}$ unit cell culture | |
|---|---|---|---|
| Enzyme | Strain | No IPTG | IPTG |
| Epimerase 1[1] | JM109 (pHE16) | 10000 | 11000 |
| Epimerase 1[2] | DH5α (pHE1) | 273 | nd |
| Epimerase 1[3] | DH5α (pHE5) | 9700 | nd |
| Epimerase 1[4] | JM105 (pHE1) | 637 | 2800 |
| Epimerase 1[5] | JM105 (pHE5) | 4800 | 28500 |
| Epimerase 1[6] | JM105 (pHE8) | 58900 | 181000 |
| Epimerase 1[7] | JM109 (pHE21) | 93 | 1283 |
| Epimerase 1[8] | JM109 (pHE22) | 5383 | 34611 |
| Epimerase 1[9] | K38 (pGP1-2, pLB2)* | 2150 | 8333 |
| Epimerase 2[1] | JM109 (pHE12) | nd | 140 |
| Epimerase 2[2] | JM109 (pBD9) | nd | 6700 |
| Epimerase 3[1] | JM109 (pHE18) | 551 | 2270 |
| Epimerase 3[2] | JM109 (pBD6) | nd | 530 |
| Epimerase 4 | DH5α (pHE14) | nd | 3500 |

The extracts were incubated with the alginate for 16 hours, and the numbers are given in dpm. nd = not determined.
*Thge culture was not induced by IPTG, but by raising the temperature from 30° C. to 42° C.

TABLE 4

NMR analysis of the reaction product after incubation of the recombinant epimerase with a low guluronic acid containing substrate

| | CaCl$_2$ | Frequencies of M and G residues | | | | | |
|---|---|---|---|---|---|---|---|
| Strain | (mM) | F$_M$ | F$_G$ | F$_{MM}$ | F$_{MG}$ | F$_{GG}$ | F$_{GG}$/F$_G$ |
| JM105(pHE5) | 0.85 | 0.80 | 0.20 | 0.66 | 0.14 | 0.06 | 0.3 |
| JM105(pHE5) | 3.4 | 0.71 | 0.29 | 0.45 | 0.26 | 0.03 | 0.10 |
| DH5α(pHE8) | 3.4 | 0.72 | 0.28 | 0.52 | 0.20 | 0.08 | 0.29 |
| JM109(pHE16)* | 3.4 | 0.82 | 0.18 | 0.79 | 0.03 | 0.15 | 0.83 |
| JM109(pBD9) | 2.1 | 0.60 | 0.40 | 0.54 | 0.06 | 0.34 | 0.85 |

*This spectrum was obtained at a 400 MHz instrument to be able to get relatively correct figures in spite of the lower conversion.

We claim:

1. A DNA compound comprising a sequence encoding mannuronan C-5-epimerase, said sequence comprising one or more sequences selected from the group consisting of a DNA A block comprising the DNA of SEQ ID NO:7 or any one of SEQ ID NOS:17–22, or a DNA molecule encoding an amino acid sequences comprising an amino acid sequence of SEQ ID NO:8 or any one of SEQ ID NOS:23–28, or a DNA molecule which hybridizes to consensus sequence SEQ ID NO:7 under high stringency conditions comprising a wash step of 3.2 M tetramethylammonium chloride at 50° C.; and a DNA R block comprising the DNA of SEQ ID NO:9 or any one of SEQ ID NOS:29–40, or a DNA molecule encoding an amino sequence comprising an amino acid sequence of SEQ ID NO:10 or any one of SEQ ID NOS:41–52, or a DNA molecule which hybridizes to consensus sequence SEQ ID NO:9 under high stringency conditions comprising a wash step of 3.2 M tetramethylammonium chloride at 50° C.; and being isolated from a natural source or being derived synthetically.

2. An isolated DNA compound according to claim 1 encoding mannuronan C-5-epimerase that comprises at least one DNA block A comprising the DNA of SEQ ID NO:7 or any one of SEQ ID NOS:17–22, and a DNA block R comprising the DNA of SEQ ID NO:9 or any one of SEQ ID NOS:29–40 in a number of 0 to 5.

3. An isolated DNA compound comprising at least a portion of the DNA sequence as set forth in SEQ ID NO:1 wherein said compound comprises one or more sequences encoding a DNA A block comprising the DNA of SEQ ID NO:7 or any one of SEQ ID NOS:17–22, or a DNA molecule encoding an amino acid sequence comprising an amino acid sequence of SEQ ID NO:8 or any one of SEQ ID NOS:23–28, or a DNA molecule which hybridizes to consensus sequence SEQ ID NO:7 under high stringency conditions comprising a wash step of 3.2 M tetramethylammonium chloride at 50° C.; and/or a DNA R block comprising the DNA of SEQ ID NO:9 or any one of SEQ ID NOS:29–40, or a DNA molecule encoding an amino sequence comprising an amino acid sequence of SEQ ID NO:10 or any one of SEQ ID NOS:41–52, or a DNA molecule which hybridizes to consensus sequence SEQ ID NO:9 under high stringency conditions comprising a wash step of 3.2 M tetramethylammonium chloride at 50° C.

4. An isolated DNA compound according to claim 1 that encodes at least a portion of the protein amino acid sequence as set, said sequence containing SEQ ID NOS:2,3,4 and 5.

5. A recombinant DNA vector that comprises the DNA sequence of claim 1.

6. A method for constructing a recombinant host cell for production of enzymes having mannuronan C-5-epimerase activity and/or the microbiological production of alginates which comprises transforming a host cell with the DNA of claim 1.

7. The method according to claim 6 which comprises the microbiological production of alginates having a high G block content of 75–98%.

8. The method according to claim 6 which comprises the microbiological production of alginates wherein the DNA sequence is selected to produce an alginate having a desired M/G block content.

9. A method for the production of enzymes having mannuronan C-5-epimerase activity comprising constructing a recombinant host cell capable of expressing epimerase activity, characterized by transforming said host cell with a recombinant DNA expression vector that comprises:

(a) a promoter and translational activating sequence that function in said host cell; and (b) a DNA sequence encoding mannuronan C-5-epimerase comprising a DNA block A comprising the DNA of SEQ ID NO:7 or any one of SEQ ID NOS:17–22, or a DNA molecule encoding an amino acid sequence comprising an amino acid sequence of SEQ ID NO:8 or any one of SEQ ID NOS:23–28, or a DNA molecule which hybridizes to consensus sequence SEQ ID NO:7 under high stringency conditions comprising a wash step of 3.2 M tetramethylammonium chloride at 50° C. and/or a DNA block R comprising the DNA of SEQ ID NO:9 or any one of SEQ ID NOS:29–40, or a DNA molecule encoding an amino sequence comprising an amino acid sequence of SEQ ID NO:10 or any one of SEQ ID NOS:41–52, or a DNA molecule which hybridizes to consensus sequence SEQ ID NO:9 under high stringency conditions comprising a wash step of 3.2 M tetramethylammonium chloride at 50° C., positioned for expression from said promoter and translational activity sequence.

10. A process for the bacterial production of alginates comprising selectively inactivating one or more DNA sequences containing at least one A block comprising the DNA of SEQ ID NO:7 or any one of SEQ ID NOS:17–22, or a DNA molecule encoding an amino acid sequence comprising an amino acid sequence of SEQ ID NO:8 or any one of SEQ ID NOS:23–28, or a DNA molecule which hybridizes to consensus sequence SEQ ID NO:7 under high stringency conditions comprising a wash step of 3.2 M tetramethylammonium chloride at 50° C., or R block comprising the DNA of SEQ ID NO:9 or any one of SEQ ID NOS:29–40, a a DNA molecule encoding an amino sequence comprising an amino acid sequence of SEQ ID NO:10 or any one of SEQ ID NOS:41–52, or a DNA molecule which hybridizes to consensus sequence SEQ ID NO:9 under high stringency conditions comprising a wash step of 3.2 M tetramethylammonium chloride at 50° C. and encoding mannuronan C-5-epimerases in a natural host cell wherein said mannuronan C-5-epimerases produce alginates.

11. Process according to claim 10 for the production of pure poly-M alginate or alginates having a G block content from 0 to 25%.

12. Process according to claim 10 for the production of alginates wherein said DNA sequences are selectively inactivated to produce alginates having a desired M/G block content and G block distribution.

13. A DNA compound according to claim 1 wherein said compound is not naturally occurring in an alginate producing host and comprises at least one A block comprising the DNA of SEQ ID NO:7 or any one of SEQ ID NOS:17–22 and at least one R block comprising the DNA of SEQ ID NO:9 or any one of SEQ ID NOS:29–40 isolated from a natural source or being derived synthetically.

14. A DNA compound encoding a mannuronan C-5-epimerase, wherein said C-5-epimerase comprises an amino acid sequence corresponding to that of a mannuronan C-5-epimerase produced by *Azotobacter vinelandii*.

15. A DNA compound comprising a sequence encoding mannuronan C-5-epimerase, said sequence comprising one or more sequences of a DNA A block comprising the DNA of SEQ ID NO:7 or any one of SEQ ID NOS:17–22, or a DNA molecule encoding an amino acid sequence comprising an amino acid sequence of SEQ ID NO:8 or any one of SEQ ID NOS:23–28, or a DNA molecule which hybridizes to consensus sequence SEQ ID NO:7 under high stringency conditions comprising a wash step of 3.2 M tetramethylammonium chloride at 50° C. and being isolated from a natural source or being derived synthetically.

16. The DNA compound of claim 15 further comprising one or more sequences of a DNA R block comprising the DNA of SEQ ID NO:9 or any one of SEQ ID NOS:29–40, or a DNA molecule encoding an amino sequence comprising an amino acid sequence of SEQ ID NO:10 or any one of SEQ ID NOS:41–52, or a DNA molecule which hybridizes to consensus sequence SEQ ID NO:9 under high stringency conditions comprising a wash step of 3.2 M tetramethylammonium chloride at 50° C.

* * * * *

```
                         SEQUENCE LISTING (1) GENERAL INFORMATION:

(iii) NUMBER OF SEQUENCES: 52

(2) INFORMATION FOR SEQ ID NO:1:

(i) SEQUENCE CHARACTERISTICS:
         (A) LENGTH: 12588 base pairs
         (B) TYPE: nucleic acid
         (C) STRANDEDNESS: single
         (D) TOPOLOGY: linear (ii) MOLECULE TYPE: DNA (genomic)

(vi) ORIGINAL SOURCE:
         (A) ORGANISM: Azotobacter vinelandii
         (B) STRAIN: E (ix) FEATURE:
         (A) NAME/KEY: CDS
         (B) LOCATION: 290..1951

(ix) FEATURE:
         (A) NAME/KEY: CDS
         (B) LOCATION: 2227..6438

(ix) FEATURE:
         (A) NAME/KEY: CDS
         (B) LOCATION: 6702..9695

(ix) FEATURE:
         (A) NAME/KEY: CDS
         (B) LOCATION: 9973..12588
```

(xi) SEQUENCE DESCRIPTION: SEQ ID NO:1:

```
GATCCGGCCG TCTGAGACGG CGCCTCCGGC CGTCGGCGAG TGCGCCGTTC GCCGACGGCC      60

GGGCGAACGG ATGAGGACTG CTCCACTCTC ACCCAGATAA GCGCGTGGGC CGTTTCATCC     120

GAGCGCCTTT CCGGGCCGCT TCGAAAGACC GCCACGAGGC ACTCTGTGCA AGGGCCAGGC     180

AGTCGCGTTG CAACCGGAGA CGGGACCGGC CCGTTCGGGC GTCGTCTCTT CCCGCTCCAC     240

TTTTTCCAGG CAGCTTCGGC TGCTCCACTC GGAACCGGGA AGCGGAGAT ATG GAT         295
                                                     Met Asp
                                                       1

TAC AAC GTC AAG GAT TTC GGT GCA TTG GGC GAC GGC GTC AGC GAC GAC      343
Tyr Asn Val Lys Asp Phe Gly Ala Leu Gly Asp Gly Val Ser Asp Asp
          5                  10                  15

CGG GCC TCC ATC CAG GCG GCG ATC GAT GCC GCC TAC GCC GCC GGT GGC      391
Arg Ala Ser Ile Gln Ala Ala Ile Asp Ala Ala Tyr Ala Ala Gly Gly
         20                  25                  30

GGT ACC GTC TAC CTG CCG GCC GGC GAG TAC CGG GTC AGC GCC GCC GGG      439
Gly Thr Val Tyr Leu Pro Ala Gly Glu Tyr Arg Val Ser Ala Ala Gly
 35                  40                  45                  50

GAG CCG GGC GAC GGC TGC CTG ATG CTC AAG GAC GGC GTC TAC CTG GCC      487
Glu Pro Gly Asp Gly Cys Leu Met Leu Lys Asp Gly Val Tyr Leu Ala
                 55                  60                  65

GGT GCC GGC ATG GGC GAG ACG GTG ATC AAG CTG ATC GAC GGC TCC GAC      535
Gly Ala Gly Met Gly Glu Thr Val Ile Lys Leu Ile Asp Gly Ser Asp
             70                  75                  80

CAG AAG ATC ACC GGC ATG GTC CGC TCG GCC TAC GGC GAG GAA ACC AGC      583
Gln Lys Ile Thr Gly Met Val Arg Ser Ala Tyr Gly Glu Glu Thr Ser
         85                  90                  95

AAC TTC GGC ATG CGC GAC CTG ACC CTC GAC GGC AAC CGC GAC AAC ACC      631
Asn Phe Gly Met Arg Asp Leu Thr Leu Asp Gly Asn Arg Asp Asn Thr
     100                 105                 110

AGC GGC AAG GTC GAC GGC TGG TTC AAC GGC TAT ATC CCC GGC GGG GAC      679
Ser Gly Lys Val Asp Gly Trp Phe Asn Gly Tyr Ile Pro Gly Gly Asp
115                 120                 125                 130

GGC GCC GAC CGC GAC GTG ACC ATC GAG CGG GTG GAG GTC CGC GAG ATG      727
Gly Ala Asp Arg Asp Val Thr Ile Glu Arg Val Glu Val Arg Glu Met
                 135                 140                 145

TCC GGC TAC GGC TTC GAC CCC CAC GAG CAG ACC ATC AAC CTG ACG ATC      775
Ser Gly Tyr Gly Phe Asp Pro His Glu Gln Thr Ile Asn Leu Thr Ile
             150                 155                 160

CGC GAC AGC GTG GCC CAC GAC AAC GGC CTC GAC GGC TTC GTC GCC GAC      823
Arg Asp Ser Val Ala His Asp Asn Gly Leu Asp Gly Phe Val Ala Asp
         165                 170                 175

TAC CTG GTC GAC AGC GTG TTC GAG AAC AAC GTC GCC TAC GCC AAC GAC      871
Tyr Leu Val Asp Ser Val Phe Glu Asn Asn Val Ala Tyr Ala Asn Asp
     180                 185                 190

CGC CAC GGC TTC AAC GTG GTC ACC AGC ACC CAC GAT TTC GTC ATG ACC      919
Arg His Gly Phe Asn Val Val Thr Ser Thr His Asp Phe Val Met Thr
195                 200                 205                 210

AAC AAC GTC GCC TAC GGC AAC GGC AGC AGC GGC CTG GTG GTG CAG CGG      967
Asn Asn Val Ala Tyr Gly Asn Gly Ser Ser Gly Leu Val Val Gln Arg
                 215                 220                 225

GGT CTG GAG GAC CTC GCG CTG CCC AGC AAC ATC CTG ATC GAC GGC GGC     1015
Gly Leu Glu Asp Leu Ala Leu Pro Ser Asn Ile Leu Ile Asp Gly Gly
             230                 235                 240

GCC TAC TAC GAC AAC GCC CGC GAA GGC GTG CTG CTC AAG ATG ACC AGC     1063
Ala Tyr Tyr Asp Asn Ala Arg Glu Gly Val Leu Leu Lys Met Thr Ser
         245                 250                 255
```

```
GAC ATC ACC CTG CAG AAC GCC GAT ATC CAC GGC AAC GGC TCC TCC GGG    1111
Asp Ile Thr Leu Gln Asn Ala Asp Ile His Gly Asn Gly Ser Ser Gly
    260                 265                 270

GTG CGC GTC TAC GGC GCC CAG GAC GTG CAG ATC CTC GAT AAC CAG ATC    1159
Val Arg Val Tyr Gly Ala Gln Asp Val Gln Ile Leu Asp Asn Gln Ile
275                 280                 285                 290

CAC GAC AAC GCG CAG GCG GCC GCC GTG CCC GAG GTC CTG CTG CAG TCC    1207
His Asp Asn Ala Gln Ala Ala Ala Val Pro Glu Val Leu Leu Gln Ser
                    295                 300                 305

TTC GAC GAT ACC GCC GGG GCG TCC GGC ACC TAC TAC ACG ACC CTG AAC    1255
Phe Asp Asp Thr Ala Gly Ala Ser Gly Thr Tyr Tyr Thr Thr Leu Asn
            310                 315                 320

ACC CGG ATC GAG GGC AAC ACC ATC AGC GGC TCG GCC AAC TCC ACC TAC    1303
Thr Arg Ile Glu Gly Asn Thr Ile Ser Gly Ser Ala Asn Ser Thr Tyr
        325                 330                 335

GGC ATC CAG GAG CGC AAC GAC GGC ACC GAC TAC AGC AGC CTG ATC GAC    1351
Gly Ile Gln Glu Arg Asn Asp Gly Thr Asp Tyr Ser Ser Leu Ile Asp
    340                 345                 350

AAC GAC ATC GCC GGG GTG CAA CAG CCC ATC CAA CTG TAC GGA CCT CAC    1399
Asn Asp Ile Ala Gly Val Gln Gln Pro Ile Gln Leu Tyr Gly Pro His
355                 360                 365                 370

TCG ACG GTA TCC GGC GAA CCC GGC GCG ACA CCG CAA CAG CCG TCC ACG    1447
Ser Thr Val Ser Gly Glu Pro Gly Ala Thr Pro Gln Gln Pro Ser Thr
                375                 380                 385

GGA AGC GAC GGC GAG CCA CTG GTC GGC GGC GAC ACG GAC GAC CAG CTC    1495
Gly Ser Asp Gly Glu Pro Leu Val Gly Gly Asp Thr Asp Asp Gln Leu
            390                 395                 400

CAG GGC GGC TCC GGC GCC GAT CGC CTG GAC GGC GGG GCC GGC GAC GAC    1543
Gln Gly Gly Ser Gly Ala Asp Arg Leu Asp Gly Gly Ala Gly Asp Asp
        405                 410                 415

ATC CTC GAC GGC GGC GCC GGG CGC GAC CGG CTG AGC GGC GGC GCG GGC    1591
Ile Leu Asp Gly Gly Ala Gly Arg Asp Arg Leu Ser Gly Gly Ala Gly
    420                 425                 430

GCC GAC ACC TTC GTG TTC TCC GCC CGC GAG GAC AGC TAC CGT ACC GAC    1639
Ala Asp Thr Phe Val Phe Ser Ala Arg Glu Asp Ser Tyr Arg Thr Asp
435                 440                 445                 450

ACG GCG GTG TTC AAC GAC CTG ATC CTC GAC TTC GAG GCC AGC GAG GAT    1687
Thr Ala Val Phe Asn Asp Leu Ile Leu Asp Phe Glu Ala Ser Glu Asp
                455                 460                 465

CGC ATC GAC CTG TCC GCG CTG GGC TTT TCC GGC CTG GGC GAC GGC TAT    1735
Arg Ile Asp Leu Ser Ala Leu Gly Phe Ser Gly Leu Gly Asp Gly Tyr
            470                 475                 480

GGC GGC ACC CTG CTC CTG AAG ACC AAC GCC GAG GGC ACG CGC ACC TAC    1783
Gly Gly Thr Leu Leu Leu Lys Thr Asn Ala Glu Gly Thr Arg Thr Tyr
        485                 490                 495

CTG AAA AGC TTC GAG GCG GAT GCC GAG GGA CGG CGC TTC GAG GTC GCC    1831
Leu Lys Ser Phe Glu Ala Asp Ala Glu Gly Arg Arg Phe Glu Val Ala
    500                 505                 510

CTG GAC GGC GAC CAC ACG GGC GAT CTT TCC GCC GCC AAT GTG GTC TTC    1879
Leu Asp Gly Asp His Thr Gly Asp Leu Ser Ala Ala Asn Val Val Phe
515                 520                 525                 530

GCC GCG ACC GGG ACG ACC ACC GAA CTC GAA GTG CTC GGC GAC AGC GGC    1927
Ala Ala Thr Gly Thr Thr Thr Glu Leu Glu Val Leu Gly Asp Ser Gly
                535                 540                 545

ACG CAG GCC GGG GCG ATC GTC TAG CGCGTCCCGC TCCGACACAT AGCCGGTCGT    1981
Thr Gln Ala Gly Ala Ile Val *
            550

CGGCAAGGCG GCCGGCCGCC GGCTGCCCCG AAGTTTCCAA TCTAATCTCA CCTACAGACA    2041

GGCGCGTTCC GGTGCGCCCG AGCGCCGCCC CCGGGAACGA CCGGCAGGGC GTGTTTGTGC    2101
```

```
GCAAGGTGCA GGCGGTCGCG CTCGAAGCCA GAGGCAGGGA AAACCTTTTC CGGCAGTCGT      2161

CTCTTCCTTC TCCACTTCCC AGGCAGCCCT GGGCCGAGCA ACACGACGGG ATTAGGAAGC      2221

GGATC ATG GAT TAC AAC GTC AAG GAT TTC GGA GCA CTG GGC GAT GGC          2268
      Met Asp Tyr Asn Val Lys Asp Phe Gly Ala Leu Gly Asp Gly
       1               5                  10

GTC AGC GAC GAC ACG GCG GCC ATC CAG GCG GCG ATC GAC GCC GCC CAC        2316
Val Ser Asp Asp Thr Ala Ala Ile Gln Ala Ala Ile Asp Ala Ala His
 15              20                  25                  30

GCG GCG GGC GGC GGC ACC GTC TAC CTG CCG GCC GGC GAA TAT CGG GTC        2364
Ala Ala Gly Gly Gly Thr Val Tyr Leu Pro Ala Gly Glu Tyr Arg Val
                 35                  40                  45

AGC GGC GGC GAG GAG CCT TCC GAT GGT TGT CTG ACC ATC AAG AGC AAC        2412
Ser Gly Gly Glu Glu Pro Ser Asp Gly Cys Leu Thr Ile Lys Ser Asn
             50                  55                  60

GTC CAT ATC GTC GGC GCC GGG ATG GGC GAG ACG GTG ATC AAG ATG GTC        2460
Val His Ile Val Gly Ala Gly Met Gly Glu Thr Val Ile Lys Met Val
         65                  70                  75

GAC GGC TGG ACG CAG AAC GTC ACC GGC ATG GTG CGC TCG GCC TAC GGC        2508
Asp Gly Trp Thr Gln Asn Val Thr Gly Met Val Arg Ser Ala Tyr Gly
 80                  85                  90

GAG GAA ACC AGC AAC TTC GGC ATG AGC GAC CTG ACC CTC GAC GGC AAC        2556
Glu Glu Thr Ser Asn Phe Gly Met Ser Asp Leu Thr Leu Asp Gly Asn
 95              100                 105                 110

CGC GAC AAC CTG TCC GCC AAG GTC GAC GGC TGG TTC AAC GGC TAC ATC        2604
Arg Asp Asn Leu Ser Ala Lys Val Asp Gly Trp Phe Asn Gly Tyr Ile
                 115                 120                 125

CCC GGC CAG GAC GGC GCC GAT CGC GAC GTG ACC CTG GAG CGG GTG GAA        2652
Pro Gly Gln Asp Gly Ala Asp Arg Asp Val Thr Leu Glu Arg Val Glu
             130                 135                 140

ATC CGC GAG ATG TCC GGC TAC GGT TTC GAC CCC CAC GAG CAG ACC ATC        2700
Ile Arg Glu Met Ser Gly Tyr Gly Phe Asp Pro His Glu Gln Thr Ile
         145                 150                 155

AAC CTG ACG ATC CGC GAC AGC GTG GCC CAC GAC AAC AGC CTC GAC GGC        2748
Asn Leu Thr Ile Arg Asp Ser Val Ala His Asp Asn Ser Leu Asp Gly
 160                 165                 170

TTC GTC GCC GAC TAC CAG GTC GGC GGG GTG TTC GAG AAC AAC GTC TCG        2796
Phe Val Ala Asp Tyr Gln Val Gly Gly Val Phe Glu Asn Asn Val Ser
175                 180                 185                 190

TAC AAC AAC GAC CGC CAC GGC TTC AAC ATC GTC ACC AGC ACC AAC GAC        2844
Tyr Asn Asn Asp Arg His Gly Phe Asn Ile Val Thr Ser Thr Asn Asp
                 195                 200                 205

TTC GTC CTG AGC AAC AAC GTC GCC TAC GGC AAC GGC GGC GCC GGC CTG        2892
Phe Val Leu Ser Asn Asn Val Ala Tyr Gly Asn Gly Gly Ala Gly Leu
             210                 215                 220

GTG GTG CAG CGC GGC TCG TAC GAC CTG CCC CAT CCC TAC GAC ATC CTG        2940
Val Val Gln Arg Gly Ser Tyr Asp Leu Pro His Pro Tyr Asp Ile Leu
         225                 230                 235

ATC GAC GGC GGC GCC TAC TAC GAC AAC GCC TTG GAA GGC GTG CAG CTC        2988
Ile Asp Gly Gly Ala Tyr Tyr Asp Asn Ala Leu Glu Gly Val Gln Leu
 240                 245                 250

AAG ATG GCC CAC GAC GTC ACC CTG CAG AAC GCC GAG ATC TAC GGC AAC        3036
Lys Met Ala His Asp Val Thr Leu Gln Asn Ala Glu Ile Tyr Gly Asn
255                 260                 265                 270

GGC CTG TAC GGG GTG CGC GTC TAC GGC GCC CAG GAC GTG CAG ATC CTC        3084
Gly Leu Tyr Gly Val Arg Val Tyr Gly Ala Gln Asp Val Gln Ile Leu
                 275                 280                 285

GAC AAC CAG ATC CAC GAC AAT TCG CAG AAC GGC GCC TAT GCC GAA GTC        3132
Asp Asn Gln Ile His Asp Asn Ser Gln Asn Gly Ala Tyr Ala Glu Val
             290                 295                 300
```

```
CTG CTG CAG TCC TAC GAC GAC ACC GCC GGG GTG TCC GGC AAC TTT TAC     3180
Leu Leu Gln Ser Tyr Asp Asp Thr Ala Gly Val Ser Gly Asn Phe Tyr
        305                 310                 315

GTC ACC ACC GGC ACC TGG CTC GAA GGC AAC GTC ATC AGC GGC TCG GCC     3228
Val Thr Thr Gly Thr Trp Leu Glu Gly Asn Val Ile Ser Gly Ser Ala
320                 325                 330

AAT TCC ACC TAC GGC ATC CAG GAG CGC GCC GAC GGC ACC GAC TAC AGC     3276
Asn Ser Thr Tyr Gly Ile Gln Glu Arg Ala Asp Gly Thr Asp Tyr Ser
335                 340                 345                 350

AGC CTC TAC GCC AAC AGC ATC GAC GGT GTG CAG ACC GGG GCG GTA CGG     3324
Ser Leu Tyr Ala Asn Ser Ile Asp Gly Val Gln Thr Gly Ala Val Arg
                355                 360                 365

CTG TAT GGC GCC AAC TCG ACG GTT TCC AGC CAG TCC GGC AGT GGC CAG     3372
Leu Tyr Gly Ala Asn Ser Thr Val Ser Ser Gln Ser Gly Ser Gly Gln
        370                 375                 380

CAG GCG ACC CTC GAA GGC AGC GCG GGC AAC GAT GCG CTG AGC GGG ACC     3420
Gln Ala Thr Leu Glu Gly Ser Ala Gly Asn Asp Ala Leu Ser Gly Thr
    385                 390                 395

GAG GCC CAC GAG ACG CTG CTC GGC CAG GCC GGC GAC GAC CGC CTG AAC     3468
Glu Ala His Glu Thr Leu Leu Gly Gln Ala Gly Asp Asp Arg Leu Asn
400                 405                 410

GGC GAT GCC GGC AAC GAC ATC CTC GAC GGC GGG GCA GGG CGC GAC AAC     3516
Gly Asp Ala Gly Asn Asp Ile Leu Asp Gly Gly Ala Gly Arg Asp Asn
415                 420                 425                 430

CTG ACC GGC GGC GCG GGC GCC GAC ACC TTC CGC TTC TCC GCG CGC ACC     3564
Leu Thr Gly Gly Ala Gly Ala Asp Thr Phe Arg Phe Ser Ala Arg Thr
                435                 440                 445

GAC AGC TAC CGC ACC GAC AGC GCC AGC TTC AAC GAC CTG ATC ACC GAC     3612
Asp Ser Tyr Arg Thr Asp Ser Ala Ser Phe Asn Asp Leu Ile Thr Asp
        450                 455                 460

TTC GAC GCC GAC GAG GAC AGC ATC GAC CTG TCC GCG CTG GGC TTC ACC     3660
Phe Asp Ala Asp Glu Asp Ser Ile Asp Leu Ser Ala Leu Gly Phe Thr
    465                 470                 475

GGC CTG GGC GAC GGC TAC AAT GGC ACC CTG CTG CTG AAG ACC AAC GCC     3708
Gly Leu Gly Asp Gly Tyr Asn Gly Thr Leu Leu Leu Lys Thr Asn Ala
480                 485                 490

GAG GGT ACG CGC ACC TAC CTG AAG AGC TAC GAA GCG GAC GCC CAG GGC     3756
Glu Gly Thr Arg Thr Tyr Leu Lys Ser Tyr Glu Ala Asp Ala Gln Gly
495                 500                 505                 510

CGG CGC TTC GAG ATC GCC CTG GAC GGC AAC TTC ACC GGT CTG TTC AAC     3804
Arg Arg Phe Glu Ile Ala Leu Asp Gly Asn Phe Thr Gly Leu Phe Asn
                515                 520                 525

GAC AAC AAC CTG TTG TTC GAC GCC GCT CCG GCC ACC GGT ACC GAG GGC     3852
Asp Asn Asn Leu Leu Phe Asp Ala Ala Pro Ala Thr Gly Thr Glu Gly
        530                 535                 540

AGC GAC AAC CTG CTC GGC ACC GAC GCC GGG GAA ACC CTC CTG GGC TAC     3900
Ser Asp Asn Leu Leu Gly Thr Asp Ala Gly Glu Thr Leu Leu Gly Tyr
    545                 550                 555

GGC GGC AAC GAC ACC CTC AAC GGC GGG GCC GGC GAC GAC ATC CTG GTC     3948
Gly Gly Asn Asp Thr Leu Asn Gly Gly Ala Gly Asp Asp Ile Leu Val
560                 565                 570

GGC GGC GCC GGG CGC GAC AGC CTG ACC GGC GGC GCC GGG GCG GAC GTG     3996
Gly Gly Ala Gly Arg Asp Ser Leu Thr Gly Gly Ala Gly Ala Asp Val
575                 580                 585                 590

TTC CGC TTC GAC GCG CTG TCC GAC AGC CAG CGC AAC TAC ACC ACC GGC     4044
Phe Arg Phe Asp Ala Leu Ser Asp Ser Gln Arg Asn Tyr Thr Thr Gly
                595                 600                 605

GAC AAC CAG GCC GAC CGC ATT CTC GAC TTC GAC CCG ACC CTG GAC AGG     4092
Asp Asn Gln Ala Asp Arg Ile Leu Asp Phe Asp Pro Thr Leu Asp Arg
        610                 615                 620
```

| | | |
|---|---|---|
| ATC GAC GTG TCG GCG CTG GGC TTC ACC GGG CTG GGC AAC GGC CGC AAC<br>Ile Asp Val Ser Ala Leu Gly Phe Thr Gly Leu Gly Asn Gly Arg Asn<br>              625                             630                        635 | 4140 |
| GGC ACC CTC GCC GTG GTG CTC AAC AGC GCC GGC GAC CGC ACC GAT CTG<br>Gly Thr Leu Ala Val Val Leu Asn Ser Ala Gly Asp Arg Thr Asp Leu<br>640                           645                       650 | 4188 |
| AAG AGC TAC GAC ACC GAC GCC AAC GGC TAC AGC TTC GAG CTT TCC CTC<br>Lys Ser Tyr Asp Thr Asp Ala Asn Gly Tyr Ser Phe Glu Leu Ser Leu<br>655                         660                       665                  670 | 4236 |
| GCG GGC AAC TAC CAG GGG CAG CTC AGC GCC GAG CAG TTC GTT TTC GCG<br>Ala Gly Asn Tyr Gln Gly Gln Leu Ser Ala Glu Gln Phe Val Phe Ala<br>                       675                             680                       685 | 4284 |
| ACG TCT CAG GGG GGA CAG ATG ACG ATT ATC GAA GGC ACC GAC GGC AAC<br>Thr Ser Gln Gly Gly Gln Met Thr Ile Ile Glu Gly Thr Asp Gly Asn<br>                   690                             695                       700 | 4332 |
| GAT ACC TTG CAG GGC ACC GAG GCC AAC GAG CGG CTC CTC GGC CTG GAC<br>Asp Thr Leu Gln Gly Thr Glu Ala Asn Glu Arg Leu Leu Gly Leu Asp<br>           705                             710                       715 | 4380 |
| GGC CGG GAC AAC CTG AAC GGC GGC GCC GGC GAC GAC ATC CTC GAC GGC<br>Gly Arg Asp Asn Leu Asn Gly Gly Ala Gly Asp Asp Ile Leu Asp Gly<br>720                         725                       730 | 4428 |
| GGA GCG GGG CGC GAC ACC CTG ACC GGC GGC ACG GGG GCC GAC ACC TTC<br>Gly Ala Gly Arg Asp Thr Leu Thr Gly Gly Thr Gly Ala Asp Thr Phe<br>735                           740                       745                   750 | 4476 |
| CTG TTC TCC ACG CGT ACC GAC AGC TAC CGC ACC GAC AGC GCC AGC TTC<br>Leu Phe Ser Thr Arg Thr Asp Ser Tyr Arg Thr Asp Ser Ala Ser Phe<br>                   755                             760                       765 | 4524 |
| AAC GAC CTG ATC ACC GAC TTC GAT CCC ACC CAG GAC CGC ATC GAC CTG<br>Asn Asp Leu Ile Thr Asp Phe Asp Pro Thr Gln Asp Arg Ile Asp Leu<br>                   770                             775                       780 | 4572 |
| TCC GGC CTG GGC TTC AGC GGT TTC GGC AAC GGC TAC GAC GGC ACC CTG<br>Ser Gly Leu Gly Phe Ser Gly Phe Gly Asn Gly Tyr Asp Gly Thr Leu<br>           785                             790                       795 | 4620 |
| CTG CTG CAG GTC AAC GCC GCG GGC ACC CGC ACC TAC CTG AAG AGT TTC<br>Leu Leu Gln Val Asn Ala Ala Gly Thr Arg Thr Tyr Leu Lys Ser Phe<br>800                         805                       810 | 4668 |
| GAG GCC GAT GCC AAC GGC CAG CGC TTC GAG ATC GCC CTG GAC GGC GAC<br>Glu Ala Asp Ala Asn Gly Gln Arg Phe Glu Ile Ala Leu Asp Gly Asp<br>815                         820                       825                  830 | 4716 |
| TTC AGC GGC CAA TTG GAC AGC GGC AAC GTG ATC TTC GAG CCC GCC GTG<br>Phe Ser Gly Gln Leu Asp Ser Gly Asn Val Ile Phe Glu Pro Ala Val<br>                   835                             840                       845 | 4764 |
| TTC AAT GCC AAG GAC TTC GGC GCG CTG GGC GAC GGC GCC AGC GAC GAC<br>Phe Asn Ala Lys Asp Phe Gly Ala Leu Gly Asp Gly Ala Ser Asp Asp<br>                     850                             855                       860 | 4812 |
| CGG CCG GCC ATC CAG GCG GCG ATC GAC GCC GCC TAC GCG GCC GGT GGC<br>Arg Pro Ala Ile Gln Ala Ala Ile Asp Ala Ala Tyr Ala Ala Gly Gly<br>             865                             870                       875 | 4860 |
| GGC ACC GTC TAC CTG CCG GCC GGC GAG TAC CGG GTC AGC CCC ACC GGG<br>Gly Thr Val Tyr Leu Pro Ala Gly Glu Tyr Arg Val Ser Pro Thr Gly<br>           880                             885                       890 | 4908 |
| GAG CCG GGC GAC GGC TGC CTG ATG CTC AAG GAC GGC GTC TAC CTG GCC<br>Glu Pro Gly Asp Gly Cys Leu Met Leu Lys Asp Gly Val Tyr Leu Ala<br>895                         900                       905                       910 | 4956 |
| GGC GAC GGC ATA GGC GAA ACG GTC ATC AAG CTG ATC GAC GGC TCC GAC<br>Gly Asp Gly Ile Gly Glu Thr Val Ile Lys Leu Ile Asp Gly Ser Asp<br>                   915                             920                       925 | 5004 |
| CAG AAG ATC ACC GGC ATG GTG CGC TCG GCC TAT GGC GAA GAG ACC AGC<br>Gln Lys Ile Thr Gly Met Val Arg Ser Ala Tyr Gly Glu Glu Thr Ser<br>                   930                             935                       940 | 5052 |

-continued

| | |
|---|---|
| AAC TTC GGC ATG AGC GAC CTG ACC CTC GAC GGC AAC CGC GAC AAC ACC<br>Asn Phe Gly Met Ser Asp Leu Thr Leu Asp Gly Asn Arg Asp Asn Thr<br>        945                950                955 | 5100 |
| AGC GGC AAG GTC GAC GGC TGG TTC AAC GGC TAC ATC CCC GGC CAG GAC<br>Ser Gly Lys Val Asp Gly Trp Phe Asn Gly Tyr Ile Pro Gly Gln Asp<br>960                  965                970 | 5148 |
| GGC GCC GAC CGC AAC GTG ACC ATC GAG CGG GTG GAA ATC CGC GAG ATG<br>Gly Ala Asp Arg Asn Val Thr Ile Glu Arg Val Glu Ile Arg Glu Met<br>975                  980                985                990 | 5196 |
| TCC GGC TAT GGC TTC GAT CCG CAC GAG CAG ACC ATC AAC CTG ACG ATC<br>Ser Gly Tyr Gly Phe Asp Pro His Glu Gln Thr Ile Asn Leu Thr Ile<br>        995               1000              1005 | 5244 |
| CGC GAC AGC GTG GCC CAC GAC AAC GGC CTC GAC GGC TTC GTC GCC GAC<br>Arg Asp Ser Val Ala His Asp Asn Gly Leu Asp Gly Phe Val Ala Asp<br>       1010               1015              1020 | 5292 |
| TAC CTG GTC GAC AGC GTG TTC GAG AAC AAC GTC GCC TAC AAC AAC GAC<br>Tyr Leu Val Asp Ser Val Phe Glu Asn Asn Val Ala Tyr Asn Asn Asp<br>       1025               1030              1035 | 5340 |
| CGC CAC GGC TTC AAC ATC GTC ACC AGC ACC TAC GAT TTC GTC ATG ACC<br>Arg His Gly Phe Asn Ile Val Thr Ser Thr Tyr Asp Phe Val Met Thr<br>       1040               1045              1050 | 5388 |
| AAC AAC GTC GCC TAC GGC AAC GGC GGC GCC GGC CTG ACG ATC CAG CGG<br>Asn Asn Val Ala Tyr Gly Asn Gly Gly Ala Gly Leu Thr Ile Gln Arg<br>1055               1060              1065              1070 | 5436 |
| GGC TCG GAG GAC CTG GCC CAG CCG ACC GAT ATC CTG ATC GAC GGC GGC<br>Gly Ser Glu Asp Leu Ala Gln Pro Thr Asp Ile Leu Ile Asp Gly Gly<br>               1075              1080              1085 | 5484 |
| GCC TAC TAC GAC AAC GCC CTG GAA GGC GTG CTG TTC AAG ATG ACC AAC<br>Ala Tyr Tyr Asp Asn Ala Leu Glu Gly Val Leu Phe Lys Met Thr Asn<br>               1090              1095              1100 | 5532 |
| AAC GTC ACC CTG CAG AAC GCC GAG ATC TAC GGC AAC GGC TCC TCC GGC<br>Asn Val Thr Leu Gln Asn Ala Glu Ile Tyr Gly Asn Gly Ser Ser Gly<br>       1105               1110              1115 | 5580 |
| GTG CGC CTG TAC GGC ACG GAG GAC GTG CAG ATC CTC GAC AAC CAG ATC<br>Val Arg Leu Tyr Gly Thr Glu Asp Val Gln Ile Leu Asp Asn Gln Ile<br>1120               1125              1130 | 5628 |
| CAC GAC AAT TCG CAG AAC GGC ACC TAT CCG GAA GTC CTG CTG CAG GCC<br>His Asp Asn Ser Gln Asn Gly Thr Tyr Pro Glu Val Leu Leu Gln Ala<br>1135               1140              1145              1150 | 5676 |
| TTC GAC GAC AGC CAG GTC ACC GGT GAG CTG TAC GAG ACC CTG AAC ACC<br>Phe Asp Asp Ser Gln Val Thr Gly Glu Leu Tyr Glu Thr Leu Asn Thr<br>               1155              1160              1165 | 5724 |
| CGG ATC GAA GGC AAT CTC ATC GAC GCT TCG GAC AAC GCC AAC TAT GCG<br>Arg Ile Glu Gly Asn Leu Ile Asp Ala Ser Asp Asn Ala Asn Tyr Ala<br>               1170              1175              1180 | 5772 |
| GTG CGC GAG CGC GAC GAC GGC AGC GAC TAC ACC ACG CTC GTG GAC AAC<br>Val Arg Glu Arg Asp Asp Gly Ser Asp Tyr Thr Thr Leu Val Asp Asn<br>               1185              1190              1195 | 5820 |
| GAC ATC AGC GGC GGC CAG GTC GCC TCG GTG CAG CTT TCC GGC GCC CAT<br>Asp Ile Ser Gly Gly Gln Val Ala Ser Val Gln Leu Ser Gly Ala His<br>1200               1205              1210 | 5868 |
| TCG AGT CTT TCC GGC GGC ACC GTC GAA GTG CCG CAG GGG ACC GAC GGC<br>Ser Ser Leu Ser Gly Gly Thr Val Glu Val Pro Gln Gly Thr Asp Gly<br>1215               1220              1225              1230 | 5916 |
| AAC GAC GTG CTG GTC GGC AGC GAT GCC AAC GAC CAG CTC TAC GGC GGA<br>Asn Asp Val Leu Val Gly Ser Asp Ala Asn Asp Gln Leu Tyr Gly Gly<br>               1235              1240              1245 | 5964 |
| GCC GGC GAC GAC CGC CTG GAC GGC GGC GCC GGT GAC GAC CTG CTC GAC<br>Ala Gly Asp Asp Arg Leu Asp Gly Gly Ala Gly Asp Asp Leu Leu Asp<br>       1250               1255              1260 | 6012 |

```
GGC GGA GCG GGG CGC GAC GAC CTG ACC GGC GGC ACG GGT GCC GAC ACC        6060
Gly Gly Ala Gly Arg Asp Asp Leu Thr Gly Gly Thr Gly Ala Asp Thr
        1265                1270                1275

TTC GTG TTC GCC GCG CGT ACC GAT AGC TAC CGC ACC GAC GCG GGG GTG        6108
Phe Val Phe Ala Ala Arg Thr Asp Ser Tyr Arg Thr Asp Ala Gly Val
    1280                1285                1290

TTC AAC GAC CTG ATC CTC GAC TTC GAC GCC AGC GAG GAC CGC ATC GAC        6156
Phe Asn Asp Leu Ile Leu Asp Phe Asp Ala Ser Glu Asp Arg Ile Asp
1295                1300                1305                1310

CTG TCC GCC CTG GGT TTC AGC GGC TTC GGC GAC GGC TAC AAC GGC ACC        6204
Leu Ser Ala Leu Gly Phe Ser Gly Phe Gly Asp Gly Tyr Asn Gly Thr
                1315                1320                1325

CTG CTG GTG CAG CTC AGC AGC GCC GGA ACC CGT ACC TAC CTC AAG AGC        6252
Leu Leu Val Gln Leu Ser Ser Ala Gly Thr Arg Thr Tyr Leu Lys Ser
            1330                1335                1340

TAC GAG GAG GAC CTC GAG GGC CGG CGC TTC GAG GTC GCC CTG GAC GGC        6300
Tyr Glu Glu Asp Leu Glu Gly Arg Arg Phe Glu Val Ala Leu Asp Gly
        1345                1350                1355

GAC CAC ACG GGC GAT CTT TCC GCC GCC AAT GTG GTT TTC GCC GAC GAC        6348
Asp His Thr Gly Asp Leu Ser Ala Ala Asn Val Val Phe Ala Asp Asp
    1360                1365                1370

GGC TCG GCC GCC GTG GCG AGC AGC GAT CCC GCC GCC ACA CAG TTG GAG        6396
Gly Ser Ala Ala Val Ala Ser Ser Asp Pro Ala Ala Thr Gln Leu Glu
1375                1380                1385                1390

GTG GTC GGC AGC AGC GGC ACC CAG ACC GAT CAA CTC GCC TGA                6438
Val Val Gly Ser Ser Gly Thr Gln Thr Asp Gln Leu Ala *
                1395                1400

TCCGACCCCG CCCATACCCG CCCGGCCATT CCGGCCGGGC GAACCAATGG TCTTCAGGCC      6498

AGTCTCAGGC ACAGCAGCGC GCGAGCCGCT TCGCTTTGTC CGCCCCCCGC TTTTCTCGCT      6558

GAACGCGACG ATCGCCGGGC GCCGGGGAAG GGTTCGCCGC ATGCCGAGCC GGGGACGGGA      6618

AAAGCCTGTT CGACCAGTCG ACTCTTCCTC CCTTCACTTT CCAGGCAGCC TGCGGGCTGC      6678

GCAGTAACGG AACAGGAAGC AGC ATG GAT TAC AAC GTC AAA GAT TTC GGG          6728
                        Met Asp Tyr Asn Val Lys Asp Phe Gly
                         1               5

GCG CTG GGC GAT GGC GTC AGC GAC GAT ACG GCC GCC ATC CAG GCG GCG        6776
Ala Leu Gly Asp Gly Val Ser Asp Asp Thr Ala Ala Ile Gln Ala Ala
 10                  15                  20                  25

ATC GAT GCC GCC TAC GCG GCC GGC GGC GGC ACC GTC TAC CTG CCG GCC        6824
Ile Asp Ala Ala Tyr Ala Ala Gly Gly Gly Thr Val Tyr Leu Pro Ala
                30                  35                  40

GGC GAA TAC CGG GTC AGC GGC GGC GAG GAG CCT TCC GAT GGT TGC CTG        6872
Gly Glu Tyr Arg Val Ser Gly Gly Glu Glu Pro Ser Asp Gly Cys Leu
            45                  50                  55

ACC ATC AAG AGC AAC GTC CAT ATC GTC GGC GCG GGG ATG GGC GAG ACG        6920
Thr Ile Lys Ser Asn Val His Ile Val Gly Ala Gly Met Gly Glu Thr
        60                  65                  70

GTC ATC AAG CTG GTC GAC GGC TGG GAT CAG GAC GTC ACC GGC ATC GTC        6968
Val Ile Lys Leu Val Asp Gly Trp Asp Gln Asp Val Thr Gly Ile Val
    75                  80                  85

CGC TCG GCC TAC GGC GAG GAG ACC AGC AAC TTC GGC ATG AGC GAC CTG        7016
Arg Ser Ala Tyr Gly Glu Glu Thr Ser Asn Phe Gly Met Ser Asp Leu
 90                  95                 100                 105

ACC CTC GAC GGC AAC CGC GAC AAC ACC AGC GGC AAG GTC GAC GGC TGG        7064
Thr Leu Asp Gly Asn Arg Asp Asn Thr Ser Gly Lys Val Asp Gly Trp
                110                 115                 120

TTC AAC GGC TAC ATT CCC GGC GAG GAC GGC GCC GAC CGC GAC GTG ACC        7112
Phe Asn Gly Tyr Ile Pro Gly Glu Asp Gly Ala Asp Arg Asp Val Thr
            125                 130                 135
```

```
CTG GAG CGG GTG GAA ATC CGT GAA ATG TCC GGT TAC GGT TTC GAT CCG         7160
Leu Glu Arg Val Glu Ile Arg Glu Met Ser Gly Tyr Gly Phe Asp Pro
        140                 145                 150

CAC GAG CAG ACC ATC AAC CTG ACG ATC CGC GAC AGC GTG GCC CAC GAC         7208
His Glu Gln Thr Ile Asn Leu Thr Ile Arg Asp Ser Val Ala His Asp
155                 160                 165

AAC GGC CTC GAC GGC TTC GTC GCC GAT TTC CAG ATC GGC GGG GTG TTC         7256
Asn Gly Leu Asp Gly Phe Val Ala Asp Phe Gln Ile Gly Gly Val Phe
170                 175                 180                 185

GAG AAC AAC GTC TCG TAC AAC AAC GAC CGC CAC GGC TTC AAC ATC GTC         7304
Glu Asn Asn Val Ser Tyr Asn Asn Asp Arg His Gly Phe Asn Ile Val
                190                 195                 200

ACC AGC ACC AAC GAC TTC GTC CTG AGC AAC AAC GTC GCC TAC GGC AAC         7352
Thr Ser Thr Asn Asp Phe Val Leu Ser Asn Asn Val Ala Tyr Gly Asn
        205                 210                 215

GGC GGC GCC GGC CTG GTG GTG CAG CGC GGC TCG TCC GAC GTG GCG CAC         7400
Gly Gly Ala Gly Leu Val Val Gln Arg Gly Ser Ser Asp Val Ala His
220                 225                 230

CCC TAC GAC ATC CTG ATC GAC GGC GGC GCC TAC TAC GAC AAC GGC CTG         7448
Pro Tyr Asp Ile Leu Ile Asp Gly Gly Ala Tyr Tyr Asp Asn Gly Leu
235                 240                 245

GAA GGC GTG CAG ATC AAG ATG GCC CAC GAC GTC ACC CTG CAG AAC GCC         7496
Glu Gly Val Gln Ile Lys Met Ala His Asp Val Thr Leu Gln Asn Ala
250                 255                 260                 265

GAG ATC TAC GGC AAC GGC CTA TAC GGG GTG CGC GTC TAC GGC GCC GAG         7544
Glu Ile Tyr Gly Asn Gly Leu Tyr Gly Val Arg Val Tyr Gly Ala Glu
                270                 275                 280

GAT GTG CAG ATC CTC GAC AAC TAC ATC CAC GAC AAT TCG CAG AAC GGT         7592
Asp Val Gln Ile Leu Asp Asn Tyr Ile His Asp Asn Ser Gln Asn Gly
        285                 290                 295

TCC TAC GCG GAA ATC CTC CTG CAG TCC TAC GAC GAT ACC GCC GGG GTG         7640
Ser Tyr Ala Glu Ile Leu Leu Gln Ser Tyr Asp Asp Thr Ala Gly Val
300                 305                 310

TCC GGC AAT TTC TAC ACC ACC ACC GGC ACC TGG ATC GAA GGC AAC ACC         7688
Ser Gly Asn Phe Tyr Thr Thr Thr Gly Thr Trp Ile Glu Gly Asn Thr
315                 320                 325

ATC GTC GGC TCG GCC AAC TCC ACC TAT GGC ATC CAG GAG CGC GAC GAC         7736
Ile Val Gly Ser Ala Asn Ser Thr Tyr Gly Ile Gln Glu Arg Asp Asp
330                 335                 340                 345

GGC ACC GAC TAC AGC AGC CTC TAC GCC AAC AGC GTC AGC AAT GTG CAG         7784
Gly Thr Asp Tyr Ser Ser Leu Tyr Ala Asn Ser Val Ser Asn Val Gln
                350                 355                 360

AAC GGC TCG GTG CGC CTC TAC GGC GCC AAC TCC GTC GTC TCC GAC CTG         7832
Asn Gly Ser Val Arg Leu Tyr Gly Ala Asn Ser Val Val Ser Asp Leu
        365                 370                 375

CCC GGC ACC GGC CAG CAG GCG ACC CTC GAA GGC ACG GCC GGC AAC GAC         7880
Pro Gly Thr Gly Gln Gln Ala Thr Leu Glu Gly Thr Ala Gly Asn Asp
380                 385                 390

ACG CTT GGC GGC AGC GAC GCC CAC GAG ACG CTG CTC GGG CTG GAC GGC         7928
Thr Leu Gly Gly Ser Asp Ala His Glu Thr Leu Leu Gly Leu Asp Gly
        395                 400                 405

AAC GAC CGC CTG AAC GGC GGC GCC GGC AAC GAC ATC CTC GAC GGC GGC         7976
Asn Asp Arg Leu Asn Gly Gly Ala Gly Asn Asp Ile Leu Asp Gly Gly
410                 415                 420                 425

GCC GGG CGC GAC AAC CTG ACC GGC GGC GCG GGC GCC GAC CTG TTC CGC         8024
Ala Gly Arg Asp Asn Leu Thr Gly Gly Ala Gly Ala Asp Leu Phe Arg
                430                 435                 440

GTC TCC GCG CGC ACC GAC AGC TAC CGC ACC GAC AGC GCC AGC TTC AAC         8072
Val Ser Ala Arg Thr Asp Ser Tyr Arg Thr Asp Ser Ala Ser Phe Asn
        445                 450                 455
```

```
GAC CTG ATC ACC GAC TTC GAC GCC AGC CAG GAC CGC ATC GAC CTG TCC      8120
Asp Leu Ile Thr Asp Phe Asp Ala Ser Gln Asp Arg Ile Asp Leu Ser
        460                 465                 470

GCG CTG GGC TTC ACC GGG CTG GGC GAC GGC TAT AAC GGC ACC CTG CTG      8168
Ala Leu Gly Phe Thr Gly Leu Gly Asp Gly Tyr Asn Gly Thr Leu Leu
475                 480                 485

CTG CAG GTC AGC GCC GAC GGC AGC CGC ACC TAT CTG AAG AGC CTG GAG      8216
Leu Gln Val Ser Ala Asp Gly Ser Arg Thr Tyr Leu Lys Ser Leu Glu
490                 495                 500                 505

GCG GAT GCC GAG GGG CGG CGT TTC GAG ATC GCC CTG GAC GGC AAC TTC      8264
Ala Asp Ala Glu Gly Arg Arg Phe Glu Ile Ala Leu Asp Gly Asn Phe
                510                 515                 520

GCC GGC CTG CTC GGT GCC GGC AAC CTG CTC TTC GAG CGC ACC GCC ATC      8312
Ala Gly Leu Leu Gly Ala Gly Asn Leu Leu Phe Glu Arg Thr Ala Ile
            525                 530                 535

GAG GGG GAT GCC GGC GAC AAC GCC CTG CTC GGT ACC TCG GCC GCC GAG      8360
Glu Gly Asp Ala Gly Asp Asn Ala Leu Leu Gly Thr Ser Ala Ala Glu
        540                 545                 550

ACA TTG CTC GGC CAC GCC GGC AAC GAC ACG CTC GAC GGC GGG GCC GGC      8408
Thr Leu Leu Gly His Ala Gly Asn Asp Thr Leu Asp Gly Gly Ala Gly
555                 560                 565

GAC GAC ATC CTG GTC GGC GGC GCC GGG CGC GAC AGC CTC ACC GGC GGC      8456
Asp Asp Ile Leu Val Gly Gly Ala Gly Arg Asp Ser Leu Thr Gly Gly
570                 575                 580                 585

GCC GGA GCG GAC GTG TTC CGC TTC GAC GCG CTG TCC GAC AGC CAG CGC      8504
Ala Gly Ala Asp Val Phe Arg Phe Asp Ala Leu Ser Asp Ser Gln Arg
                590                 595                 600

AAC TAC GAC ATC GGC GAC AAC CAG GGC GAC CGC ATC GCC GAC TTC GCG      8552
Asn Tyr Asp Ile Gly Asp Asn Gln Gly Asp Arg Ile Ala Asp Phe Ala
            605                 610                 615

GTG GGC GAA GAC AAG CTC GAC GTA TCG GCG CTG GGC TTC ACC GGG CTG      8600
Val Gly Glu Asp Lys Leu Asp Val Ser Ala Leu Gly Phe Thr Gly Leu
        620                 625                 630

GGC GAC GGC TAC AAC GGC ACC CTC GCC CTG GTG CTC AAC AGC GCC GGC      8648
Gly Asp Gly Tyr Asn Gly Thr Leu Ala Leu Val Leu Asn Ser Ala Gly
635                 640                 645

GAC CGC ACC TAC GTG AAA AGC TAC GAG AAC GGC GCC GAC GGC TAC CGC      8696
Asp Arg Thr Tyr Val Lys Ser Tyr Glu Asn Gly Ala Asp Gly Tyr Arg
650                 655                 660                 665

TTC GAG TTT TCC CTC GAC GGC AAC TAT CTG GAG CTA CTC GGC AAC GAG      8744
Phe Glu Phe Ser Leu Asp Gly Asn Tyr Leu Glu Leu Leu Gly Asn Glu
                670                 675                 680

GAT TTC ATC TTC GCC ACG CCC AGC GGC CAG CAA CTC CTC GAA GGC AGC      8792
Asp Phe Ile Phe Ala Thr Pro Ser Gly Gln Gln Leu Leu Glu Gly Ser
            685                 690                 695

GCC GGC AAC GAC AGC CTG CAG GGC ACG GCC GCC GAC GAG GTG ATC CAC      8840
Ala Gly Asn Asp Ser Leu Gln Gly Thr Ala Ala Asp Glu Val Ile His
        700                 705                 710

GGC GGC GGC GGG CGC GAC ACG CTG GCC GGA GGG GCC GGG GCC GAC GTG      8888
Gly Gly Gly Gly Arg Asp Thr Leu Ala Gly Gly Ala Gly Ala Asp Val
715                 720                 725

TTC CGC TTT AGC GAA CTG ACC GAC AGC TAC CGA GAC AGT GCC AGC TAT      8936
Phe Arg Phe Ser Glu Leu Thr Asp Ser Tyr Arg Asp Ser Ala Ser Tyr
730                 735                 740                 745

GCC GAT CTG ATC ACT GAC TTC GAT GCC AGC GAG GAT CGT ATC GAC CTG      8984
Ala Asp Leu Ile Thr Asp Phe Asp Ala Ser Glu Asp Arg Ile Asp Leu
                750                 755                 760

TCC GGC CTC GGC TTC AGC GGT CTG GGC AAC GGC TAC GGC GGT ACC CTG      9032
Ser Gly Leu Gly Phe Ser Gly Leu Gly Asn Gly Tyr Gly Gly Thr Leu
            765                 770                 775
```

```
GCG CTG CAG GTG AAC AGC GCC GGT ACC CGC ACC TAC CTG AAG AGC TTC      9080
Ala Leu Gln Val Asn Ser Ala Gly Thr Arg Thr Tyr Leu Lys Ser Phe
        780                 785                 790

GAG ACC AAC GCC GCC GGC GAG CGT TTC GAG ATC GCC CTG GAC GGC GAC      9128
Glu Thr Asn Ala Ala Gly Glu Arg Phe Glu Ile Ala Leu Asp Gly Asp
795                 800                 805

CTG TCC GCG CTC GGC GGG GCC AAC CTG ATC CTC GAC GCG CGT ACC GTA      9176
Leu Ser Ala Leu Gly Gly Ala Asn Leu Ile Leu Asp Ala Arg Thr Val
810                 815                 820                 825

CTG GCG GGC GGC GAC GGC AAC GAC ACG CTT TCC GGC AGC AGC GCG GCC      9224
Leu Ala Gly Gly Asp Gly Asn Asp Thr Leu Ser Gly Ser Ser Ala Ala
                830                 835                 840

GAG GAA CTG CTC GGC GGG GTC GGC AAC GAC AGC CTG GAC GGC GGC GCC      9272
Glu Glu Leu Leu Gly Gly Val Gly Asn Asp Ser Leu Asp Gly Gly Ala
            845                 850                 855

GGC AAC GAC ATC CTC GAC GGC GGG GCG GGG CGC GAC ACC CTG AGT GGC      9320
Gly Asn Asp Ile Leu Asp Gly Gly Ala Gly Arg Asp Thr Leu Ser Gly
860                 865                 870

GGC AGC GGC AGC GAC ATC TTC CGC TTC GGC GGC GCG CTC GAC AGC TTC      9368
Gly Ser Gly Ser Asp Ile Phe Arg Phe Gly Gly Ala Leu Asp Ser Phe
875                 880                 885

CGC AAC TAC GCC AGC GGG ACG AAC GGC ACC GAC AGC ATC ACC GAC TTC      9416
Arg Asn Tyr Ala Ser Gly Thr Asn Gly Thr Asp Ser Ile Thr Asp Phe
890                 895                 900                 905

ACC CCC GGC GAG GAT CTG ATC GAC CTC TCC GTG CTC GGC TAC ACC GGG      9464
Thr Pro Gly Glu Asp Leu Ile Asp Leu Ser Val Leu Gly Tyr Thr Gly
                910                 915                 920

CTG GGC GAC GGC TAC AAC GGT ACC CTG GCG ATA GTG CTG AAC GAC GCC      9512
Leu Gly Asp Gly Tyr Asn Gly Thr Leu Ala Ile Val Leu Asn Asp Ala
            925                 930                 935

GGC ACC AAG ACC TAC CTG AAA AAC CGC GAG AGC GAC GCC GAA GGC AAC      9560
Gly Thr Lys Thr Tyr Leu Lys Asn Arg Glu Ser Asp Ala Glu Gly Asn
        940                 945                 950

CAG TTC GAG ATC GCC CTG GAG GGC AAC CAC GCC GAC CAG CTC GAT GCG      9608
Gln Phe Glu Ile Ala Leu Glu Gly Asn His Ala Asp Gln Leu Asp Ala
955                 960                 965

AGC GAC TTC ATC TTC GCC ACG GCG GCC GCG ACC ACC GGA ATC GAG GTG      9656
Ser Asp Phe Ile Phe Ala Thr Ala Ala Ala Thr Thr Gly Ile Glu Val
970                 975                 980                 985

GTC GGC GGC AGC GGC ACC CAG ACC GAT CAG CTC GCC TGA TCCGACCCCG      9705
Val Gly Gly Ser Gly Thr Gln Thr Asp Gln Leu Ala  *
                990                 995

CCCGCACCCG CCCGGCCATT CCGGCCGGGC GAACCAATGG CCTTTTGATC AGTCTCAGGC    9765

ACAGCAACGT GTGCGCCGCT TCGCTTGTTC GCCCTCCCGG CCTTGTTTCT CGCTGAAAGC    9825

GACGATCGCC GGGGGCGTGC CGGGCGCGAG AAAAGGTTCG CCGTGTGCAA AGCCGGGGAC    9885

GGGAAAAGCC TGTTCAAGTA GTCGACTCTT CCTTCTCCTT TTTCCTAGAC GGCCTCTTGG    9945

CTGAGCATTA ACGGAACAGG AAGCAGC ATG GAC TTC AAC GTC AAA GAT TTC         9996
                            Met Asp Phe Asn Val Lys Asp Phe
                            1                 5

GGG GCA CTG GGC GAT GGC GCC AGC GAC GAC ACG GCG GCC ATC CAG GCG     10044
Gly Ala Leu Gly Asp Gly Ala Ser Asp Asp Thr Ala Ala Ile Gln Ala
        10                  15                  20

GCG ATC GAT GCC GCC CAC GCG GCG GGC GGC GGC ACC GTC TAC CTG CCG     10092
Ala Ile Asp Ala Ala His Ala Ala Gly Gly Gly Thr Val Tyr Leu Pro
25                  30                  35                  40

GCT GGC GAG TAT CGG GTC AGC GGC GGC GAG GAG CCT TCC GAC GGC GCG     10140
Ala Gly Glu Tyr Arg Val Ser Gly Gly Glu Glu Pro Ser Asp Gly Ala
            45                  50                  55
```

| | |
|---|---|
| CTG ACC ATC AAG AGC AAC GTC TAT ATC GTC GGC GCC GGG ATG GGC GAG<br>Leu Thr Ile Lys Ser Asn Val Tyr Ile Val Gly Ala Gly Met Gly Glu<br>              60                      65                            70 | 10188 |
| ACG GTG ATC AAG ATG GTC GAC GGC TGG ACG CAG AAC GTC ACC GGC ATG<br>Thr Val Ile Lys Met Val Asp Gly Trp Thr Gln Asn Val Thr Gly Met<br>            75                      80                          85 | 10236 |
| GTG CGC TCG GCC TAT GGC GAG GAG ACC AGC AAC TTC GGC ATG AGC GAC<br>Val Arg Ser Ala Tyr Gly Glu Glu Thr Ser Asn Phe Gly Met Ser Asp<br>            90                      95                        100 | 10284 |
| CTG ACC CTC GAC GGC AAC CGC GAC AAC CTG TCC GCC AAG GTC GAC GGC<br>Leu Thr Leu Asp Gly Asn Arg Asp Asn Leu Ser Ala Lys Val Asp Gly<br>105                    110                    115                    120 | 10332 |
| TGG TTC AAC GGC TAC ATT CCC GGC CAG GAC GGT GCC GAT CGC GAC GTG<br>Trp Phe Asn Gly Tyr Ile Pro Gly Gln Asp Gly Ala Asp Arg Asp Val<br>                    125                    130                    135 | 10380 |
| ACC CTG GAG CGG GTG GAA ATC CGC GAA ATG TCC GGT TAC GGT TTC GAT<br>Thr Leu Glu Arg Val Glu Ile Arg Glu Met Ser Gly Tyr Gly Phe Asp<br>                140                    145                    150 | 10428 |
| CCG CAC GAG CAG ACC ATC AAC CTG ACG ATC CGC GAC AGC GTG GCC CAC<br>Pro His Glu Gln Thr Ile Asn Leu Thr Ile Arg Asp Ser Val Ala His<br>                155                    160                    165 | 10476 |
| GAC AAC GGC CTC GAC GGC TTC GTC GCC GAC TAC CAG GTC GGC GGG GTG<br>Asp Asn Gly Leu Asp Gly Phe Val Ala Asp Tyr Gln Val Gly Gly Val<br>170                    175                    180 | 10524 |
| TTC GAG AAC AAC GTC TCG TAC AAC AAC GAC CGC CAC GGC TTC AAC ATC<br>Phe Glu Asn Asn Val Ser Tyr Asn Asn Asp Arg His Gly Phe Asn Ile<br>185                    190                    195                    200 | 10572 |
| GTC ACC AGC ACC AAC GAC TTC GTC CTG AGC AAC AAC GTC GCC TAC GGC<br>Val Thr Ser Thr Asn Asp Phe Val Leu Ser Asn Asn Val Ala Tyr Gly<br>                    205                    210                    215 | 10620 |
| AAC GGC GGC GCC GGC CTG GTG GTG CAG CGC GGC TCG TAC GAC CTG CCC<br>Asn Gly Gly Ala Gly Leu Val Val Gln Arg Gly Ser Tyr Asp Leu Pro<br>                220                    225                    230 | 10668 |
| CAT CCC TAC GAC ATC CTG ATC GAC GGC GGC GCC TAC TAC GAC AAC GCC<br>His Pro Tyr Asp Ile Leu Ile Asp Gly Gly Ala Tyr Tyr Asp Asn Ala<br>                235                    240                    245 | 10716 |
| TTG GAA GGC GTG CAG CTC AAG ATG ACC CAC GAC GTC ACC CTG CAG AAC<br>Leu Glu Gly Val Gln Leu Lys Met Thr His Asp Val Thr Leu Gln Asn<br>250                    255                    260 | 10764 |
| GCC GAG ATC TAT GGC AAC GGC CTG TAC GGG GTG CGC GTC TAC GGC GCC<br>Ala Glu Ile Tyr Gly Asn Gly Leu Tyr Gly Val Arg Val Tyr Gly Ala<br>265                    270                    275                    280 | 10812 |
| CAG GAC GTG CAA CTC CTC GAT AAC CAG ATC CAC GAC AAT TCG CAG AAC<br>Gln Asp Val Gln Leu Leu Asp Asn Gln Ile His Asp Asn Ser Gln Asn<br>                    285                    290                    295 | 10860 |
| GGC GCC TAT GCC GAA GTC CTG CTG CAG TCC TAC GAC GAC ACC GCC GGG<br>Gly Ala Tyr Ala Glu Val Leu Leu Gln Ser Tyr Asp Asp Thr Ala Gly<br>                300                    305                    310 | 10908 |
| GTG TCC GGC AAC TTT TAC GTC ACC ACC GGC ACC TGG CTC GAA GGC AAC<br>Val Ser Gly Asn Phe Tyr Val Thr Thr Gly Thr Trp Leu Glu Gly Asn<br>                315                    320                    325 | 10956 |
| GTC ATC AGC GGC TCG GCC AAT TCC ACC TTC GGC ATC CAG GAG CGC GCC<br>Val Ile Ser Gly Ser Ala Asn Ser Thr Phe Gly Ile Gln Glu Arg Ala<br>                    330                    335                    340 | 11004 |
| GAC GGC ACC GAC TAC AGC AGC CTT TAC GCC AAT ACC ATC GAC GGC GTG<br>Asp Gly Thr Asp Tyr Ser Ser Leu Tyr Ala Asn Thr Ile Asp Gly Val<br>345                    350                    355                    360 | 11052 |
| CAG AAC GGG ACG GTA CGG CTG TAT GGC GCC AAC TCC ACG GTT TCC GAG<br>Gln Asn Gly Thr Val Arg Leu Tyr Gly Ala Asn Ser Thr Val Ser Glu<br>                365                    370                    375 | 11100 |

-continued

| | |
|---|---|
| CAG CCC AGC AGC GGC CAG CAG GCG ACC CTC GAA GGC ACC GCG GGC AAC<br>Gln Pro Ser Ser Gly Gln Gln Ala Thr Leu Glu Gly Thr Ala Gly Asn<br>        380                               385                            390 | 11148 |
| GAC GTG CTC AGC GGA ACG GGT GCC CAC GAG CTG ATT CTC GGC CTG GCC<br>Asp Val Leu Ser Gly Thr Gly Ala His Glu Leu Ile Leu Gly Leu Ala<br>               395                         400                         405 | 11196 |
| GGC AAC GAT CGC CTG GAC GGT GGC GCC GGC GAC GAC ACC CTC GAC GGC<br>Gly Asn Asp Arg Leu Asp Gly Gly Ala Gly Asp Asp Thr Leu Asp Gly<br>      410                           415                         420 | 11244 |
| GGC GCG GGG CGC GAT ACC CTG ACC GGC GGC GCG GGC GCC GAT ACC TTC<br>Gly Ala Gly Arg Asp Thr Leu Thr Gly Gly Ala Gly Ala Asp Thr Phe<br>425                       430                         435                      440 | 11292 |
| CGC TTC TCT GCC CGC GAG GAC AGT CAC CGC ACC GAC AGC GCC AGC TTC<br>Arg Phe Ser Ala Arg Glu Asp Ser His Arg Thr Asp Ser Ala Ser Phe<br>                       445                         450                         455 | 11340 |
| ACC GAC CTG ATC ACC GAC TTC GAC GCC AGC CAG GAC CGC ATC GAC CTC<br>Thr Asp Leu Ile Thr Asp Phe Asp Ala Ser Gln Asp Arg Ile Asp Leu<br>               460                         465                         470 | 11388 |
| TCC GCG CTG GGC TTC ACC GGT CTG GGC AAC GGT TAT GAC GGC ACC CTG<br>Ser Ala Leu Gly Phe Thr Gly Leu Gly Asn Gly Tyr Asp Gly Thr Leu<br>      475                           480                         485 | 11436 |
| GCG GTG ACC ACC GGT TCC GGC GGC ACC CGC ACC TAC CTG AAG AGC TAC<br>Ala Val Thr Thr Gly Ser Gly Gly Thr Arg Thr Tyr Leu Lys Ser Tyr<br>               490                         495                         500 | 11484 |
| GAG GTG GAC GCC CAG GGC CGG CGT TTC GAA ATC GCC CTG GAC GGC AAC<br>Glu Val Asp Ala Gln Gly Arg Arg Phe Glu Ile Ala Leu Asp Gly Asn<br>505                       510                         515                      520 | 11532 |
| TTC GTC GGC CAG TTC AAC GAT GGC AAC CTG TTG TTC GAC GCC GCT CCG<br>Phe Val Gly Gln Phe Asn Asp Gly Asn Leu Leu Phe Asp Ala Ala Pro<br>                       525                         530                        535 | 11580 |
| GTC ACC GGT ACC GAG GGC AAC GAC AAC CTG TCC GGC ACC GAT GCC GGG<br>Val Thr Gly Thr Glu Gly Asn Asp Asn Leu Ser Gly Thr Asp Ala Gly<br>             540                         545                         550 | 11628 |
| GAA ACC CTC CTG GGC TAC GGC GGC AAC GAC ACC CTC AAC GGC GGG GCC<br>Glu Thr Leu Leu Gly Tyr Gly Gly Asn Asp Thr Leu Asn Gly Gly Ala<br>           555                         560                         565 | 11676 |
| GGC AAC GAC ATC CTG GTC GGC GGC GCC GGG CGC GAC ACC CTG ACC GGC<br>Gly Asn Asp Ile Leu Val Gly Gly Ala Gly Arg Asp Thr Leu Thr Gly<br>      570                         575                         580 | 11724 |
| GGC GCC GGG GCG GAC GTG TTC CGC TTC GAG GCG CTG TCC GAC AGC CAG<br>Gly Ala Gly Ala Asp Val Phe Arg Phe Glu Ala Leu Ser Asp Ser Gln<br>585                       590                         595                      600 | 11772 |
| CGC AAC TAC ACC GCC GGC GAC AAC CAG GGC GAT TAC ATC ATC GAC TTC<br>Arg Asn Tyr Thr Ala Gly Asp Asn Gln Gly Asp Tyr Ile Ile Asp Phe<br>                     605                         610                        615 | 11820 |
| GCC GTG GGC GAA GAC AGG ATC GAC GTA TCG GCG CTG GGT TAC ACC GGG<br>Ala Val Gly Glu Asp Arg Ile Asp Val Ser Ala Leu Gly Tyr Thr Gly<br>               620                         625                         630 | 11868 |
| CTG GGC AAC GGC CGC AAC GGC ACC CTC GCC GTG GTG CTC AAC AGC GCC<br>Leu Gly Asn Gly Arg Asn Gly Thr Leu Ala Val Val Leu Asn Ser Ala<br>           635                         640                        645 | 11916 |
| GGC GAC CGC ACC TAC GTG AAG AGC TAC GAC ACT GAC GCC AAC GGC TAT<br>Gly Asp Arg Thr Tyr Val Lys Ser Tyr Asp Thr Asp Ala Asn Gly Tyr<br>      650                         655                         660 | 11964 |
| AAC TTC GAG CTT TCC CTC GCG GGC AAC TAC CAG GGG CTG CTC GGC GCC<br>Asn Phe Glu Leu Ser Leu Ala Gly Asn Tyr Gln Gly Leu Leu Gly Ala<br>665                       670                         675                      680 | 12012 |
| GAA CAG TTC GTC TTC GCC ACG CCC CCG GAA CAG GCG ACC ATC GAG GGA<br>Glu Gln Phe Val Phe Ala Thr Pro Pro Glu Gln Ala Thr Ile Glu Gly<br>                       685                         690                        695 | 12060 |

```
ACC GAC GGC AAC GAC AGC TTG CAA GGG ACC GGG GCC GAC GAA CTG CTC      12108
Thr Asp Gly Asn Asp Ser Leu Gln Gly Thr Gly Ala Asp Glu Leu Leu
            700                 705                 710

CTC GGT CTG GGC GGC CGG GAC AGC CTG AAC GGC GGC GCC GGC GAC GAT      12156
Leu Gly Leu Gly Gly Arg Asp Ser Leu Asn Gly Gly Ala Gly Asp Asp
            715                 720                 725

GTC CTG GAT GGC GGG GCG GAG CGC GAC ACC CTG ACC GGC GGC ACG GGG      12204
Val Leu Asp Gly Gly Ala Glu Arg Asp Thr Leu Thr Gly Gly Thr Gly
        730                 735                 740

GCC GAC ACC TTC CTG TTC TCC GCG CGT ACC GAC AGC TAC CGC ACC GAC      12252
Ala Asp Thr Phe Leu Phe Ser Ala Arg Thr Asp Ser Tyr Arg Thr Asp
745                 750                 755                 760

AGC GCC AGC TTC ACC GAC CTG ATC ACC GAC TTC GAT CCC GCC CAG GAT      12300
Ser Ala Ser Phe Thr Asp Leu Ile Thr Asp Phe Asp Pro Ala Gln Asp
            765                 770                 775

CGC ATC GAC CTG TCC GGC CTG GGC TTC AGC GGT TTC GGC AAC GGC TAC      12348
Arg Ile Asp Leu Ser Gly Leu Gly Phe Ser Gly Phe Gly Asn Gly Tyr
            780                 785                 790

GAC GGC ACC CTG CTG CTG CAG GTC AAC GCC GCG GGC ACC CGC ACC TAC      12396
Asp Gly Thr Leu Leu Leu Gln Val Asn Ala Ala Gly Thr Arg Thr Tyr
            795                 800                 805

CTG AAG AGC CTC GAG GCC GAT GCC GAC GGC CAG CGC TTC GAG ATC GCC      12444
Leu Lys Ser Leu Glu Ala Asp Ala Asp Gly Gln Arg Phe Glu Ile Ala
810                 815                 820

CTG GAC GGC GAC TTC AGC GGC CAG TTG GAC AGC GGC AAC GTG ATC TTC      12492
Leu Asp Gly Asp Phe Ser Gly Gln Leu Asp Ser Gly Asn Val Ile Phe
825                 830                 835                 840

GAG GCC GGC GTG TTC AAT GCC AAG GAC TTC GGC GCG CTG GGC GAC GGC      12540
Glu Ala Gly Val Phe Asn Ala Lys Asp Phe Gly Ala Leu Gly Asp Gly
                845                 850                 855

GCC AGC GAC GAC CGG CCG GCC ATC CAG GCG GCG ATC GAC GCC GCC TAC      12588
Ala Ser Asp Asp Arg Pro Ala Ile Gln Ala Ala Ile Asp Ala Ala Tyr
            860                 865                 870
```

(2) INFORMATION FOR SEQ ID NO:2:

(i) SEQUENCE CHARACTERISTICS:
        (A) LENGTH: 553 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Tyr Asn Val Lys Asp Phe Gly Ala Leu Gly Asp Gly Val Ser
1               5                   10                  15

Asp Asp Arg Ala Ser Ile Gln Ala Ala Ile Asp Ala Ala Tyr Ala Ala
            20                  25                  30

Gly Gly Gly Thr Val Tyr Leu Pro Ala Gly Glu Tyr Arg Val Ser Ala
        35                  40                  45

Ala Gly Glu Pro Gly Asp Gly Cys Leu Met Leu Lys Asp Gly Val Tyr
    50                  55                  60

Leu Ala Gly Ala Gly Met Gly Glu Thr Val Ile Lys Leu Ile Asp Gly
65                  70                  75                  80

Ser Asp Gln Lys Ile Thr Gly Met Val Arg Ser Ala Tyr Gly Glu Glu
                85                  90                  95

Thr Ser Asn Phe Gly Met Arg Asp Leu Thr Leu Asp Gly Asn Arg Asp
            100                 105                 110

Asn Thr Ser Gly Lys Val Asp Gly Trp Phe Asn Gly Tyr Ile Pro Gly
        115                 120                 125
```

-continued

```
Gly Asp Gly Ala Asp Arg Asp Val Thr Ile Glu Arg Val Glu Val Arg
    130                 135                 140

Glu Met Ser Gly Tyr Gly Phe Asp Pro His Glu Gln Thr Ile Asn Leu
145                 150                 155                 160

Thr Ile Arg Asp Ser Val Ala His Asp Asn Gly Leu Asp Gly Phe Val
                165                 170                 175

Ala Asp Tyr Leu Val Asp Ser Val Phe Glu Asn Asn Val Ala Tyr Ala
            180                 185                 190

Asn Asp Arg His Gly Phe Asn Val Val Thr Ser Thr His Asp Phe Val
        195                 200                 205

Met Thr Asn Asn Val Ala Tyr Gly Asn Gly Ser Ser Gly Leu Val Val
    210                 215                 220

Gln Arg Gly Leu Glu Asp Leu Ala Leu Pro Ser Asn Ile Leu Ile Asp
225                 230                 235                 240

Gly Gly Ala Tyr Tyr Asp Asn Ala Arg Glu Gly Val Leu Leu Lys Met
                245                 250                 255

Thr Ser Asp Ile Thr Leu Gln Asn Ala Asp Ile His Gly Asn Gly Ser
            260                 265                 270

Ser Gly Val Arg Val Tyr Gly Ala Gln Asp Val Gln Ile Leu Asp Asn
        275                 280                 285

Gln Ile His Asp Asn Ala Gln Ala Ala Val Pro Glu Val Leu Leu
    290                 295                 300

Gln Ser Phe Asp Asp Thr Ala Gly Ala Ser Gly Thr Tyr Tyr Thr Thr
305                 310                 315                 320

Leu Asn Thr Arg Ile Glu Gly Asn Thr Ile Ser Gly Ser Ala Asn Ser
                325                 330                 335

Thr Tyr Gly Ile Gln Glu Arg Asn Asp Gly Thr Asp Tyr Ser Ser Leu
            340                 345                 350

Ile Asp Asn Asp Ile Ala Gly Val Gln Gln Pro Ile Gln Leu Tyr Gly
        355                 360                 365

Pro His Ser Thr Val Ser Gly Glu Pro Gly Ala Thr Pro Gln Gln Pro
    370                 375                 380

Ser Thr Gly Ser Asp Gly Glu Pro Leu Val Gly Asp Thr Asp Asp
385                 390                 395                 400

Gln Leu Gln Gly Gly Ser Gly Ala Asp Arg Leu Asp Gly Gly Ala Gly
                405                 410                 415

Asp Asp Ile Leu Asp Gly Gly Ala Gly Arg Asp Arg Leu Ser Gly Gly
            420                 425                 430

Ala Gly Ala Asp Thr Phe Val Phe Ser Ala Arg Glu Asp Ser Tyr Arg
        435                 440                 445

Thr Asp Thr Ala Val Phe Asn Asp Leu Ile Leu Asp Phe Glu Ala Ser
    450                 455                 460

Glu Asp Arg Ile Asp Leu Ser Ala Leu Gly Phe Ser Gly Leu Gly Asp
465                 470                 475                 480

Gly Tyr Gly Gly Thr Leu Leu Lys Thr Asn Ala Glu Gly Thr Arg
                485                 490                 495

Thr Tyr Leu Lys Ser Phe Glu Ala Asp Ala Glu Gly Arg Arg Phe Glu
            500                 505                 510

Val Ala Leu Asp Gly Asp His Thr Gly Asp Leu Ser Ala Ala Asn Val
        515                 520                 525

Val Phe Ala Ala Thr Gly Thr Thr Thr Glu Leu Glu Val Leu Gly Asp
    530                 535                 540

Ser Gly Thr Gln Ala Gly Ala Ile Val
545                 550
```

(2) INFORMATION FOR SEQ ID NO:3:

(i) SEQUENCE CHARACTERISTICS:
        (A) LENGTH: 1403 amino acids
        (B) TYPE: amino acid
        (D) TOPOLOGY: linear (ii) MOLECULE TYPE: protein (xi) SEQUENCE DESCRIPTION: SEQ ID NO:3:

```
Met Asp Tyr Asn Val Lys Asp Phe Gly Ala Leu Gly Asp Gly Val Ser
 1               5                  10                  15

Asp Asp Thr Ala Ala Ile Gln Ala Ala Ile Asp Ala Ala His Ala Ala
                20                  25                  30

Gly Gly Gly Thr Val Tyr Leu Pro Ala Gly Glu Tyr Arg Val Ser Gly
                35                  40                  45

Gly Glu Glu Pro Ser Asp Gly Cys Leu Thr Ile Lys Ser Asn Val His
        50                  55                  60

Ile Val Gly Ala Gly Met Gly Glu Thr Val Ile Lys Met Val Asp Gly
65                  70                  75                  80

Trp Thr Gln Asn Val Thr Gly Met Val Arg Ser Ala Tyr Gly Glu Glu
                85                  90                  95

Thr Ser Asn Phe Gly Met Ser Asp Leu Thr Leu Asp Gly Asn Arg Asp
                100                 105                 110

Asn Leu Ser Ala Lys Val Asp Gly Trp Phe Asn Gly Tyr Ile Pro Gly
                115                 120                 125

Gln Asp Gly Ala Asp Arg Asp Val Thr Leu Glu Arg Val Glu Ile Arg
        130                 135                 140

Glu Met Ser Gly Tyr Gly Phe Asp Pro His Glu Gln Thr Ile Asn Leu
145                 150                 155                 160

Thr Ile Arg Asp Ser Val Ala His Asp Asn Ser Leu Asp Gly Phe Val
                165                 170                 175

Ala Asp Tyr Gln Val Gly Gly Val Phe Glu Asn Asn Val Ser Tyr Asn
                180                 185                 190

Asn Asp Arg His Gly Phe Asn Ile Val Thr Ser Thr Asn Asp Phe Val
                195                 200                 205

Leu Ser Asn Asn Val Ala Tyr Gly Asn Gly Gly Ala Gly Leu Val Val
210                 215                 220

Gln Arg Gly Ser Tyr Asp Leu Pro His Pro Tyr Asp Ile Leu Ile Asp
225                 230                 235                 240

Gly Gly Ala Tyr Tyr Asp Asn Ala Leu Glu Gly Val Gln Leu Lys Met
                245                 250                 255

Ala His Asp Val Thr Leu Gln Asn Ala Glu Ile Tyr Gly Asn Gly Leu
                260                 265                 270

Tyr Gly Val Arg Val Tyr Gly Ala Gln Asp Val Gln Ile Leu Asp Asn
                275                 280                 285

Gln Ile His Asp Asn Ser Gln Asn Gly Ala Tyr Ala Glu Val Leu Leu
                290                 295                 300

Gln Ser Tyr Asp Asp Thr Ala Gly Val Ser Gly Asn Phe Tyr Val Thr
305                 310                 315                 320

Thr Gly Thr Trp Leu Glu Gly Asn Val Ile Ser Gly Ser Ala Asn Ser
                325                 330                 335

Thr Tyr Gly Ile Gln Glu Arg Ala Asp Gly Thr Asp Tyr Ser Ser Leu
                340                 345                 350
```

```
Tyr Ala Asn Ser Ile Asp Gly Val Gln Thr Gly Ala Val Arg Leu Tyr
        355                 360                 365

Gly Ala Asn Ser Thr Val Ser Ser Gln Ser Gly Ser Gly Gln Gln Ala
    370                 375                 380

Thr Leu Glu Gly Ser Ala Gly Asn Asp Ala Leu Ser Gly Thr Glu Ala
385                 390                 395                 400

His Glu Thr Leu Leu Gly Gln Ala Gly Asp Asp Arg Leu Asn Gly Asp
                405                 410                 415

Ala Gly Asn Asp Ile Leu Asp Gly Ala Gly Arg Asp Asn Leu Thr
                420                 425                 430

Gly Gly Ala Gly Ala Asp Thr Phe Arg Phe Ser Ala Arg Thr Asp Ser
        435                 440                 445

Tyr Arg Thr Asp Ser Ala Ser Phe Asn Asp Leu Ile Thr Asp Phe Asp
    450                 455                 460

Ala Asp Glu Asp Ser Ile Asp Leu Ser Ala Leu Gly Phe Thr Gly Leu
465                 470                 475                 480

Gly Asp Gly Tyr Asn Gly Thr Leu Leu Leu Lys Thr Asn Ala Glu Gly
                485                 490                 495

Thr Arg Thr Tyr Leu Lys Ser Tyr Glu Ala Asp Ala Gln Gly Arg Arg
                500                 505                 510

Phe Glu Ile Ala Leu Asp Gly Asn Phe Thr Gly Leu Phe Asn Asp Asn
        515                 520                 525

Asn Leu Leu Phe Asp Ala Ala Pro Ala Thr Gly Thr Glu Gly Ser Asp
    530                 535                 540

Asn Leu Leu Gly Thr Asp Ala Gly Glu Thr Leu Leu Gly Tyr Gly Gly
545                 550                 555                 560

Asn Asp Thr Leu Asn Gly Gly Ala Gly Asp Asp Ile Leu Val Gly Gly
                565                 570                 575

Ala Gly Arg Asp Ser Leu Thr Gly Gly Ala Gly Ala Asp Val Phe Arg
                580                 585                 590

Phe Asp Ala Leu Ser Asp Ser Gln Arg Asn Tyr Thr Thr Gly Asp Asn
        595                 600                 605

Gln Ala Asp Arg Ile Leu Asp Phe Asp Pro Thr Leu Asp Arg Ile Asp
    610                 615                 620

Val Ser Ala Leu Gly Phe Thr Gly Leu Gly Asn Gly Arg Asn Gly Thr
625                 630                 635                 640

Leu Ala Val Val Leu Asn Ser Ala Gly Asp Arg Thr Asp Leu Lys Ser
                645                 650                 655

Tyr Asp Thr Asp Ala Asn Gly Tyr Ser Phe Glu Leu Ser Leu Ala Gly
                660                 665                 670

Asn Tyr Gln Gly Gln Leu Ser Ala Glu Gln Phe Val Phe Ala Thr Ser
        675                 680                 685

Gln Gly Gly Gln Met Thr Ile Ile Glu Gly Thr Asp Gly Asn Asp Thr
    690                 695                 700

Leu Gln Gly Thr Glu Ala Asn Glu Arg Leu Leu Gly Leu Asp Gly Arg
705                 710                 715                 720

Asp Asn Leu Asn Gly Gly Ala Gly Asp Asp Ile Leu Asp Gly Gly Ala
                725                 730                 735

Gly Arg Asp Thr Leu Thr Gly Gly Thr Gly Ala Asp Thr Phe Leu Phe
                740                 745                 750

Ser Thr Arg Thr Asp Ser Tyr Arg Thr Asp Ser Ala Ser Phe Asn Asp
        755                 760                 765

Leu Ile Thr Asp Phe Asp Pro Thr Gln Asp Arg Ile Asp Leu Ser Gly
    770                 775                 780
```

```
Leu Gly Phe Ser Gly Phe Gly Asn Gly Tyr Asp Gly Thr Leu Leu
785                 790                 795                 800

Gln Val Asn Ala Ala Gly Thr Arg Thr Tyr Leu Lys Ser Phe Glu Ala
                805                 810                 815

Asp Ala Asn Gly Gln Arg Phe Glu Ile Ala Leu Asp Gly Asp Phe Ser
                820                 825                 830

Gly Gln Leu Asp Ser Gly Asn Val Ile Phe Glu Pro Ala Val Phe Asn
                835                 840                 845

Ala Lys Asp Phe Gly Ala Leu Gly Asp Gly Ala Ser Asp Asp Arg Pro
850                 855                 860

Ala Ile Gln Ala Ala Ile Asp Ala Ala Tyr Ala Ala Gly Gly Gly Thr
865                 870                 875                 880

Val Tyr Leu Pro Ala Gly Glu Tyr Arg Val Ser Pro Thr Gly Glu Pro
                885                 890                 895

Gly Asp Gly Cys Leu Met Leu Lys Asp Gly Val Tyr Leu Ala Gly Asp
                900                 905                 910

Gly Ile Gly Glu Thr Val Ile Lys Leu Ile Asp Gly Ser Asp Gln Lys
                915                 920                 925

Ile Thr Gly Met Val Arg Ser Ala Tyr Gly Glu Glu Thr Ser Asn Phe
930                 935                 940

Gly Met Ser Asp Leu Thr Leu Asp Gly Asn Arg Asp Asn Thr Ser Gly
945                 950                 955                 960

Lys Val Asp Gly Trp Phe Asn Gly Tyr Ile Pro Gly Gln Asp Gly Ala
                965                 970                 975

Asp Arg Asn Val Thr Ile Glu Arg Val Glu Ile Arg Glu Met Ser Gly
                980                 985                 990

Tyr Gly Phe Asp Pro His Glu Gln Thr Ile Asn Leu Thr Ile Arg Asp
                995                 1000                1005

Ser Val Ala His Asp Asn Gly Leu Asp Gly Phe Val Ala Asp Tyr Leu
                1010                1015                1020

Val Asp Ser Val Phe Glu Asn Asn Val Ala Tyr Asn Asn Asp Arg His
1025                1030                1035                1040

Gly Phe Asn Ile Val Thr Ser Thr Tyr Asp Phe Val Met Thr Asn Asn
                1045                1050                1055

Val Ala Tyr Gly Asn Gly Gly Ala Gly Leu Thr Ile Gln Arg Gly Ser
                1060                1065                1070

Glu Asp Leu Ala Gln Pro Thr Asp Ile Leu Ile Asp Gly Gly Ala Tyr
                1075                1080                1085

Tyr Asp Asn Ala Leu Glu Gly Val Leu Phe Lys Met Thr Asn Asn Val
                1090                1095                1100

Thr Leu Gln Asn Ala Glu Ile Tyr Gly Asn Gly Ser Ser Gly Val Arg
1105                1110                1115                1120

Leu Tyr Gly Thr Glu Asp Val Gln Ile Leu Asp Asn Gln Ile His Asp
                1125                1130                1135

Asn Ser Gln Asn Gly Thr Tyr Pro Glu Val Leu Leu Gln Ala Phe Asp
                1140                1145                1150

Asp Ser Gln Val Thr Gly Glu Leu Tyr Glu Thr Leu Asn Thr Arg Ile
                1155                1160                1165

Glu Gly Asn Leu Ile Asp Ala Ser Asp Asn Ala Asn Tyr Ala Val Arg
                1170                1175                1180

Glu Arg Asp Asp Gly Ser Asp Tyr Thr Leu Val Asp Asn Asp Ile
1185                1190                1195                1200
```

-continued

```
Ser Gly Gly Gln Val Ala Ser Val Gln Leu Ser Gly Ala His Ser Ser
                1205                1210                1215

Leu Ser Gly Gly Thr Val Glu Val Pro Gln Gly Thr Asp Gly Asn Asp
            1220                1225                1230

Val Leu Val Gly Ser Asp Ala Asn Asp Gln Leu Tyr Gly Gly Ala Gly
1235                1240                1245

Asp Asp Arg Leu Asp Gly Gly Ala Gly Asp Leu Leu Asp Gly Gly
        1250                1255                1260

Ala Gly Arg Asp Asp Leu Thr Gly Gly Thr Gly Ala Asp Thr Phe Val
1265                1270                1275                1280

Phe Ala Ala Arg Thr Asp Ser Tyr Arg Thr Asp Ala Gly Val Phe Asn
                1285                1290                1295

Asp Leu Ile Leu Asp Phe Asp Ala Ser Glu Asp Arg Ile Asp Leu Ser
            1300                1305                1310

Ala Leu Gly Phe Ser Gly Phe Gly Asp Gly Tyr Asn Gly Thr Leu Leu
        1315                1320                1325

Val Gln Leu Ser Ser Ala Gly Thr Arg Thr Tyr Leu Lys Ser Tyr Glu
    1330                1335                1340

Glu Asp Leu Glu Gly Arg Arg Phe Glu Val Ala Leu Asp Gly Asp His
1345                1350                1355                1360

Thr Gly Asp Leu Ser Ala Ala Asn Val Val Phe Ala Asp Gly Ser
                1365                1370                1375

Ala Ala Val Ala Ser Ser Asp Pro Ala Ala Thr Gln Leu Glu Val Val
            1380                1385                1390

Gly Ser Ser Gly Thr Gln Thr Asp Gln Leu Ala
        1395                1400

(2) INFORMATION FOR SEQ ID NO:4:

(i) SEQUENCE CHARACTERISTICS:
        (A) LENGTH:  997 amino acids
        (B) TYPE: amino acid
        (D) TOPOLOGY: linear (ii) MOLECULE TYPE: protein (xi) SEQUENCE DESCRIPTION: SEQ ID NO:4:

Met Asp Tyr Asn Val Lys Asp Phe Gly Ala Leu Gly Asp Gly Val Ser
1               5                   10                  15

Asp Asp Thr Ala Ala Ile Gln Ala Ala Ile Asp Ala Ala Tyr Ala Ala
            20                  25                  30

Gly Gly Gly Thr Val Tyr Leu Pro Ala Gly Glu Tyr Arg Val Ser Gly
        35                  40                  45

Gly Glu Glu Pro Ser Asp Gly Cys Leu Thr Ile Lys Ser Asn Val His
    50                  55                  60

Ile Val Gly Ala Gly Met Gly Glu Thr Val Ile Lys Leu Val Asp Gly
65                  70                  75                  80

Trp Asp Gln Asp Val Thr Gly Ile Val Arg Ser Ala Tyr Gly Glu Glu
                85                  90                  95

Thr Ser Asn Phe Gly Met Ser Asp Leu Thr Leu Asp Gly Asn Arg Asp
            100                 105                 110

Asn Thr Ser Gly Lys Val Asp Gly Trp Phe Asn Gly Tyr Ile Pro Gly
        115                 120                 125

Glu Asp Gly Ala Asp Arg Asp Val Thr Leu Glu Arg Val Glu Ile Arg
    130                 135                 140

Glu Met Ser Gly Tyr Gly Phe Asp Pro His Glu Gln Thr Ile Asn Leu
145                 150                 155                 160
```

-continued

```
Thr Ile Arg Asp Ser Val Ala His Asp Asn Gly Leu Asp Gly Phe Val
            165                 170                 175
Ala Asp Phe Gln Ile Gly Gly Val Phe Glu Asn Asn Val Ser Tyr Asn
                180                 185                 190
Asn Asp Arg His Gly Phe Asn Ile Val Thr Ser Thr Asn Asp Phe Val
            195                 200                 205
Leu Ser Asn Asn Val Ala Tyr Gly Asn Gly Gly Ala Gly Leu Val Val
210                 215                 220
Gln Arg Gly Ser Ser Asp Val Ala His Pro Tyr Asp Ile Leu Ile Asp
225                 230                 235                 240
Gly Gly Ala Tyr Tyr Asp Asn Gly Leu Glu Gly Val Gln Ile Lys Met
                245                 250                 255
Ala His Asp Val Thr Leu Gln Asn Ala Glu Ile Tyr Gly Asn Gly Leu
            260                 265                 270
Tyr Gly Val Arg Val Tyr Gly Ala Glu Asp Val Gln Ile Leu Asp Asn
            275                 280                 285
Tyr Ile His Asp Asn Ser Gln Asn Gly Ser Tyr Ala Glu Ile Leu Leu
            290                 295                 300
Gln Ser Tyr Asp Asp Thr Ala Gly Val Ser Gly Asn Phe Tyr Thr Thr
305                 310                 315                 320
Thr Gly Thr Trp Ile Glu Gly Asn Thr Ile Val Gly Ser Ala Asn Ser
                325                 330                 335
Thr Tyr Gly Ile Gln Glu Arg Asp Asp Gly Thr Asp Tyr Ser Ser Leu
            340                 345                 350
Tyr Ala Asn Ser Val Ser Asn Val Gln Asn Gly Ser Val Arg Leu Tyr
            355                 360                 365
Gly Ala Asn Ser Val Val Ser Asp Leu Pro Gly Thr Gly Gln Gln Ala
            370                 375                 380
Thr Leu Glu Gly Thr Ala Gly Asn Asp Thr Leu Gly Gly Ser Asp Ala
385                 390                 395                 400
His Glu Thr Leu Leu Gly Leu Asp Gly Asn Asp Arg Leu Asn Gly Gly
                405                 410                 415
Ala Gly Asn Asp Ile Leu Asp Gly Gly Ala Gly Arg Asp Asn Leu Thr
            420                 425                 430
Gly Gly Ala Gly Ala Asp Leu Phe Arg Val Ser Ala Arg Thr Asp Ser
            435                 440                 445
Tyr Arg Thr Asp Ser Ala Ser Phe Asn Asp Leu Ile Thr Asp Phe Asp
            450                 455                 460
Ala Ser Gln Asp Arg Ile Asp Leu Ser Ala Leu Gly Phe Thr Gly Leu
465                 470                 475                 480
Gly Asp Gly Tyr Asn Gly Thr Leu Leu Leu Gln Val Ser Ala Asp Gly
                485                 490                 495
Ser Arg Thr Tyr Leu Lys Ser Leu Glu Ala Asp Ala Glu Gly Arg Arg
            500                 505                 510
Phe Glu Ile Ala Leu Asp Gly Asn Phe Ala Gly Leu Leu Gly Ala Gly
            515                 520                 525
Asn Leu Leu Phe Glu Arg Thr Ala Ile Glu Gly Asp Ala Gly Asp Asn
            530                 535                 540
Ala Leu Leu Gly Thr Ser Ala Ala Glu Thr Leu Leu Gly His Ala Gly
545                 550                 555                 560
Asn Asp Thr Leu Asp Gly Gly Ala Gly Asp Asp Ile Leu Val Gly Gly
                565                 570                 575
```

-continued

```
Ala Gly Arg Asp Ser Leu Thr Gly Gly Ala Gly Ala Asp Val Phe Arg
            580                 585                 590

Phe Asp Ala Leu Ser Asp Ser Gln Arg Asn Tyr Asp Ile Gly Asp Asn
            595                 600                 605

Gln Gly Asp Arg Ile Ala Asp Phe Ala Val Gly Glu Asp Lys Leu Asp
610                 615                 620

Val Ser Ala Leu Gly Phe Thr Gly Leu Gly Asp Gly Tyr Asn Gly Thr
625                 630                 635                 640

Leu Ala Leu Val Leu Asn Ser Ala Gly Asp Arg Thr Tyr Val Lys Ser
                645                 650                 655

Tyr Glu Asn Gly Ala Asp Gly Tyr Arg Phe Glu Phe Ser Leu Asp Gly
            660                 665                 670

Asn Tyr Leu Glu Leu Leu Gly Asn Glu Asp Phe Ile Phe Ala Thr Pro
            675                 680                 685

Ser Gly Gln Gln Leu Leu Glu Gly Ser Ala Gly Asn Asp Ser Leu Gln
690                 695                 700

Gly Thr Ala Ala Asp Glu Val Ile His Gly Gly Gly Arg Asp Thr
705                 710                 715                 720

Leu Ala Gly Gly Ala Gly Ala Asp Val Phe Arg Phe Ser Glu Leu Thr
                725                 730                 735

Asp Ser Tyr Arg Asp Ser Ala Ser Tyr Ala Asp Leu Ile Thr Asp Phe
            740                 745                 750

Asp Ala Ser Glu Asp Arg Ile Asp Leu Ser Gly Leu Gly Phe Ser Gly
            755                 760                 765

Leu Gly Asn Gly Tyr Gly Gly Thr Leu Ala Leu Gln Val Asn Ser Ala
770                 775                 780

Gly Thr Arg Thr Tyr Leu Lys Ser Phe Glu Thr Asn Ala Ala Gly Glu
785                 790                 795                 800

Arg Phe Glu Ile Ala Leu Asp Gly Asp Leu Ser Ala Leu Gly Gly Ala
                805                 810                 815

Asn Leu Ile Leu Asp Ala Arg Thr Val Leu Ala Gly Gly Asp Gly Asn
            820                 825                 830

Asp Thr Leu Ser Gly Ser Ser Ala Glu Glu Leu Leu Gly Gly Val
            835                 840                 845

Gly Asn Asp Ser Leu Asp Gly Gly Ala Gly Asn Asp Ile Leu Asp Gly
850                 855                 860

Gly Ala Gly Arg Asp Thr Leu Ser Gly Gly Ser Gly Ser Asp Ile Phe
865                 870                 875                 880

Arg Phe Gly Gly Ala Leu Asp Ser Phe Arg Asn Tyr Ala Ser Gly Thr
                885                 890                 895

Asn Gly Thr Asp Ser Ile Thr Asp Phe Thr Pro Gly Glu Asp Leu Ile
            900                 905                 910

Asp Leu Ser Val Leu Gly Tyr Thr Gly Leu Gly Asp Gly Tyr Asn Gly
            915                 920                 925

Thr Leu Ala Ile Val Leu Asn Asp Ala Gly Thr Lys Thr Tyr Leu Lys
930                 935                 940

Asn Arg Glu Ser Asp Ala Glu Gly Asn Gln Phe Glu Ile Ala Leu Glu
945                 950                 955                 960

Gly Asn His Ala Asp Gln Leu Asp Ala Ser Asp Phe Ile Phe Ala Thr
                965                 970                 975

Ala Ala Ala Thr Thr Gly Ile Glu Val Val Gly Gly Ser Gly Thr Gln
            980                 985                 990

Thr Asp Gln Leu Ala
            995
```

(2) INFORMATION FOR SEQ ID NO:5:

(i) SEQUENCE CHARACTERISTICS:
        (A) LENGTH: 872 amino acids
        (B) TYPE: amino acid
        (D) TOPOLOGY: linear (ii) MOLECULE TYPE: protein (xi) SEQUENCE DESCRIPTION: SEQ ID NO:5:

```
Met Asp Phe Asn Val Lys Asp Phe Gly Ala Leu Gly Asp Gly Ala Ser
 1               5                  10                  15

Asp Asp Thr Ala Ala Ile Gln Ala Ala Ile Asp Ala Ala His Ala Ala
            20                  25                  30

Gly Gly Gly Thr Val Tyr Leu Pro Ala Gly Glu Tyr Arg Val Ser Gly
        35                  40                  45

Gly Glu Glu Pro Ser Asp Gly Ala Leu Thr Ile Lys Ser Asn Val Tyr
    50                  55                  60

Ile Val Gly Ala Gly Met Gly Glu Thr Val Ile Lys Met Val Asp Gly
65                  70                  75                  80

Trp Thr Gln Asn Val Thr Gly Met Val Arg Ser Ala Tyr Gly Glu Glu
                85                  90                  95

Thr Ser Asn Phe Gly Met Ser Asp Leu Thr Leu Asp Gly Asn Arg Asp
            100                 105                 110

Asn Leu Ser Ala Lys Val Asp Gly Trp Phe Asn Gly Tyr Ile Pro Gly
        115                 120                 125

Gln Asp Gly Ala Asp Arg Asp Val Thr Leu Glu Arg Val Glu Ile Arg
    130                 135                 140

Glu Met Ser Gly Tyr Gly Phe Asp Pro His Glu Gln Thr Ile Asn Leu
145                 150                 155                 160

Thr Ile Arg Asp Ser Val Ala His Asp Asn Gly Leu Asp Gly Phe Val
                165                 170                 175

Ala Asp Tyr Gln Val Gly Gly Val Phe Glu Asn Asn Val Ser Tyr Asn
            180                 185                 190

Asn Asp Arg His Gly Phe Asn Ile Val Thr Ser Thr Asn Asp Phe Val
        195                 200                 205

Leu Ser Asn Asn Val Ala Tyr Gly Asn Gly Gly Ala Gly Leu Val Val
    210                 215                 220

Gln Arg Gly Ser Tyr Asp Leu Pro His Pro Tyr Asp Ile Leu Ile Asp
225                 230                 235                 240

Gly Gly Ala Tyr Tyr Asp Asn Ala Leu Glu Gly Val Gln Leu Lys Met
                245                 250                 255

Thr His Asp Val Thr Leu Gln Asn Ala Glu Ile Tyr Gly Asn Gly Leu
            260                 265                 270

Tyr Gly Val Arg Val Tyr Gly Ala Gln Asp Val Gln Leu Leu Asp Asn
        275                 280                 285

Gln Ile His Asp Asn Ser Gln Asn Gly Ala Tyr Ala Glu Val Leu Leu
    290                 295                 300

Gln Ser Tyr Asp Asp Thr Ala Gly Val Ser Gly Asn Phe Tyr Val Thr
305                 310                 315                 320

Thr Gly Thr Trp Leu Glu Gly Asn Val Ile Ser Gly Ser Ala Asn Ser
                325                 330                 335

Thr Phe Gly Ile Gln Glu Arg Ala Asp Gly Thr Asp Tyr Ser Ser Leu
            340                 345                 350
```

```
Tyr Ala Asn Thr Ile Asp Gly Val Gln Asn Gly Thr Val Arg Leu Tyr
        355                 360                 365

Gly Ala Asn Ser Thr Val Ser Glu Gln Pro Ser Ser Gly Gln Gln Ala
        370                 375                 380

Thr Leu Glu Gly Thr Ala Gly Asn Asp Val Leu Ser Gly Thr Gly Ala
385                 390                 395                 400

His Glu Leu Ile Leu Gly Leu Ala Gly Asn Asp Arg Leu Asp Gly Gly
                405                 410                 415

Ala Gly Asp Asp Thr Leu Asp Gly Gly Ala Gly Arg Asp Thr Leu Thr
                420                 425                 430

Gly Gly Ala Gly Ala Asp Thr Phe Arg Phe Ser Ala Arg Glu Asp Ser
                435                 440                 445

His Arg Thr Asp Ser Ala Ser Phe Thr Asp Leu Ile Thr Asp Phe Asp
        450                 455                 460

Ala Ser Gln Asp Arg Ile Asp Leu Ser Ala Leu Gly Phe Thr Gly Leu
465                 470                 475                 480

Gly Asn Gly Tyr Asp Gly Thr Leu Ala Val Thr Thr Gly Ser Gly Gly
                485                 490                 495

Thr Arg Thr Tyr Leu Lys Ser Tyr Glu Val Asp Ala Gln Gly Arg Arg
                500                 505                 510

Phe Glu Ile Ala Leu Asp Gly Asn Phe Val Gly Gln Phe Asn Asp Gly
        515                 520                 525

Asn Leu Leu Phe Asp Ala Ala Pro Val Thr Gly Thr Glu Gly Asn Asp
        530                 535                 540

Asn Leu Ser Gly Thr Asp Ala Gly Glu Thr Leu Leu Gly Tyr Gly Gly
545                 550                 555                 560

Asn Asp Thr Leu Asn Gly Ala Gly Asn Asp Ile Leu Val Gly Gly
                565                 570                 575

Ala Gly Arg Asp Thr Leu Thr Gly Gly Ala Gly Ala Asp Val Phe Arg
                580                 585                 590

Phe Glu Ala Leu Ser Asp Ser Gln Arg Asn Tyr Thr Ala Gly Asp Asn
        595                 600                 605

Gln Gly Asp Tyr Ile Ile Asp Phe Ala Val Gly Glu Asp Arg Ile Asp
        610                 615                 620

Val Ser Ala Leu Gly Tyr Thr Gly Leu Gly Asn Gly Arg Asn Gly Thr
625                 630                 635                 640

Leu Ala Val Val Leu Asn Ser Ala Gly Asp Arg Thr Tyr Val Lys Ser
                645                 650                 655

Tyr Asp Thr Asp Ala Asn Gly Tyr Asn Phe Glu Leu Ser Leu Ala Gly
                660                 665                 670

Asn Tyr Gln Gly Leu Leu Gly Ala Glu Gln Phe Val Phe Ala Thr Pro
        675                 680                 685

Pro Glu Gln Ala Thr Ile Glu Gly Thr Asp Gly Asn Asp Ser Leu Gln
        690                 695                 700

Gly Thr Gly Ala Asp Glu Leu Leu Gly Leu Gly Gly Arg Asp Ser
705                 710                 715                 720

Leu Asn Gly Gly Ala Gly Asp Val Leu Asp Gly Gly Ala Glu Arg
                725                 730                 735

Asp Thr Leu Thr Gly Gly Thr Gly Ala Asp Thr Phe Leu Phe Ser Ala
                740                 745                 750

Arg Thr Asp Ser Tyr Arg Thr Asp Ser Ala Ser Phe Thr Asp Leu Ile
                755                 760                 765

Thr Asp Phe Asp Pro Ala Gln Asp Arg Ile Asp Leu Ser Gly Leu Gly
        770                 775                 780
```

```
Phe Ser Gly Phe Gly Asn Gly Tyr Asp Gly Thr Leu Leu Gln Val
785                 790                 795                 800

Asn Ala Ala Gly Thr Arg Thr Tyr Leu Lys Ser Leu Glu Ala Asp Ala
                805                 810                 815

Asp Gly Gln Arg Phe Glu Ile Ala Leu Asp Gly Asp Phe Ser Gly Gln
                820                 825                 830

Leu Asp Ser Gly Asn Val Ile Phe Glu Ala Gly Val Phe Asn Ala Lys
                835                 840                 845

Asp Phe Gly Ala Leu Gly Asp Gly Ala Ser Asp Asp Arg Pro Ala Ile
850                 855                 860

Gln Ala Ala Ile Asp Ala Ala Tyr
865                 870
```

(2) INFORMATION FOR SEQ ID NO:6:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Met Asp Tyr Asn Val Lys Asp Phe Gly Ala Leu Gly Asp Gly Val
1               5                   10                  15
```

(2) INFORMATION FOR SEQ ID NO:7:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

```
ATGGATTACA ACGTCAAGGA TTTCGGGGCG CTGGGCGATG GCGTCAGCGA CGACACGGCG     60

GCCATCCAGG CGGCGATCGA TGCCGCCTAC GCGGCCGGCG GCGGCACCGT CTACCTGCCG    120

GCCGGCGAGT ACCGGGTCAG CGGCGGCGAG GAGCCTTCCG ACGGCTGCCT GACCATCAAG    180

AGCAACGTCT ATATCGTCGG CGCCGGGATG GGCGAGACGG TGATCAAGCT GGTCGACGGC    240

TGGGAGCAGA ACGTCACCGG CATGGTGCGC TCGGCCTACG GCGAGGAGAC CAGCAACTTC    300

GGCATGAGCG ACCTGACCCT CGACGGCAAC CGCGACAACA CCAGCGGCAA GGTCGACGGC    360

TGGTTCAACG GCTACATCCC CGGCCAGGAC GGCGCCGACC GCGACGTGAC CCTGGAGCGG    420

GTGGAAATCC GCGAGATGTC CGGCTACGGT TTCGATCCGC ACGAGCAGAC CATCAACCTG    480

ACGATCCGCG ACAGCGTGGC CCACGACAAC GGCCTCGACG GCTTCGTCGC CGACTACCAG    540

GTCGGCGGGG TGTTCGAGAA CAACGTCTCG TACAACAACG ACCGCCACGG CTTCAACATC    600

GTCACCAGCA CCAACGACTT CGTCCTGAGC AACAACGTCG CCTACGGCAA CGGCGGCGCC    660

GGCCTGGTGG TGCAGCGCGG CTCGTACGAC CTGGCCCAGC CCTACGACAT CCTGATCGAC    720

GGCGGCGCCT ACTACGACAA CGCCCTGGAA GGCGTGCAGC TCAAGATGAC CCACGACGTC    780

ACCCTGCAGA ACGCCGAGAT CTACGGCAAC GGCCTCTACG GGGTGCGCGT CTACGGCGCC    840

CAGGACGTGC AGATCCTCGA CAACCAGATC CACGACAATT CGCAGAACGG CGCCTATGCC    900

GAAGTCCTGC TGCAGTCCTA CGACGACACC GCCGGGGTGT CCGGCAACTT CTACGCCACC    960
```

```
ACCGGCACCT GGATCGAAGG CAACATCATC AGCGGCTCGG CCAACTCCAC CTACGGCATC      1020

CAGGAGCGCG ACGACGGCAC CGACTACAGC AGCCTCTACG CCAACAACAT CGGCGGTGTG      1080

CAGAACGGGT CGGTACGGCT GTACGGCGCC AACTCGACGG TTTCCGGCCA GCCCGGCACC      1140

GGCCAGCAGG CGACC                                                      1155
```

(2) INFORMATION FOR SEQ ID NO:8:

(i) SEQUENCE CHARACTERISTICS:
        (A) LENGTH: 385 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Met Asp Phe Asn Val Lys Asp Phe Gly Ala Leu Gly Asp Gly Ala Ser
1               5                   10                  15

Asp Asp Thr Ala Ala Ile Gln Ala Ala Ile Asp Ala Ala Tyr Ala Ala
                20                  25                  30

Gly Gly Gly Thr Val Tyr Leu Pro Ala Gly Glu Tyr Arg Val Ser Gly
            35                  40                  45

Gly Glu Glu Pro Ser Asp Gly Cys Leu Thr Ile Lys Ser Asn Val Tyr
        50                  55                  60

Ile Val Gly Ala Gly Met Gly Glu Thr Val Ile Lys Leu Val Asp Gly
65                  70                  75                  80

Trp Asp Gln Asn Val Thr Gly Met Val Arg Ser Ala Tyr Gly Glu Glu
                85                  90                  95

Thr Ser Asn Phe Gly Met Ser Asp Leu Thr Leu Asp Gly Asn Arg Asp
                100                 105                 110

Asn Thr Ser Gly Lys Val Asp Gly Trp Phe Asn Gly Tyr Ile Pro Gly
            115                 120                 125

Gln Asp Gly Ala Asp Arg Asp Val Thr Leu Glu Arg Val Glu Ile Arg
        130                 135                 140

Glu Met Ser Gly Tyr Gly Phe Asp Pro His Glu Gln Thr Ile Asn Leu
145                 150                 155                 160

Thr Ile Arg Asp Ser Val Ala His Asp Asn Gly Leu Asp Gly Phe Val
                165                 170                 175

Ala Asp Tyr Gln Val Gly Gly Val Phe Glu Asn Asn Val Ser Tyr Asn
                180                 185                 190

Asn Asp Arg His Gly Phe Asn Ile Val Thr Ser Thr Asn Asp Phe Val
            195                 200                 205

Leu Ser Asn Asn Val Ala Tyr Gly Asn Gly Gly Ala Gly Leu Val Val
        210                 215                 220

Gln Arg Gly Ser Glu Asp Leu Ala His Pro Tyr Asp Ile Leu Ile Asp
225                 230                 235                 240

Gly Gly Ala Tyr Tyr Asp Asn Ala Leu Glu Gly Val Gln Leu Lys Met
                245                 250                 255

Thr His Asp Val Thr Leu Gln Asn Ala Glu Ile Tyr Gly Asn Gly Leu
                260                 265                 270

Tyr Gly Val Arg Val Tyr Gly Ala Gln Asp Val Gln Ile Leu Asp Asn
            275                 280                 285

Gln Ile His Asp Asn Ser Gln Asn Gly Ala Tyr Ala Glu Val Leu Leu
        290                 295                 300

Gln Ser Tyr Asp Asp Thr Ala Gly Val Ser Gly Asn Phe Tyr Thr Thr
305                 310                 315                 320
```

Thr Gly Thr Trp Ile Glu Gly Asn Thr Ile Ser Gly Ser Ala Asn Ser
            325                 330                 335

Thr Tyr Gly Ile Gln Glu Arg Ala Asp Gly Thr Asp Tyr Ser Ser Leu
            340                 345                 350

Tyr Ala Asn Asp Ile Asp Gly Val Gln Thr Gly Ser Val Arg Leu Tyr
            355                 360                 365

Gly Ala Asn Ser Thr Val Ser Gly Gln Pro Gly Ser Gly Gln Gln Ala
    370                 375                 380

Thr

385

(2) INFORMATION FOR SEQ ID NO:9:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
CTCGAAGGCA CCGACGGCAA CGACACGCTG CGCGGCACCG AGGCCGACGA GACGCTCCTC      60

GGCCAGGCCG GCAACGACCG CCTGAACGGC GGCGCCGGCG ACGACATCCT CGACGGCGGC     120

GCCGGGCGCG ACACCCTGAC CGGCGGCGCG GGCGCCGACA CCTTCCGCTT CTCCGCGCGG     180

ACCGACAGCT ACCGCACCGA CAGCGCCGGC GACAGCTTCA ACGACCTGAT CACCGACTTC     240

GACGCCAGCG AGGACCGCAT CGACCTGTCC GCGCTGGGCT TCACCGGGCT GGGCGACGGC     300

TACAACGGCA CCCTGCTGCT GGTGCTCAAC GCCGCCGGCA CCCGCACCTA CCTGAAGAGC     360

TACGAGGCGG ACGCCGAGGG CCAGCGCTTC GAGATCGCCC TGGACGGCAA CTACACCGGC     420

CAGCTCGGCG CCGACAACTT GGTCTTCGCC GCGGCCGCG                            459
```

(2) INFORMATION FOR SEQ ID NO:10:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Leu Glu Gly Thr Asp Gly Asn Asp Thr Leu Ser Gly Thr Asp Ala His
1               5                   10                  15

Glu Thr Leu Leu Gly Leu Ala Gly Asn Asp Arg Leu Asn Gly Gly Ala
            20                  25                  30

Gly Asp Asp Ile Leu Asp Gly Gly Ala Gly Arg Asp Thr Leu Thr Gly
        35                  40                  45

Gly Ala Gly Ala Asp Thr Phe Arg Phe Ser Ala Arg Thr Asp Ser Tyr
    50                  55                  60

Arg Thr Asp Ser Ala Gly Asp Ser Phe Asn Asp Leu Ile Thr Asp Phe
65                  70                  75                  80

Asp Ala Ser Glu Asp Arg Ile Asp Leu Ser Ala Leu Gly Phe Thr Gly
            85                  90                  95

Leu Gly Asp Gly Tyr Asn Gly Thr Leu Leu Leu Gln Leu Asn Ser Ala
            100                 105                 110

```
Gly Thr Arg Thr Tyr Leu Lys Ser Tyr Glu Ala Asp Ala Glu Gly Arg
            115                 120                 125

Arg Phe Glu Ile Ala Leu Asp Gly Asn Phe Thr Gly Leu Leu Gly Ala
        130                 135                 140

Glu Asn Phe Ile Phe Ala Thr Thr Pro
145                 150
```

(2) INFORMATION FOR SEQ ID NO:11:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

```
Leu Xaa Gly Gly Ala Gly Xaa Asp Xaa
1               5
```

(2) INFORMATION FOR SEQ ID NO:12:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:12:

```
Ala Arg Arg Arg Arg Ser
1               5
```

(2) INFORMATION FOR SEQ ID NO:13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Ala Arg Arg Arg Ala Arg Arg
1               5
```

(2) INFORMATION FOR SEQ ID NO:14:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Arg Ala Arg Ser
1
```

(2) INFORMATION FOR SEQ ID NO:15:

(i) SEQUENCE CHARACTERISTICS:
        (A) LENGTH: 4 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO:15:

Ala Arg Arg Arg
1

(2) INFORMATION FOR SEQ ID NO:16:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "Oligonucleotide"

(xi) SEQUENCE DESCRIPTION: SEQ ID NO:16:

ATGGAYTAYA AYGTNAARGA                                              20

(2) INFORMATION FOR SEQ ID NO:17:

(i) SEQUENCE CHARACTERISTICS:
         (A) LENGTH: 1176 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:17:

ATGGATTACA ACGTCAAGGA TTTCGGTGCA TTGGGCGACG GCGTCAGCGA CGACCGGGCC     60

TCCATCCAGG CGGCGATCGA TGCCGCCTAC GCCGCCGGTG GCGGTACCGT CTACCTGCCG    120

GCCGGCGAGT ACCGGGTCAG CGCCGCCGGG GAGCCGGGCG ACGGCTGCCT GATGCTCAAG    180

GACGGCGTCT ACCTGGCCGG TGCCGGCATG GGCGAGACGG TGATCAAGCT GATCGACGGC    240

TCCGACCAGA AGATCACCGG CATGGTCCGC TCGGCCTACG GCGAGGAAAC CAGCAACTTC    300

GGCATGCGCG ACCTGACCCT CGACGGCAAC CGCGACAACA CCAGCGGCAA GGTCGACGGC    360

TGGTTCAACG GCTATATCCC CGGCGGGGAC GGCGCCGACC GCGACGTGAC CATCGAGCGG    420

GTGGAGGTCC GCGAGATGTC CGGCTACGGC TTCGACCCCC ACGAGCAGAC CATCAACCTG    480

ACGATCCGCG ACAGCGTGGC CCACGACAAC GGCCTCGACG GCTTCGTCGC CGACTACCTG    540

GTCGACAGCG TGTTCGAGAA CAACGTCGCC TACGCCAACG ACCGCCACGG CTTCAACGTG    600

GTCACCAGCA CCCACGATTT CGTCATGACC AACAACGTCG CCTACGGCAA CGGCAGCAGC    660

GGCCTGGTGG TGCAGCGGGG TCTGGAGGAC CTCGCGCTGC CCAGCAACAT CCTGATCGAC    720

GGCGGCGCCT ACTACGACAA CGCCCGCGAA GGCGTGCTGC TCAAGATGAC CAGCGACATC    780

ACCCTGCAGA ACGCCGATAT CCACGGCAAC GGCTCCTCCG GGGTGCGCGT CTACGGCGCC    840

CAGGACGTGC AGATCCTCGA TAACCAGATC CACGACAACG CGCAGGCGGC CGCCGTGCCC    900

GAGGTCCTGC TGCAGTCCTT CGACGATACC GCCGGGGCGT CCGGCACCTA CTACACGACC    960

CTGAACACCC GGATCGAGGG CAACACCATC AGCGGCTCGG CCAACTCCAC CTACGGCATC   1020

CAGGAGCGCA ACGACGGCAC CGACTACAGC AGCCTGATCG ACAACGACAT CGCCGGGGTG   1080

CAACAGCCCA TCCAACTGTA CGGACCTCAC TCGACGGTAT CCGGCGAACC CGGCGCGACA   1140

CCGCAACAGC CGTCCACGGG AAGCGACGGC GAGCCA                             1176

(2) INFORMATION FOR SEQ ID NO:18:

(i) SEQUENCE CHARACTERISTICS:
    (A) LENGTH: 1155 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:18:

```
ATGGATTACA ACGTCAAGGA TTTCGGAGCA CTGGGCGATG GCGTCAGCGA CGACACGGCG      60

GCCATCCAGG CGGCGATCGA CGCCGCCCAC GCGGCGGGCG GCGGCACCGT CTACCTGCCG     120

GCCGGCGAAT ATCGGGTCAG CGGCGGCGAG GAGCCTTCCG ATGGTTGTCT GACCATCAAG     180

AGCAACGTCC ATATCGTCGG CGCCGGGATG GGCGAGACGG TGATCAAGAT GGTCGACGGC     240

TGGACGCAGA ACGTCACCGG CATGGTGCGC TCGGCCTACG GCGAGGAAAC CAGCAACTTC     300

GGCATGAGCG ACCTGACCCT CGACGGCAAC CGCGACAACC TGTCCGCCAA GGTCGACGGC     360

TGGTTCAACG GCTACATCCC CGGCCAGGAC GGCGCCGATC GCGACGTGAC CCTGGAGCGG     420

GTGGAAATCC GCGAGATGTC CGGCTACGGT TTCGACCCCC ACGAGCAGAC CATCAACCTG     480

ACGATCCGCG ACAGCGTGGC CCACGACAAC AGCCTCGACG GCTTCGTCGC CGACTACCAG     540

GTCGGCGGGG TGTTCGAGAA CAACGTCTCG TACAACAACG ACCGCCACGG CTTCAACATC     600

GTCACCAGCA CCAACGACTT CGTCCTGAGC AACAACGTCG CCTACGGCAA CGGCGGCGCC     660

GGCCTGGTGG TGCAGCGCGG CTCGTACGAC CTGCCCCATC CCTACGACAT CCTGATCGAC     720

GGCGGCGCCT ACTACGACAA CGCCTTGGAA GGCGTGCAGC TCAAGATGGC CCACGACGTC     780

ACCCTGCAGA ACGCCGAGAT CTACGGCAAC GGCCTGTACG GGGTGCGCGT CTACGGCGCC     840

CAGGACGTGC AGATCCTCGA CAACCAGATC CACGACAATT CGCAGAACGG CGCCTATGCC     900

GAAGTCCTGC TGCAGTCCTA CGACGACACC GCCGGGGTGT CCGGCAACTT TTACGTCACC     960

ACCGGCACCT GGCTCGAAGG CAACGTCATC AGCGGCTCGG CCAATTCCAC CTACGGCATC    1020

CAGGAGCGCG CCGACGGCAC CGACTACAGC AGCCTCTACG CCAACAGCAT CGACGGTGTG    1080

CAGACCGGGG CGGTACGGCT GTATGGCGCC AACTCGACGG TTTCCAGCCA GTCCGGCAGT    1140

GGCCAGCAGG CGACC                                                    1155
```

(2) INFORMATION FOR SEQ ID NO:19:

(i) SEQUENCE CHARACTERISTICS:
    (A) LENGTH: 1143 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:19:

```
GTGTTCAATG CCAAGGACTT CGGCGCGCTG GGCGACGGCG CCAGCGACGA CCGGCCGGCC      60

ATCCAGGCGG CGATCGACGC CGCCTACGCG GCCGGTGGCG GCACCGTCTA CCTGCCGGCC     120

GGCGAGTACC GGGTCAGCCC CACCGGGGAG CCGGGCGACG GCTGCCTGAT GCTCAAGGAC     180

GGCGTCTACC TGGCCGGCGA CGGCATAGGC GAAACGGTCA TCAAGCTGAT CGACGGCTCC     240

GACCAGAAGA TCACCGGCAT GGTGCGCTCG GCCTATGGCG AAGAGACCAG CAACTTCGGC     300

ATGAGCGACC TGACCCTCGA CGGCAACCGC GACAACACCA GCGGCAAGGT CGACGGCTGG     360

TTCAACGGCT ACATCCCCGG CCAGGACGGC GCCGACCGCA ACGTGACCAT CGAGCGGGTG     420

GAAATCCGCG AGATGTCCGG CTATGGCTTC GATCCGCACG AGCAGACCAT CAACCTGACG     480
```

```
ATCCGCGACA GCGTGGCCCA CGACAACGGC CTCGACGGCT TCGTCGCCGA CTACCTGGTC      540

GACAGCGTGT TCGAGAACAA CGTCGCCTAC AACAACGACC GCCACGGCTT CAACATCGTC      600

ACCAGCACCT ACGATTTCGT CATGACCAAC AACGTCGCCT ACGGCAACGG CGGCGCCGGC      660

CTGACGATCC AGCGGGGCTC GGAGGACCTG GCCCAGCCGA CCGATATCCT GATCGACGGC      720

GGCGCCTACT ACGACAACGC CCTGGAAGGC GTGCTGTTCA AGATGACCAA CAACGTCACC      780

CTGCAGAACG CCGAGATCTA CGGCAACGGC TCCTCCGGCG TGCGCCTGTA CGGCACGGAG      840

GACGTGCAGA TCCTCGACAA CCAGATCCAC GACAATTCGC AGAACGGCAC CTATCCGGAA      900

GTCCTGCTGC AGGCCTTCGA CGACAGCCAG GTCACCGGTG AGCTGTACGA GACCCTGAAC      960

ACCCGGATCG AAGGCAATCT CATCGACGCT TCGGACAACG CCAACTATGC GGTGCGCGAG     1020

CGCGACGACG GCAGCGACTA CACCACGCTC GTGGACAACG ACATCAGCGG CGGCCAGGTC     1080

GCCTCGGTGC AGCTTTCCGG CGCCCATTCG AGTCTTTCCG GCGGCACCGT CGAAGTGCCG     1140

CAG                                                                  1143

(2) INFORMATION FOR SEQ ID NO:20:

(i) SEQUENCE CHARACTERISTICS:
        (A) LENGTH: 1155 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

ATGGATTACA ACGTCAAAGA TTTCGGGGCG CTGGGCGATG GCGTCAGCGA CGATACGGCC       60

GCCATCCAGG CGGCGATCGA TGCCGCCTAC GCGGCCGGCG GCGGCACCGT CTACCTGCCG      120

GCCGGCGAAT ACCGGGTCAG CGGCGGCGAG GAGCCTTCCG ATGGTTGCCT GACCATCAAG      180

AGCAACGTCC ATATCGTCGG CGCGGGGATG GGCGAGACGG TCATCAAGCT GGTCGACGGC      240

TGGGATCAGG ACGTCACCGG CATCGTCCGC TCGGCCTACG GCGAGGAGAC CAGCAACTTC      300

GGCATGAGCG ACCTGACCCT CGACGGCAAC CGCGACAACA CCAGCGGCAA GGTCGACGGC      360

TGGTTCAACG GCTACATTCC CGGCGAGGAC GGCGCCGACC GCGACGTGAC CCTGGAGCGG      420

GTGGAAATCC GTGAAATGTC CGGTTACGGT TTCGATCCGC ACGAGCAGAC CATCAACCTG      480

ACGATCCGCG ACAGCGTGGC CCACGACAAC GGCCTCGACG GCTTCGTCGC CGATTTCCAG      540

ATCGGCGGGG TGTTCGAGAA CAACGTCTCG TACAACAACG ACCGCCACGG CTTCAACATC      600

GTCACCAGCA CCAACGACTT CGTCCTGAGC AACAACGTCG CCTACGGCAA CGGCGGCGCC      660

GGCCTGGTGG TGCAGCGCGG CTCGTCCGAC GTGGCGCACC CCTACGACAT CCTGATCGAC      720

GGCGGCGCCT ACTACGACAA CGGCCTGGAA GGCGTGCAGA TCAAGATGGC CCACGACGTC      780

ACCCTGCAGA ACGCCGAGAT CTACGGCAAC GGCCTATACG GGGTGCGCGT CTACGGCGCC      840

GAGGATGTGC AGATCCTCGA CAACTACATC CACGACAATT CGCAGAACGG TTCCTACGCG      900

GAAATCCTCC TGCAGTCCTA CGACGATACC GCCGGGGTGT CCGGCAATTT CTACACCACC      960

ACCGGCACCT GGATCGAAGG CAACACCATC GTCGGCTCGG CCAACTCCAC CTATGGCATC     1020

CAGGAGCGCG ACGACGGCAC CGACTACAGC AGCCTCTACG CCAACAGCGT CAGCAATGTG     1080

CAGAACGGCT CGGTGCGCCT CTACGGCGCC AACTCCGTCG TCTCCGACCT GCCCGGCACC     1140

GGCCAGCAGG CGACC                                                     1155

(2) INFORMATION FOR SEQ ID NO:21:
```

(i) SEQUENCE CHARACTERISTICS:
    (A) LENGTH: 1155 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:21:

```
ATGGACTTCA ACGTCAAAGA TTTCGGGGCA CTGGGCGATG GCGCCAGCGA CGACACGGCG    60

GCCATCCAGG CGGCGATCGA TGCCGCCCAC GCGGCGGGCG GCGGCACCGT CTACCTGCCG   120

GCTGGCGAGT ATCGGGTCAG CGGCGGCGAG GAGCCTTCCG ACGGCGCGCT GACCATCAAG   180

AGCAACGTCT ATATCGTCGG CGCCGGGATG GGCGAGACGG TGATCAAGAT GGTCGACGGC   240

TGGACGCAGA ACGTCACCGG CATGGTGCGC TCGGCCTATG GCGAGGAGAC CAGCAACTTC   300

GGCATGAGCG ACCTGACCCT CGACGGCAAC CGCGACAACC TGTCCGCCAA GGTCGACGGC   360

TGGTTCAACG GCTACATTCC CGGCCAGGAC GGTGCCGATC GCGACGTGAC CCTGGAGCGG   420

GTGGAAATCC GCGAAATGTC CGGTTACGGT TTCGATCCGC ACGAGCAGAC CATCAACCTG   480

ACGATCCGCG ACAGCGTGGC CCACGACAAC GGCCTCGACG GCTTCGTCGC CGACTACCAG   540

GTCGGCGGGG TGTTCGAGAA CAACGTCTCG TACAACAACG ACCGCCACGG CTTCAACATC   600

GTCACCAGCA CCAACGACTT CGTCCTGAGC AACAACGTCG CCTACGGCAA CGGCGGCGCC   660

GGCCTGGTGG TGCAGCGCGG CTCGTACGAC CTGCCCCATC CCTACGACAT CCTGATCGAC   720

GGCGGCGCCT ACTACGACAA CGCCTTGGAA GGCGTGCAGC TCAAGATGAC CCACGACGTC   780

ACCCTGCAGA ACGCCGAGAT CTATGGCAAC GGCCTGTACG GGGTGCGCGT CTACGGCGCC   840

CAGGACGTGC AACTCCTCGA TAACCAGATC CACGACAATT CGCAGAACGG CGCCTATGCC   900

GAAGTCCTGC TGCAGTCCTA CGACGACACC GCCGGGGTGT CCGGCAACTT TTACGTCACC   960

ACCGGCACCT GGCTCGAAGG CAACGTCATC AGCGGCTCGG CCAATTCCAC CTTCGGCATC  1020

CAGGAGCGCG CCGACGGCAC CGACTACAGC AGCCTTTACG CCAATACCAT CGACGGCGTG  1080

CAGAACGGGA CGGTACGGCT GTATGGCGCC AACTCCACGG TTTCCGAGCA GCCCAGCAGC  1140

GGCCAGCAGG CGACC                                                   1155
```

(2) INFORMATION FOR SEQ ID NO:22:

(i) SEQUENCE CHARACTERISTICS:
        (A) LENGTH: 87 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
GTGTTCAATG CCAAGGACTT CGGCGCGCTG GGCGACGGCG CCAGCGACGA CCGGCCGGCC    60

ATCCAGGCGG CGATCGACGC CGCCTAC                                       87
```

(2) INFORMATION FOR SEQ ID NO:23:

(i) SEQUENCE CHARACTERISTICS:
        (A) LENGTH: 392 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:23:

```
Met Asp Tyr Asn Val Lys Asp Phe Gly Ala Leu Gly Asp Gly Val Ser
1               5                   10                  15

Asp Asp Arg Ala Ser Ile Gln Ala Ala Ile Asp Ala Ala Tyr Ala Ala
                20                  25                  30

Gly Gly Gly Thr Val Tyr Leu Pro Ala Gly Glu Tyr Arg Val Ser Ala
            35                  40                  45

Ala Gly Glu Pro Gly Asp Gly Cys Leu Met Leu Lys Asp Gly Val Tyr
    50                  55                  60

Leu Ala Gly Ala Gly Met Gly Glu Thr Val Ile Lys Leu Ile Asp Gly
65                  70                  75                  80

Ser Asp Gln Lys Ile Thr Gly Met Val Arg Ser Ala Tyr Gly Glu Glu
                85                  90                  95

Thr Ser Asn Phe Gly Met Arg Asp Leu Thr Leu Asp Gly Asn Arg Asp
            100                 105                 110

Asn Thr Ser Gly Lys Val Asp Gly Trp Phe Asn Gly Tyr Ile Pro Gly
            115                 120                 125

Gly Asp Gly Ala Asp Arg Asp Val Thr Ile Glu Arg Val Glu Val Arg
    130                 135                 140

Glu Met Ser Gly Tyr Gly Phe Asp Pro His Glu Gln Thr Ile Asn Leu
145                 150                 155                 160

Thr Ile Arg Asp Ser Val Ala His Asp Asn Gly Leu Asp Gly Phe Val
                165                 170                 175

Ala Asp Tyr Leu Val Asp Ser Val Phe Glu Asn Asn Val Ala Tyr Ala
            180                 185                 190

Asn Asp Arg His Gly Phe Asn Val Val Thr Ser Thr His Asp Phe Val
            195                 200                 205

Met Thr Asn Asn Val Ala Tyr Gly Asn Gly Ser Ser Gly Leu Val Val
    210                 215                 220

Gln Arg Gly Leu Glu Asp Leu Ala Leu Pro Ser Asn Ile Leu Ile Asp
225                 230                 235                 240

Gly Gly Ala Tyr Tyr Asp Asn Ala Arg Glu Gly Val Leu Leu Lys Met
                245                 250                 255

Thr Ser Asp Ile Thr Leu Gln Asn Ala Asp Ile His Gly Asn Gly Ser
            260                 265                 270

Ser Gly Val Arg Val Tyr Gly Ala Gln Asp Val Gln Ile Leu Asp Asn
            275                 280                 285

Gln Ile His Asp Asn Ala Gln Ala Ala Val Pro Glu Val Leu Leu
    290                 295                 300

Gln Ser Phe Asp Asp Thr Ala Gly Ala Ser Gly Thr Tyr Tyr Thr Thr
305                 310                 315                 320

Leu Asn Thr Arg Ile Glu Gly Asn Thr Ile Ser Gly Ser Ala Asn Ser
                325                 330                 335

Thr Tyr Gly Ile Gln Glu Arg Asn Asp Gly Thr Asp Tyr Ser Ser Leu
            340                 345                 350

Ile Asp Asn Asp Ile Ala Gly Val Gln Gln Pro Ile Gln Leu Tyr Gly
            355                 360                 365

Pro His Ser Thr Val Ser Gly Glu Pro Gly Ala Thr Pro Gln Gln Pro
    370                 375                 380

Ser Thr Gly Ser Asp Gly Glu Pro
385                 390
```

(2) INFORMATION FOR SEQ ID NO:24:

(i) SEQUENCE CHARACTERISTICS:
        (A) LENGTH: 385 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:24:

```
Met Asp Tyr Asn Val Lys Asp Phe Gly Ala Leu Gly Asp Gly Val Ser
1               5                  10                  15

Asp Asp Thr Ala Ala Ile Gln Ala Ala Ile Asp Ala Ala His Ala Ala
            20                  25                  30

Gly Gly Gly Thr Val Tyr Leu Pro Ala Gly Glu Tyr Arg Val Ser Gly
        35                  40                  45

Gly Glu Glu Pro Ser Asp Gly Cys Leu Thr Ile Lys Ser Asn Val His
    50                  55                  60

Ile Val Gly Ala Gly Met Gly Glu Thr Val Ile Lys Met Val Asp Gly
65                  70                  75                  80

Trp Thr Gln Asn Val Thr Gly Met Val Arg Ser Ala Tyr Gly Glu Glu
                85                  90                  95

Thr Ser Asn Phe Gly Met Ser Asp Leu Thr Leu Asp Gly Asn Arg Asp
            100                 105                 110

Asn Leu Ser Ala Lys Val Asp Gly Trp Phe Asn Gly Tyr Ile Pro Gly
        115                 120                 125

Gln Asp Gly Ala Asp Arg Asp Val Thr Leu Glu Arg Val Glu Ile Arg
    130                 135                 140

Glu Met Ser Gly Tyr Gly Phe Asp Pro His Glu Gln Thr Ile Asn Leu
145                 150                 155                 160

Thr Ile Arg Asp Ser Val Ala His Asp Asn Ser Leu Asp Gly Phe Val
                165                 170                 175

Ala Asp Tyr Gln Val Gly Gly Val Phe Glu Asn Asn Val Ser Tyr Asn
            180                 185                 190

Asn Asp Arg His Gly Phe Asn Ile Val Thr Ser Thr Asn Asp Phe Val
        195                 200                 205

Leu Ser Asn Asn Val Ala Tyr Gly Asn Gly Gly Ala Gly Leu Val Val
    210                 215                 220

Gln Arg Gly Ser Tyr Asp Leu Pro His Pro Tyr Asp Ile Leu Ile Asp
225                 230                 235                 240

Gly Gly Ala Tyr Tyr Asp Asn Ala Leu Glu Gly Val Gln Leu Lys Met
                245                 250                 255

Ala His Asp Val Thr Leu Gln Asn Ala Glu Ile Tyr Gly Asn Gly Leu
            260                 265                 270

Tyr Gly Val Arg Val Tyr Gly Ala Gln Asp Val Gln Ile Leu Asp Asn
        275                 280                 285

Gln Ile His Asp Asn Ser Gln Asn Gly Ala Tyr Ala Glu Val Leu Leu
    290                 295                 300

Gln Ser Tyr Asp Asp Thr Ala Gly Val Ser Gly Asn Phe Tyr Val Thr
305                 310                 315                 320

Thr Gly Thr Trp Leu Glu Gly Asn Val Ile Ser Gly Ser Ala Asn Ser
                325                 330                 335

Thr Tyr Gly Ile Gln Glu Arg Ala Asp Gly Thr Asp Tyr Ser Ser Leu
            340                 345                 350

Tyr Ala Asn Ser Ile Asp Gly Val Gln Thr Gly Ala Val Arg Leu Tyr
        355                 360                 365
```

Gly Ala Asn Ser Thr Val Ser Ser Gln Ser Gly Ser Gly Gln Gln Ala
    370                 375                 380

Thr
385

(2) INFORMATION FOR SEQ ID NO:25:

(i) SEQUENCE CHARACTERISTICS:
       (A) LENGTH: 381 amino acids
       (B) TYPE: amino acid
       (C) STRANDEDNESS: single
       (D) TOPOLOGY: linear (ii) MOLECULE TYPE: protein (xi) SEQUENCE DESCRIPTION: SEQ ID NO:25:

Val Phe Asn Ala Lys Asp Phe Gly Ala Leu Gly Asp Gly Ala Ser Asp
1               5                   10                  15

Asp Arg Pro Ala Ile Gln Ala Ala Ile Asp Ala Ala Tyr Ala Ala Gly
                20                  25                  30

Gly Gly Thr Val Tyr Leu Pro Ala Gly Glu Tyr Arg Val Ser Pro Thr
            35                  40                  45

Gly Glu Pro Gly Asp Gly Cys Leu Met Leu Lys Asp Gly Val Tyr Leu
50                  55                  60

Ala Gly Asp Gly Ile Gly Glu Thr Val Ile Lys Leu Ile Asp Gly Ser
65                  70                  75                  80

Asp Gln Lys Ile Thr Gly Met Val Arg Ser Ala Tyr Gly Glu Glu Thr
                85                  90                  95

Ser Asn Phe Gly Met Ser Asp Leu Thr Leu Asp Gly Asn Arg Asp Asn
            100                 105                 110

Thr Ser Gly Lys Val Asp Gly Trp Phe Asn Gly Tyr Ile Pro Gly Gln
        115                 120                 125

Asp Gly Ala Asp Arg Asn Val Thr Ile Glu Arg Val Glu Ile Arg Glu
130                 135                 140

Met Ser Gly Tyr Gly Phe Asp Pro His Glu Gln Thr Ile Asn Leu Thr
145                 150                 155                 160

Ile Arg Asp Ser Val Ala His Asp Asn Gly Leu Asp Gly Phe Val Ala
                165                 170                 175

Asp Tyr Leu Val Asp Ser Val Phe Glu Asn Asn Val Ala Tyr Asn Asn
            180                 185                 190

Asp Arg His Gly Phe Asn Ile Val Thr Ser Thr Tyr Asp Phe Val Met
        195                 200                 205

Thr Asn Asn Val Ala Tyr Gly Asn Gly Gly Ala Gly Leu Thr Ile Gln
210                 215                 220

Arg Gly Ser Glu Asp Leu Ala Gln Pro Thr Asp Ile Leu Ile Asp Gly
225                 230                 235                 240

Gly Ala Tyr Tyr Asp Asn Ala Leu Glu Gly Val Leu Phe Lys Met Thr
                245                 250                 255

Asn Asn Val Thr Leu Gln Asn Ala Glu Ile Tyr Gly Asn Gly Ser Ser
            260                 265                 270

Gly Val Arg Leu Tyr Gly Thr Glu Asp Val Gln Ile Leu Asp Asn Gln
        275                 280                 285

Ile His Asp Asn Ser Gln Asn Gly Thr Tyr Pro Glu Val Leu Leu Gln
290                 295                 300

Ala Phe Asp Asp Ser Gln Val Thr Gly Glu Leu Tyr Glu Thr Leu Asn
305                 310                 315                 320

```
Thr Arg Ile Glu Gly Asn Leu Ile Asp Ala Ser Asp Asn Ala Asn Tyr
            325                 330                 335

Ala Val Arg Glu Arg Asp Asp Gly Ser Asp Tyr Thr Thr Leu Val Asp
            340                 345                 350

Asn Asp Ile Ser Gly Gly Gln Val Ala Ser Val Gln Leu Ser Gly Ala
            355                 360                 365

His Ser Ser Leu Ser Gly Gly Thr Val Glu Val Pro Gln
370                 375                 380
```

(2) INFORMATION FOR SEQ ID NO:26:

(i) SEQUENCE CHARACTERISTICS:
        (A) LENGTH: 385 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:26:

```
Met Asp Tyr Asn Val Lys Asp Phe Gly Ala Leu Gly Asp Gly Val Ser
1               5                   10                  15

Asp Asp Thr Ala Ala Ile Gln Ala Ala Ile Asp Ala Ala Tyr Ala Ala
            20                  25                  30

Gly Gly Gly Thr Val Tyr Leu Pro Ala Gly Glu Tyr Arg Val Ser Gly
            35                  40                  45

Gly Glu Glu Pro Ser Asp Gly Cys Leu Thr Ile Lys Ser Asn Val His
            50                  55                  60

Ile Val Gly Ala Gly Met Gly Glu Thr Val Ile Lys Leu Val Asp Gly
65                  70                  75                  80

Trp Asp Gln Asp Val Thr Gly Ile Val Arg Ser Ala Tyr Gly Glu Glu
            85                  90                  95

Thr Ser Asn Phe Gly Met Ser Asp Leu Thr Leu Asp Gly Asn Arg Asp
            100                 105                 110

Asn Thr Ser Gly Lys Val Asp Gly Trp Phe Asn Gly Tyr Ile Pro Gly
            115                 120                 125

Glu Asp Gly Ala Asp Arg Asp Val Thr Leu Glu Arg Val Glu Ile Arg
            130                 135                 140

Glu Met Ser Gly Tyr Gly Phe Asp Pro His Glu Gln Thr Ile Asn Leu
145                 150                 155                 160

Thr Ile Arg Asp Ser Val Ala His Asp Asn Gly Leu Asp Gly Phe Val
            165                 170                 175

Ala Asp Phe Gln Ile Gly Gly Val Phe Glu Asn Asn Val Ser Tyr Asn
            180                 185                 190

Asn Asp Arg His Gly Phe Asn Ile Val Thr Ser Thr Asn Asp Phe Val
            195                 200                 205

Leu Ser Asn Asn Val Ala Tyr Gly Asn Gly Gly Ala Gly Leu Val Val
            210                 215                 220

Gln Arg Gly Ser Ser Asp Val Ala His Pro Tyr Asp Ile Leu Ile Asp
225                 230                 235                 240

Gly Gly Ala Tyr Tyr Asp Asn Gly Leu Glu Gly Val Gln Ile Lys Met
            245                 250                 255

Ala His Asp Val Thr Leu Gln Asn Ala Glu Ile Tyr Gly Asn Gly Leu
            260                 265                 270

Tyr Gly Val Arg Val Tyr Gly Ala Glu Asp Val Gln Ile Leu Asp Asn
            275                 280                 285
```

-continued

Tyr Ile His Asp Asn Ser Gln Asn Gly Ser Tyr Ala Glu Ile Leu Leu
290                 295                 300

Gln Ser Tyr Asp Asp Thr Ala Gly Val Ser Gly Asn Phe Tyr Thr Thr
305                 310                 315                 320

Thr Gly Thr Trp Ile Glu Gly Asn Thr Ile Val Gly Ser Ala Asn Ser
                325                 330                 335

Thr Tyr Gly Ile Gln Glu Arg Asp Asp Gly Thr Asp Tyr Ser Ser Leu
            340                 345                 350

Tyr Ala Asn Ser Val Ser Asn Val Gln Asn Gly Ser Val Arg Leu Tyr
            355                 360                 365

Gly Ala Asn Ser Val Val Ser Asp Leu Pro Gly Thr Gly Gln Gln Ala
            370                 375                 380

Thr

385

(2) INFORMATION FOR SEQ ID NO:27:

(i) SEQUENCE CHARACTERISTICS:
        (A) LENGTH: 385 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:27:

Met Asp Phe Asn Val Lys Asp Phe Gly Ala Leu Gly Asp Gly Ala Ser
1               5                   10                  15

Asp Asp Thr Ala Ala Ile Gln Ala Ala Ile Asp Ala Ala His Ala Ala
            20                  25                  30

Gly Gly Gly Thr Val Tyr Leu Pro Ala Gly Glu Tyr Arg Val Ser Gly
            35                  40                  45

Gly Glu Glu Pro Ser Asp Gly Ala Leu Thr Ile Lys Ser Asn Val Tyr
        50                  55                  60

Ile Val Gly Ala Gly Met Gly Glu Thr Val Ile Lys Met Val Asp Gly
65                  70                  75                  80

Trp Thr Gln Asn Val Thr Gly Met Val Arg Ser Ala Tyr Gly Glu Glu
                85                  90                  95

Thr Ser Asn Phe Gly Met Ser Asp Leu Thr Leu Asp Gly Asn Arg Asp
            100                 105                 110

Asn Leu Ser Ala Lys Val Asp Gly Trp Phe Asn Gly Tyr Ile Pro Gly
            115                 120                 125

Gln Asp Gly Ala Asp Arg Asp Val Thr Leu Glu Arg Val Glu Ile Arg
130                 135                 140

Glu Met Ser Gly Tyr Gly Phe Asp Pro His Glu Gln Thr Ile Asn Leu
145                 150                 155                 160

Thr Ile Arg Asp Ser Val Ala His Asp Asn Gly Leu Asp Gly Phe Val
            165                 170                 175

Ala Asp Tyr Gln Val Gly Val Phe Glu Asn Asn Val Ser Tyr Asn
            180                 185                 190

Asn Asp Arg His Gly Phe Asn Ile Val Thr Ser Thr Asn Asp Phe Val
            195                 200                 205

Leu Ser Asn Asn Val Ala Tyr Gly Asn Gly Gly Ala Gly Leu Val Val
            210                 215                 220

Gln Arg Gly Ser Tyr Asp Leu Pro His Pro Tyr Asp Ile Leu Ile Asp
225                 230                 235                 240

```
Gly Gly Ala Tyr Tyr Asp Asn Ala Leu Glu Gly Val Gln Leu Lys Met
            245                 250                 255

Thr His Asp Val Thr Leu Gln Asn Ala Glu Ile Tyr Gly Asn Gly Leu
            260                 265                 270

Tyr Gly Val Arg Val Tyr Gly Ala Gln Asp Val Gln Leu Leu Asp Asn
            275                 280                 285

Gln Ile His Asp Asn Ser Gln Asn Gly Ala Tyr Ala Glu Val Leu Leu
            290                 295                 300

Gln Ser Tyr Asp Asp Thr Ala Gly Val Ser Gly Asn Phe Tyr Val Thr
305                 310                 315                 320

Thr Gly Thr Trp Leu Glu Gly Asn Val Ile Ser Gly Ser Ala Asn Ser
            325                 330                 335

Thr Phe Gly Ile Gln Glu Arg Ala Asp Gly Thr Asp Tyr Ser Ser Leu
            340                 345                 350

Tyr Ala Asn Thr Ile Asp Gly Val Gln Asn Gly Thr Val Arg Leu Tyr
            355                 360                 365

Gly Ala Asn Ser Thr Val Ser Glu Gln Pro Ser Ser Gly Gln Gln Ala
            370                 375                 380

Thr
385

(2) INFORMATION FOR SEQ ID NO:28:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:28:

Val Phe Asn Ala Lys Asp Phe Gly Ala Leu Gly Asp Gly Ala Ser Asp
1               5                   10                  15

Asp Arg Pro Ala Ile Gln Ala Ala Ile Asp Ala Ala Tyr
            20                  25

(2) INFORMATION FOR SEQ ID NO:29:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:29:

CTGGTCGGCG GCGACACGGA CGACCAGCTC CAGGGCGGCT CCGGCGCCGA TCGCCTGGAC      60

GGCGGGGCCG GCGACGACAT CCTCGACGGC GGCGCCGGGC GCGACCGGCT GAGCGGCGGC     120

GCGGGCGCCG ACACCTTCGT GTTCTCCGCC CGCGAGGACA GCTACCGTAC CGACACGGCG     180

GTGTTCAACG ACCTGATCCT CGACTTCGAG GCCAGCGAGG ATCGCATCGA CCTGTCCGCG     240

CTGGGCTTTT CCGGCCTGGG CGACGGCTAT GGCGGCACCC TGCTCCTGAA GACCAACGCC     300

GAGGGCACGC GCACCTACCT GAAAAGCTTC GAGGCGGATG CCGAGGGACG GCGCTTCGAG     360

GTCGCCCTGG ACGGCGACCA CACGGGCGAT CTTTCCGCCG CCAATGTGGT CTTCGCCGCG     420

ACCGGG                                                                426
```

(2) INFORMATION FOR SEQ ID NO:30:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

```
CTCGAAGGCA GCGCGGGCAA CGATGCGCTG AGCGGGACCG AGGCCCACGA GACGCTGCTC      60

GGCCAGGCCG GCGACGACCG CCTGAACGGC GATGCCGGCA ACGACATCCT CGACGGCGGG     120

GCAGGGCGCG ACAACCTGAC CGGCGGCGCG GGCGCCGACA CCTTCCGCTT CTCCGCGCGC     180

ACCGACAGCT ACCGCACCGA CAGCGCCAGC TTCAACGACC TGATCACCGA CTTCGACGCC     240

GACGAGGACA GCATCGACCT GTCCGCGCTG GGCTTCACCG GCCTGGGCGA CGGCTACAAT     300

GGCACCCTGC TGCTGAAGAC CAACGCCGAG GGTACGCGCA CCTACCTGAA GAGCTACGAA     360

GCGGACGCCC AGGGCCGGCG CTTCGAGATC GCCCTGGACG GCAACTTCAC CGGTCTGTTC     420

AACGACAACA ACCTGTTGTT CGACGCCGCT CCG                                  453
```

(2) INFORMATION FOR SEQ ID NO:31:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

```
GCCACCGGTA CCGAGGGCAG CGACAACCTG CTCGGCACCG ACGCCGGGGA AACCCTCCTG      60

GGCTACGGCG GCAACGACAC CCTCAACGGC GGGGCCGGCG ACGACATCCT GGTCGGCGGC     120

GCCGGGCGCG ACAGCCTGAC CGGCGGCGCC GGGGCGGACG TGTTCCGCTT CGACGCGCTG     180

TCCGACAGCC AGCGCAACTA CACCACCGGC GACAACCAGG CCGACCGCAT TCTCGACTTC     240

GACCCGACCC TGGACAGGAT CGACGTGTCG GCGCTGGGCT TCACCGGGCT GGGCAACGGC     300

CGCAACGGCA CCCTCGCCGT GGTGCTCAAC AGCGCCGGCG ACCGCACCGA TCTGAAGAGC     360

TACGACACCG ACGCCAACGG CTACAGCTTC GAGCTTTCCC TCGCGGGCAA CTACCAGGGG     420

CAGCTCAGCG CCGAGCAGTT CGTTTTCGCG ACGTCTCAG                            459
```

(2) INFORMATION FOR SEQ ID NO:32:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

```
ATCGAAGGCA CCGACGGCAA CGATACCTTG CAGGGCACCG AGGCCAACGA GCGGCTCCTC      60

GGCCTGGACG GCCGGGACAA CCTGAACGGC GGCGCCGGCG ACGACATCCT CGACGGCGGA     120

GCGGGGCGCG ACACCCTGAC CGGCGGCACG GGGGCCGACA CCTTCCTGTT CTCCACGCGT     180

ACCGACAGCT ACCGCACCGA CAGCGCCAGC TTCAACGACC TGATCACCGA CTTCGATCCC     240

ACCCAGGACC GCATCGACCT GTCCGGCCTG GGCTTCAGCG GTTTCGGCAA CGGCTACGAC     300
```

```
GGCACCCTGC TGCTGCAGGT CAACGCCGCG GGCACCCGCA CCTACCTGAA GAGTTTCGAG        360

GCCGATGCCA ACGGCCAGCG CTTCGAGATC GCCCTGGACG GCGACTTCAG CGGCCAATTG        420

GACAGCGGCA ACGTGATCTT CGAGCCCGCC                                         450

(2) INFORMATION FOR SEQ ID NO:33:

(i) SEQUENCE CHARACTERISTICS:
        (A) LENGTH: 447 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

GGGACCGACG GCAACGACGT GCTGGTCGGC AGCGATGCCA ACGACCAGCT CTACGGCGGA         60

GCCGGCGACG ACCGCCTGGA CGGCGGCGCC GGTGACGACC TGCTCGACGG CGGAGCGGGG        120

CGCGACGACC TGACCGGCGG CACGGGTGCC GACACCTTCG TGTTCGCCGC GCGTACCGAT        180

AGCTACCGCA CCGACGCGGG GGTGTTCAAC GACCTGATCC TCGACTTCGA CGCCAGCGAG        240

GACCGCATCG ACCTGTCCGC CCTGGGTTTC AGCGGCTTCG GCGACGGCTA CAACGGCACC        300

CTGCTGGTGC AGCTCAGCAG CGCCGGAACC CGTACCTACC TCAAGAGCTA CGAGGAGGAC        360

CTCGAGGGCC GGCGCTTCGA GGTCGCCCTG GACGGCGACC ACACGGGCGA TCTTTCCGCC        420

GCCAATGTGG TTTTCGCCGA CGACGGC                                           447

(2) INFORMATION FOR SEQ ID NO:34:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

CTCGAAGGCA CGGCCGGCAA CGACACGCTT GGCGGCAGCG ACGCCCACGA GACGCTGCTC         60

GGGCTGGACG GCAACGACCG CCTGAACGGC GGCGCCGGCA ACGACATCCT CGACGGCGGC        120

GCCGGGCGCG ACAACCTGAC CGGCGGCGCG GGCGCCGACC TGTTCCGCGT CTCCGCGCGC        180

ACCGACAGCT ACCGCACCGA CAGCGCCAGC TTCAACGACC TGATCACCGA CTTCGACGCC        240

AGCCAGGACC GCATCGACCT GTCCGCGCTG GCTTCACCG GCTGGGCGA CGGCTATAAC         300

GGCACCCTGC TGCTGCAGGT CAGCGCCGAC GGCAGCCGCA CCTATCTGAA GAGCCTGGAG        360

GCGGATGCCG AGGGGCGGCG TTTCGAGATC GCCCTGGACG GCAACTTCGC CGGCCTGCTC        420

GGTGCCGGCA ACCTGCTCTT CGAGCGCACC GCC                                    453

(2) INFORMATION FOR SEQ ID NO:35:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

ATCGAGGGGG ATGCCGGCGA CAACGCCCTG CTCGGTACCT CGGCCGCCGA GACATTGCTC         60

GGCCACGCCG GCAACGACAC GCTCGACGGC GGGGCCGGCG ACGACATCCT GGTCGGCGGC        120
```

```
GCCGGGCGCG ACAGCCTCAC CGGCGGCGCC GGAGCGGACG TGTTCCGCTT CGACGCGCTG      180

TCCGACAGCC AGCGCAACTA CGACATCGGC GACAACCAGG GCGACCGCAT CGCCGACTTC      240

GCGGTGGGCG AAGACAAGCT CGACGTATCG GCGCTGGGCT TCACCGGGCT GGGCGACGGC      300

TACAACGGCA CCCTCGCCCT GGTGCTCAAC AGCGCCGGCG ACCGCACCTA CGTGAAAAGC      360

TACGAGAACG GCGCCGACGG CTACCGCTTC GAGTTTTCCC TCGACGGCAA CTATCTGGAG      420

CTACTCGGCA ACGAGGATTT CATCTTCGCC ACGCCCAGC                             459
```

(2) INFORMATION FOR SEQ ID NO:36:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

```
CTCGAAGGCA GCGCCGGCAA CGACAGCCTG CAGGGCACGG CCGCCGACGA GGTGATCCAC       60

GGCGGCGGCG GCGCGACAC GCTGGCCGGA GGGGCCGGGG CCGACGTGTT CCGCTTTAGC       120

GAACTGACCG ACAGCTACCG AGACAGTGCC AGCTATGCCG ATCTGATCAC TGACTTCGAT      180

GCCAGCGAGG ATCGTATCGA CCTGTCCGGC CTCGGCTTCA GCGGTCTGGG CAACGGCTAC      240

GGCGGTACCC TGGCGCTGCA GGTGAACAGC GCCGGTACCC GCACCTACCT GAAGAGCTTC      300

GAGACCAACG CCGCCGGCGA GCGTTTCGAG ATCGCCCTGG ACGGCGACCT GTCCGCGCTC      360

GGCGGGGCCA ACCTGATCCT CGACGCGCGT ACCGTA                                396
```

(2) INFORMATION FOR SEQ ID NO:37:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

```
CTGGCGGGCG GCGACGGCAA CGACACGCTT TCCGGCAGCA GCGCGGCCGA GGAACTGCTC       60

GGCGGGGTCG GCAACGACAG CCTGGACGGC GGCGCCGGCA ACGACATCCT CGACGGCGGG      120

GCGGGGCGCG ACACCCTGAG TGGCGGCAGC GGCAGCGACA TCTTCCGCTT CGGCGGCGCG      180

CTCGACAGCT TCCGCAACTA CGCCAGCGGG ACGAACGGCA CCGACAGCAT CACCGACTTC      240

ACCCCCGGCG AGGATCTGAT CGACCTCTCC GTGCTCGGCT ACACCGGGCT GGGCGACGGC      300

TACAACGGTA CCCTGGCGAT AGTGCTGAAC GACGCCGGCA CCAAGACCTA CCTGAAAAAC      360

CGCGAGAGCG ACGCCGAAGG CAACCAGTTC GAGATCGCCC TGGAGGGCAA CCACGCCGAC      420

CAGCTCGATG CGAGCGACTT CATCTTCGCC ACGGCGGCC                             459
```

(2) INFORMATION FOR SEQ ID NO:38:

(i) SEQUENCE CHARACTERISTICS:
        (A) LENGTH: 453 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:38:

| | | | | | |
|---|---|---|---|---|---|
| CTCGAAGGCA | CCGCGGGCAA | CGACGTGCTC | AGCGGAACGG | GTGCCCACGA | GCTGATTCTC | 60 |
| GGCCTGGCCG | GCAACGATCG | CCTGGACGGT | GGCGCCGGCG | ACGACACCCT | CGACGGCGGC | 120 |
| GCGGGGCGCG | ATACCCTGAC | CGGCGGCGCG | GGCGCCGATA | CCTTCCGCTT | CTCTGCCCGC | 180 |
| GAGGACAGTC | ACCGCACCGA | CAGCGCCAGC | TTCACCGACC | TGATCACCGA | CTTCGACGCC | 240 |
| AGCCAGGACC | GCATCGACCT | CTCCGCGCTG | GCTTCACCG | GTCTGGGCAA | CGGTTATGAC | 300 |
| GGCACCCTGG | CGGTGACCAC | CGGTTCCGGC | GGCACCCGCA | CCTACCTGAA | GAGCTACGAG | 360 |
| GTGGACGCCC | AGGGCCGGCG | TTTCGAAATC | GCCCTGGACG | GCAACTTCGT | CGGCCAGTTC | 420 |
| AACGATGGCA | ACCTGTTGTT | CGACGCCGCT | CCG | | | 453 |

(2) INFORMATION FOR SEQ ID NO:39:

(i) SEQUENCE CHARACTERISTICS:
        (A) LENGTH: 459 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:39:

| | | | | | |
|---|---|---|---|---|---|
| GTCACCGGTA | CCGAGGGCAA | CGACAACCTG | TCCGGCACCG | ATGCCGGGGA | AACCCTCCTG | 60 |
| GGCTACGGCG | GCAACGACAC | CCTCAACGGC | GGGGCCGGCA | ACGACATCCT | GGTCGGCGGC | 120 |
| GCCGGGCGCG | ACACCCTGAC | CGGCGGCGCC | GGGGCGGACG | TGTTCCGCTT | CGAGGCGCTG | 180 |
| TCCGACAGCC | AGCGCAACTA | CACCGCCGGC | GACAACCAGG | GCGATTACAT | CATCGACTTC | 240 |
| GCCGTGGGCG | AAGACAGGAT | CGACGTATCG | GCGCTGGGTT | ACACCGGGCT | GGGCAACGGC | 300 |
| CGCAACGGCA | CCCTCGCCGT | GGTGCTCAAC | AGCGCCGGCG | ACCGCACCTA | CGTGAAGAGC | 360 |
| TACGACACTG | ACGCCAACGG | CTATAACTTC | GAGCTTTCCC | TCGCGGGCAA | CTACCAGGGG | 420 |
| CTGCTCGGCG | CCGAACAGTT | CGTCTTCGCC | ACGCCCCCG | | | 459 |

(2) INFORMATION FOR SEQ ID NO:40:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:40:

| | | | | | |
|---|---|---|---|---|---|
| ATCGAGGGAA | CCGACGGCAA | CGACAGCTTG | CAAGGGACCG | GGGCCGACGA | ACTGCTCCTC | 60 |
| GGTCTGGGCG | GCCGGGACAG | CCTGAACGGC | GGCGCCGGCG | ACGATGTCCT | GGATGGCGGG | 120 |
| GCGGAGCGCG | ACACCCTGAC | CGGCGGCACG | GGGGCCGACA | CCTTCCTGTT | CTCCGCGCGT | 180 |
| ACCGACAGCT | ACCGCACCGA | CAGCGCCAGC | TTCACCGACC | TGATCACCGA | CTTCGATCCC | 240 |
| GCCCAGGATC | GCATCGACCT | GTCCGGCCTG | GCTTCAGCG | GTTTCGGCAA | CGGCTACGAC | 300 |
| GGCACCCTGC | TGCTGCAGGT | CAACGCCGCG | GGCACCCGCA | CCTACCTGAA | GAGCCTCGAG | 360 |
| GCCGATGCCG | ACGGCCAGCG | CTTCGAGATC | GCCCTGGACG | GCGACTTCAG | CGGCCAGTTG | 420 |
| GACAGCGGCA | ACGTGATCTT | CGAGGCCGGC | | | | 450 |

(2) INFORMATION FOR SEQ ID NO:41:

(i) SEQUENCE CHARACTERISTICS:

(A) LENGTH: 142 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

Leu Val Gly Gly Asp Thr Asp Asp Gln Leu Gln Gly Ser Gly Ala
1               5                   10                  15

Asp Arg Leu Asp Gly Gly Ala Gly Asp Asp Ile Leu Asp Gly Gly Ala
            20                  25                  30

Gly Arg Asp Arg Leu Ser Gly Gly Ala Gly Ala Asp Thr Phe Val Phe
            35                  40                  45

Ser Ala Arg Glu Asp Ser Tyr Arg Thr Asp Thr Ala Val Phe Asn Asp
50                  55                  60

Leu Ile Leu Asp Phe Glu Ala Ser Glu Asp Arg Ile Asp Leu Ser Ala
65                  70                  75                  80

Leu Gly Phe Ser Gly Leu Gly Asp Gly Tyr Gly Gly Thr Leu Leu Leu
                85                  90                  95

Lys Thr Asn Ala Glu Gly Thr Arg Thr Tyr Leu Lys Ser Phe Glu Ala
                100                 105                 110

Asp Ala Glu Gly Arg Arg Phe Glu Val Ala Leu Asp Gly Asp His Thr
            115                 120                 125

Gly Asp Leu Ser Ala Ala Asn Val Val Phe Ala Ala Thr Gly
    130                 135                 140

(2) INFORMATION FOR SEQ ID NO:42:

(i) SEQUENCE CHARACTERISTICS:
        (A) LENGTH: 151 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:42:

Leu Glu Gly Ser Ala Gly Asn Asp Ala Leu Ser Gly Thr Glu Ala His
1               5                   10                  15

Glu Thr Leu Leu Gly Gln Ala Gly Asp Asp Arg Leu Asn Gly Asp Ala
            20                  25                  30

Gly Asn Asp Ile Leu Asp Gly Gly Ala Gly Arg Asp Asn Leu Thr Gly
            35                  40                  45

Gly Ala Gly Ala Asp Thr Phe Arg Phe Ser Ala Arg Thr Asp Ser Tyr
50                  55                  60

Arg Thr Asp Ser Ala Ser Phe Asn Asp Leu Ile Thr Asp Phe Asp Ala
65                  70                  75                  80

Asp Glu Asp Ser Ile Asp Leu Ser Ala Leu Gly Phe Thr Gly Leu Gly
                85                  90                  95

Asp Gly Tyr Asn Gly Thr Leu Leu Leu Lys Thr Asn Ala Glu Gly Thr
                100                 105                 110

Arg Thr Tyr Leu Lys Ser Tyr Glu Ala Asp Ala Gln Gly Arg Arg Phe
            115                 120                 125

Glu Ile Ala Leu Asp Gly Asn Phe Thr Gly Leu Phe Asn Asp Asn Asn
    130                 135                 140

Leu Leu Phe Asp Ala Ala Pro
145                 150

(2) INFORMATION FOR SEQ ID NO:43:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:43:

```
Ala Thr Gly Thr Glu Gly Ser Asp Asn Leu Leu Gly Thr Asp Ala Gly
  1               5                  10                  15

Glu Thr Leu Leu Gly Tyr Gly Gly Asn Asp Thr Leu Asn Gly Gly Ala
             20                  25                  30

Gly Asp Asp Ile Leu Val Gly Gly Ala Gly Arg Asp Ser Leu Thr Gly
         35                  40                  45

Gly Ala Gly Ala Asp Val Phe Arg Phe Asp Ala Leu Ser Asp Ser Gln
     50                  55                  60

Arg Asn Tyr Thr Thr Gly Asp Asn Gln Ala Asp Arg Ile Leu Asp Phe
 65                  70                  75                  80

Asp Pro Thr Leu Asp Arg Ile Asp Val Ser Ala Leu Gly Phe Thr Gly
                 85                  90                  95

Leu Gly Asn Gly Arg Asn Gly Thr Leu Ala Val Val Leu Asn Ser Ala
                100                 105                 110

Gly Asp Arg Thr Asp Leu Lys Ser Tyr Asp Thr Asp Ala Asn Gly Tyr
            115                 120                 125

Ser Phe Glu Leu Ser Leu Ala Gly Asn Tyr Gln Gly Gln Leu Ser Ala
        130                 135                 140

Glu Gln Phe Val Phe Ala Thr Ser Gln
145                 150
```

(2) INFORMATION FOR SEQ ID NO:44:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:44:

```
Ile Glu Gly Thr Asp Gly Asn Asp Thr Leu Gln Gly Thr Glu Ala Asn
  1               5                  10                  15

Glu Arg Leu Leu Gly Leu Asp Gly Arg Asp Asn Leu Asn Gly Gly Ala
             20                  25                  30

Gly Asp Asp Ile Leu Asp Gly Gly Ala Gly Arg Asp Thr Leu Thr Gly
         35                  40                  45

Gly Thr Gly Ala Asp Thr Phe Leu Phe Ser Thr Arg Thr Asp Ser Tyr
     50                  55                  60

Arg Thr Asp Ser Ala Ser Phe Asn Asp Leu Ile Thr Asp Phe Asp Pro
 65                  70                  75                  80

Thr Gln Asp Arg Ile Asp Leu Ser Gly Leu Gly Phe Ser Gly Phe Gly
                 85                  90                  95

Asn Gly Tyr Asp Gly Thr Leu Leu Leu Gln Val Asn Ala Ala Gly Thr
                100                 105                 110

Arg Thr Tyr Leu Lys Ser Phe Glu Ala Asp Ala Asn Gly Gln Arg Phe
            115                 120                 125
```

Glu Ile Ala Leu Asp Gly Asp Phe Ser Gly Gln Leu Asp Ser Gly Asn
130                 135                 140

Val Ile Phe Glu Pro Ala
145                 150

(2) INFORMATION FOR SEQ ID NO:45:

(i) SEQUENCE CHARACTERISTICS:
        (A) LENGTH: 149 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:45:

Gly Thr Asp Gly Asn Asp Val Leu Val Gly Ser Asp Ala Asn Asp Gln
1               5                   10                  15

Leu Tyr Gly Gly Ala Gly Asp Asp Arg Leu Asp Gly Gly Ala Gly Asp
            20                  25                  30

Asp Leu Leu Asp Gly Gly Ala Gly Arg Asp Asp Leu Thr Gly Gly Thr
            35                  40                  45

Gly Ala Asp Thr Phe Val Phe Ala Ala Arg Thr Asp Ser Tyr Arg Thr
        50                  55                  60

Asp Ala Gly Val Phe Asn Asp Leu Ile Leu Asp Phe Asp Ala Ser Glu
65                  70                  75                  80

Asp Arg Ile Asp Leu Ser Ala Leu Gly Phe Ser Gly Phe Gly Asp Gly
                85                  90                  95

Tyr Asn Gly Thr Leu Leu Val Gln Leu Ser Ser Ala Gly Thr Arg Thr
                100                 105                 110

Tyr Leu Lys Ser Tyr Glu Glu Asp Leu Glu Gly Arg Arg Phe Glu Val
            115                 120                 125

Ala Leu Asp Gly Asp His Thr Gly Asp Leu Ser Ala Ala Asn Val Val
            130                 135                 140

Phe Ala Asp Asp Gly
145

(2) INFORMATION FOR SEQ ID NO:46:

(i) SEQUENCE CHARACTERISTICS:
        (A) LENGTH: 151 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:46:

Leu Glu Gly Thr Ala Gly Asn Asp Thr Leu Gly Gly Ser Asp Ala His
1               5                   10                  15

Glu Thr Leu Leu Gly Leu Asp Gly Asn Asp Arg Leu Asn Gly Gly Ala
            20                  25                  30

Gly Asn Asp Ile Leu Asp Gly Gly Ala Gly Arg Asp Asn Leu Thr Gly
            35                  40                  45

Gly Ala Gly Ala Asp Leu Phe Arg Val Ser Ala Arg Thr Asp Ser Tyr
        50                  55                  60

Arg Thr Asp Ser Ala Ser Phe Asn Asp Leu Ile Thr Asp Phe Asp Ala
65                  70                  75                  80

Ser Gln Asp Arg Ile Asp Leu Ser Ala Leu Gly Phe Thr Gly Leu Gly
                85                  90                  95

Asp Gly Tyr Asn Gly Thr Leu Leu Leu Gln Val Ser Ala Asp Gly Ser
            100                 105                 110

Arg Thr Tyr Leu Lys Ser Leu Glu Ala Asp Ala Glu Gly Arg Arg Phe
        115                 120                 125

Glu Ile Ala Leu Asp Gly Asn Phe Ala Gly Leu Leu Gly Ala Gly Asn
130                 135                 140

Leu Leu Phe Glu Arg Thr Ala
145                 150

(2) INFORMATION FOR SEQ ID NO:47:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:47:

Ile Glu Gly Asp Ala Gly Asp Asn Ala Leu Leu Gly Thr Ser Ala Ala
1               5                   10                  15

Glu Thr Leu Leu Gly His Ala Gly Asn Asp Thr Leu Asp Gly Gly Ala
            20                  25                  30

Gly Asp Asp Ile Leu Val Gly Gly Ala Gly Arg Asp Ser Leu Thr Gly
        35                  40                  45

Gly Ala Gly Ala Asp Val Phe Arg Phe Asp Ala Leu Ser Asp Ser Gln
50                  55                  60

Arg Asn Tyr Asp Ile Gly Asp Asn Gln Gly Asp Arg Ile Ala Asp Phe
65                  70                  75                  80

Ala Val Gly Glu Asp Lys Leu Asp Val Ser Ala Leu Gly Phe Thr Gly
            85                  90                  95

Leu Gly Asp Gly Tyr Asn Gly Thr Leu Ala Leu Val Leu Asn Ser Ala
            100                 105                 110

Gly Asp Arg Thr Tyr Val Lys Ser Tyr Glu Asn Gly Ala Asp Gly Tyr
        115                 120                 125

Arg Phe Glu Phe Ser Leu Asp Gly Asn Tyr Leu Glu Leu Leu Gly Asn
130                 135                 140

Glu Asp Phe Ile Phe Ala Thr Pro Ser
145                 150

(2) INFORMATION FOR SEQ ID NO:48:

(i) SEQUENCE CHARACTERISTICS:
        (A) LENGTH: 132 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:48:

Leu Glu Gly Ser Ala Gly Asn Asp Ser Leu Gln Gly Thr Ala Ala Asp
1               5                   10                  15

Glu Val Ile His Gly Gly Gly Arg Asp Thr Leu Ala Gly Gly Ala
            20                  25                  30

Gly Ala Asp Val Phe Arg Phe Ser Glu Leu Thr Asp Ser Tyr Arg Asp
        35                  40                  45

Ser Ala Ser Tyr Ala Asp Leu Ile Thr Asp Phe Asp Ala Ser Glu Asp
50                  55                  60

Arg Ile Asp Leu Ser Gly Leu Gly Phe Ser Gly Leu Gly Asn Gly Tyr
65                  70                  75                  80

Gly Gly Thr Leu Ala Leu Gln Val Asn Ser Ala Gly Thr Arg Thr Tyr
                85                  90                  95

Leu Lys Ser Phe Glu Thr Asn Ala Ala Gly Glu Arg Phe Glu Ile Ala
                100                 105                 110

Leu Asp Gly Asp Leu Ser Ala Leu Gly Gly Ala Asn Leu Ile Leu Asp
                115                 120                 125

Ala Arg Thr Val
        130

(2) INFORMATION FOR SEQ ID NO:49:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:49:

Leu Ala Gly Gly Asp Gly Asn Asp Thr Leu Ser Gly Ser Ser Ala Ala
1                   5                   10                  15

Glu Glu Leu Leu Gly Gly Val Gly Asn Asp Ser Leu Asp Gly Gly Ala
                20                  25                  30

Gly Asn Asp Ile Leu Asp Gly Gly Ala Gly Arg Asp Thr Leu Ser Gly
                35                  40                  45

Gly Ser Gly Ser Asp Ile Phe Arg Phe Gly Gly Ala Leu Asp Ser Phe
                50                  55                  60

Arg Asn Tyr Ala Ser Gly Thr Asn Gly Thr Asp Ser Ile Thr Asp Phe
65                  70                  75                  80

Thr Pro Gly Glu Asp Leu Ile Asp Leu Ser Val Leu Gly Tyr Thr Gly
                85                  90                  95

Leu Gly Asp Gly Tyr Asn Gly Thr Leu Ala Ile Val Leu Asn Asp Ala
                100                 105                 110

Gly Thr Lys Thr Tyr Leu Lys Asn Arg Glu Ser Asp Ala Glu Gly Asn
                115                 120                 125

Gln Phe Glu Ile Ala Leu Glu Gly Asn His Ala Asp Gln Leu Asp Ala
                130                 135                 140

Ser Asp Phe Ile Phe Ala Thr Ala Ala
145                 150

(2) INFORMATION FOR SEQ ID NO:50:

(i) SEQUENCE CHARACTERISTICS:
        (A) LENGTH: 151 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:50:

Leu Glu Gly Thr Ala Gly Asn Asp Val Leu Ser Gly Thr Gly Ala His
1                   5                   10                  15

Glu Leu Ile Leu Gly Leu Ala Gly Asn Asp Arg Leu Asp Gly Gly Ala
                20                  25                  30

Gly Asp Asp Thr Leu Asp Gly Gly Ala Gly Arg Asp Thr Leu Thr Gly
                35                  40                  45

```
Gly Ala Gly Ala Asp Thr Phe Arg Phe Ser Ala Arg Glu Asp Ser His
    50                  55                  60
Arg Thr Asp Ser Ala Ser Phe Thr Asp Leu Ile Thr Asp Phe Asp Ala
65                  70                  75                  80
Ser Gln Asp Arg Ile Asp Leu Ser Ala Leu Gly Phe Thr Gly Leu Gly
                85                  90                  95
Asn Gly Tyr Asp Gly Thr Leu Ala Val Thr Thr Gly Ser Gly Gly Thr
            100                 105                 110
Arg Thr Tyr Leu Lys Ser Tyr Glu Val Asp Ala Gln Gly Arg Arg Phe
        115                 120                 125
Glu Ile Ala Leu Asp Gly Asn Phe Val Gly Gln Phe Asn Asp Gly Asn
130                 135                 140
Leu Leu Phe Asp Ala Ala Pro
145                 150

(2) INFORMATION FOR SEQ ID NO:51:

(i) SEQUENCE CHARACTERISTICS:
        (A) LENGTH: 153 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:51:

Val Thr Gly Thr Glu Gly Asn Asp Asn Leu Ser Gly Thr Asp Ala Gly
1               5                   10                  15
Glu Thr Leu Leu Gly Tyr Gly Gly Asn Asp Thr Leu Asn Gly Gly Ala
                20                  25                  30
Gly Asn Asp Ile Leu Val Gly Gly Ala Gly Arg Asp Thr Leu Thr Gly
            35                  40                  45
Gly Ala Gly Ala Asp Val Phe Arg Phe Glu Ala Leu Ser Asp Ser Gln
    50                  55                  60
Arg Asn Tyr Thr Ala Gly Asp Asn Gln Gly Asp Tyr Ile Ile Asp Phe
65                  70                  75                  80
Ala Val Gly Glu Asp Arg Ile Asp Val Ser Ala Leu Gly Tyr Thr Gly
                85                  90                  95
Leu Gly Asn Gly Arg Asn Gly Thr Leu Ala Val Val Leu Asn Ser Ala
            100                 105                 110
Gly Asp Arg Thr Tyr Val Lys Ser Tyr Asp Thr Asp Ala Asn Gly Tyr
        115                 120                 125
Asn Phe Glu Leu Ser Leu Ala Gly Asn Tyr Gln Gly Leu Leu Gly Ala
130                 135                 140
Glu Gln Phe Val Phe Ala Thr Pro Pro
145                 150

(2) INFORMATION FOR SEQ ID NO:52:

(i) SEQUENCE CHARACTERISTICS:
        (A) LENGTH: 150 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:52:

Ile Glu Gly Thr Asp Gly Asn Asp Ser Leu Gln Gly Thr Gly Ala Asp
1               5                   10                  15
```

-continued

```
Glu Leu Leu Leu Gly Leu Gly Gly Arg Asp Ser Leu Asn Gly Gly Ala
            20              25                  30

Gly Asp Asp Val Leu Asp Gly Gly Ala Glu Arg Asp Thr Leu Thr Gly
        35              40                  45

Gly Thr Gly Ala Asp Thr Phe Leu Phe Ser Ala Arg Thr Asp Ser Tyr
    50              55                  60

Arg Thr Asp Ser Ala Ser Phe Thr Asp Leu Ile Thr Asp Phe Asp Pro
65              70                  75                  80

Ala Gln Asp Arg Ile Asp Leu Ser Gly Leu Gly Phe Ser Gly Phe Gly
            85              90                  95

Asn Gly Tyr Asp Gly Thr Leu Leu Leu Gln Val Asn Ala Ala Gly Thr
            100             105                 110

Arg Thr Tyr Leu Lys Ser Leu Glu Ala Asp Ala Asp Gly Gln Arg Phe
        115             120                 125

Glu Ile Ala Leu Asp Gly Asp Phe Ser Gly Gln Leu Asp Ser Gly Asn
        130             135                 140

Val Ile Phe Glu Ala Gly
145             150
```